US012747430B2

(12) United States Patent
Gorsuch et al.

(10) Patent No.: US 12,747,430 B2
(45) Date of Patent: Sep. 29, 2026

(54) ENGINEERED MEGANUCLEASES HAVING SPECIFICITY FOR A RECOGNITION SEQUENCE IN THE TRANSTHYRETIN GENE

(71) Applicant: Precision Biosciences, Inc., Durham, NC (US)

(72) Inventors: Cassandra Gorsuch, Durham, NC (US); Jochen Genschel, Raleigh, NC (US); Janel Lape, Wake Forest, NC (US); Derek Jantz, Durham, NC (US); James Jefferson Smith, Morrisville, NC (US)

(73) Assignee: Precision BioSciences, Inc., Durham, NC (US)

( * ) Notice: Subject to any disclaimer, the term of this patent is extended or adjusted under 35 U.S.C. 154(b) by 690 days.

(21) Appl. No.: 18/022,247

(22) PCT Filed: Aug. 20, 2021

(86) PCT No.: PCT/US2021/046987

§ 371 (c)(1),
(2) Date: Feb. 20, 2023

(87) PCT Pub. No.: WO2022/040582

PCT Pub. Date: Feb. 24, 2022

(65) Prior Publication Data

US 2024/0011003 A1 Jan. 11, 2024

Related U.S. Application Data

(60) Provisional application No. 63/068,965, filed on Aug. 21, 2020.

(51) Int. Cl.

| | |
|---|---|
| *C12N 9/22* | (2006.01) |
| *A61K 38/46* | (2006.01) |
| *A61K 48/00* | (2006.01) |
| *C12N 15/86* | (2006.01) |
| *C12N 15/90* | (2006.01) |

(52) U.S. Cl.

CPC .............. *C12N 9/22* (2013.01); *A61K 38/465* (2013.01); *A61K 48/0041* (2013.01); *C12N 15/86* (2013.01); *C12N 15/907* (2013.01); *C12N 2750/14143* (2013.01); *C12N 2800/80* (2013.01)

(58) Field of Classification Search

CPC .............................. C12N 15/86; C12N 15/907

See application file for complete search history.

(56) References Cited

FOREIGN PATENT DOCUMENTS

| | | | |
|---|---|---|---|
| WO | WO 2017/112859 | A1 | 6/2017 |
| WO | WO 2019/089913 | A1 | 5/2019 |
| WO | WO 2019/185920 | A1 | 10/2019 |

*Primary Examiner* — Laura Schuberg
*Assistant Examiner* — Nicholas A Humphries
(74) *Attorney, Agent, or Firm* — Womble Bond Dickinson (US) LLP

(57) ABSTRACT

The present invention encompasses engineered meganucleases that bind and cleave a recognition sequence within a TTR gene. The present invention also encompasses methods of using such engineered meganucleases to make genetically-modified cells. Further, the invention encompasses pharmaceutical compositions comprising engineered meganuclease proteins, or nucleic acids encoding engineered meganucleases of the invention, and the use of such compositions for treatment of TTR-associated diseases, such as transthyretin amyloidosis.

17 Claims, 19 Drawing Sheets

Specification includes a Sequence Listing.

TTR15 Half-Site

TTR16 Half-Site

| | | |
|---|---|---|
| TTR 15-16 | TGCATGGGCTCACAACTGAGGA | SEQ ID NO:7 |
| Recognition Sequence | ACGTACCCGAGTGTTGACTCCT | SEQ ID NO:8 |

FIGURE 1

| | TTR5 Half-Site / TTR6 Half-Site | |
|---|---|---|
| TTR 5-6 | GCTGGACTGGTATTTGTGTCTG | SEQ ID NO:9 |
| Recognition Sequence | CGACCTGACCATAAACACAGAC | SEQ ID NO:10 |

FIGURE 2

| | | |
|---|---|---|
| TTR 5-6L.1204(SEQ ID NO:15) | MNTKYNKEFLLYLAGFVDGDGSIFASIEPAQRAKFKHYLRLVFNVTQKTQRRWFLDKLVD | 60 |
| TTR 5-6L.1204(SEQ ID NO:15) | EIGVGYVSDSGSVSLYKLSEIKPLHNFLTQLQPFLKLKQKQANLVLKIIEQLPSAKESPD | 120 |
| TTR 5-6L.1204(SEQ ID NO:15) | KFLEVCTWVDQIAALNDSKTRKTTSETVRAVLDSLPGSVGGLSPSQASSAASSASSSPGS | 180 |
| TTR 5-6L.1204(SEQ ID NO:15) | GISEALRAGAGSGTGYNKEFLLYLAGFVDSDGSIFASIVPDQSRKFKHALRLRFIVSQNT | 240 |
| TTR 5-6L.1204(SEQ ID NO:15) | RRRWFLDKLVDEIGVGYVKDSGRSAHYTLSEIKPLHNFLTQLQPFLKLKQKQANLVLKII | 300 |
| TTR 5-6L.1204(SEQ ID NO:15) | EQLPSAKESPDKFLEVCTWVDQIAALNDSKTRKTTSETVRAVLDSLSEKKKSSP 354 | |

FIGURE 4A

```
TTR 15-16L.164(SEQ ID NO: 13)    MNTKYNKEFLLYLAGFVDADGSIYACITPRQLCKFKHGLALGFSVIQRTRRRWFLDKLVD    60
TTR 15-16L.161(SEQ ID NO: 12)    MNTKYNKEFLLYLAGFVDADGSIYACITPRQDYKFKHNLALGFSVIQRTRRRWFLDKLVD    60
TTR 15-16x.81(SEQ ID NO: 11)     MNTKYNKEFLLYLAGFVDADGSIYACITPRQTHKFKHVLALGFSVIQRTRRRWFLDKLVD    60
TTR 15-16L.181(SEQ ID NO: 14)    MNTKYNKEFLLYLAGFVDADGSIYACITPRQTHKFKHNLALGFSVIQRTRRRWFLDKLVD    60
                                 *******************************  **** **********************

TTR 15-16L.164(SEQ ID NO: 13)    EIGVGYVRDRDTTSEYRLSQIKPLHNFLTQLQPFLKLKQKQANLVLKIIEQLPSAKESPD    120
TTR 15-16L.161(SEQ ID NO: 12)    EIGVGYVRDRDTTSEYRLSQIKPLHNFLTQLQPFLKLKQKQANLVLKIIEQLPSAKESPD    120
TTR 15-16x.81(SEQ ID NO: 11)     EIGVGYVRDRDTTSEYRLSQIKPLHNFLTQLQPFLKLKQKQANLVLKIIEQLPSAKESPD    120
TTR 15-16L.181(SEQ ID NO: 14)    EIGVGYVRDRDTTSEYRLSQIKPLHNFLTQLQPFLKLKQKQANLVLKIIEQLPSAKESPD    120
                                 ************************************************************

TTR 15-16L.164(SEQ ID NO: 13)    KFLEVCTWVDQIAALNDSRTRKTTSETVRAVLDSLPGSVGGLSPSQASSAASSASSSPGS    180
TTR 15-16L.161(SEQ ID NO: 12)    KFLEVCTWVDQIAALNDSRTRKTTSETVRAVLDSLPGSVGGLSPSQASSAASSASSSPGS    180
TTR 15-16x.81(SEQ ID NO: 11)     KFLEVCTWVDQIAALNDSRTRKTTSETVRAVLDSLPGSVGGLSPSQASSAASSASSSPGS    180
TTR 15-16L.181(SEQ ID NO: 14)    KFLEVCTWVDQIAALNDSRTRKTTSETVRAVLDSLPGSVGGLSPSQASSAASSASSSPGS    180
                                 ************************************************************

TTR 15-16L.164(SEQ ID NO: 13)    GISEALRAGAGSGTGYNKEFLLYLAGFVDGDGSIYASIDPDQRSKFKHGLRLNFQVSQKT    240
TTR 15-16L.161(SEQ ID NO: 12)    GISEALRAGAGSGTGYNKEFLLYLAGFVDGDGSIYASIDPDQRSKFKHGLRLNFQVSQKT    240
TTR 15-16x.81(SEQ ID NO: 11)     GISEALRAGAGSGTGYNKEFLLYLAGFVDGDGSIYASIDPDQRSKFKHGLRLNFQVSQKT    240
TTR 15-16L.181(SEQ ID NO: 14)    GISEALRAGAGSGTGYNKEFLLYLAGFVDGDGSIYASIDPDQRSKFKHGLRLNFQVSQKT    240
                                 ************************************************************

TTR 15-16L.164(SEQ ID NO: 13)    QRRWFLDKLVDEIGVGYVQDKGSVSHYILSEIKPLHNFLTQLQPFLKLKQKQANLVLKII    300
TTR 15-16L.161(SEQ ID NO: 12)    QRRWFLDKLVDEIGVGYVQDKGSVSHYILSEIKPLHNFLTQLQPFLKLKQKQANLVLKII    300
TTR 15-16x.81(SEQ ID NO: 11)     QRRWFLDKLVDEIGVGYVQDKGSVSHYILSQIKPLHNFLTQLQPFLKLKQKQANLVLKII    300
TTR 15-16L.181(SEQ ID NO: 14)    QRRWFLDKLVDEIGVGYVQDKGSVSHYILSEIKPLHNFLTQLQPFLKLKQKQANLVLKII    300
                                 ****************************** *****************************

TTR 15-16L.164(SEQ ID NO: 13)    EQLPSAKESPDKFLEVCTWVDQIAALNDSKTRKTTSETVRAVLDSLSEKKKSSP 354
TTR 15-16L.161(SEQ ID NO: 12)    EQLPSAKESPDKFLEVCTWVDQIAALNDSKTRKTTSETVRAVLDSLSEKKKSSP 354
TTR 15-16x.81(SEQ ID NO: 11)     EQLPSAKESPDKFLEVCTWVDQIAALNDSKTRKTTSETVRAVLDSLSEKKKSSP 354
TTR 15-16L.181(SEQ ID NO: 14)    EQLPSAKESPDKFLEVCTWVDQIAALNDSKTRKTTSETVRAVLDSLSEKKKSSP 354
                                 ******************************************************
```

FIGURE 4B

ENGINEERED MEGANUCLEASES HAVING SPECIFICITY FOR A RECOGNITION SEQUENCE IN THE TRANSTHYRETIN GENE

FIELD OF THE INVENTION

The invention relates to the field of oncology, molecular biology and recombinant nucleic acid technology. In particular, the invention relates to optimized engineered meganucleases having specificity for a recognition sequence within the transthyretin (TTR) gene. Such engineered meganucleases are useful in methods for treating transthyretin amyloidosis.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Aug. 20, 2021, is named P109070034W000-SEQ-EPG and is 59,876 bytes in size.

BACKGROUND OF THE INVENTION

Transthyretin amyloidosis (ATTR) is a progressive amyloid type of disease where production and deposition of amyloid fibrils occurs in various tissues and organ systems of the body. Normally, the TTR protein is a serum/plasma and cerebrospinal fluid protein responsible for the transport of thyroxine and retinol. It is synthesized primarily by the liver, the choroid plexus of the brain, and to a minor extent, in the retina in humans. TTR synthesized in the liver is secreted into the blood and TTR originating in the choroid plexus is destined for the cerebrospinal fluid.

TTR diseases are caused by over 100 known point mutations in the transthyretin (TTR) protein. These point mutations result in misfolding of the protein and the formation of the amyloid fibrils. It is thought that ATTR disease is caused by aggregation of the misfolded proteins, which causes neuronal and cellular dysfunction rather than loss of function of the TTR protein. There are primarily three forms of the disease including neuropathic ATTR, leptomeningeal ATTR, and cardiac ATTR. In addition, ATTR is associated with the relatively common disorders senile systemic amyloidosis (SSA), familial amyloid polyneuropathy (FAP), and familial amyloid cardiopathy (FAC). Recent epidemiological studies have indicated that the TTR associated SSA disorder may affect as much as 25% of the elderly population (Tanskanen et al, *Ann Med.* 2008; 40(3):232-9).

Biochemically, TTR was identified as the major protein component in the amyloid deposits of FAP patients (Costa et al, *Proc. Natl. Acad Sci. USA* 1978, 75:4499-4503). It was later discovered that a substitution of methionine for valine at position 30 (V30M) of the protein was found to be the most common molecular defect causing the disease (Saraiva et al, *J. Clin. Invest.* 1984, 74: 104-119). In FAP, widespread systemic extracellular deposition of TTR aggregates and amyloid fibrils occurs throughout the connective tissue, particularly in the peripheral nervous system (Sousa and Saraiva, *Prog. Neurobiol.* 2003, 71: 385-400). Following TTR deposition, axonal degeneration occurs, starting in the unmyelinated and myelinated fibers of low diameter, and ultimately leading to neuronal loss at ganglionic sites.

The neuropathic forms of the disease affect peripheral and autonomic nervous systems, which result in peripheral neuropathy and reduced control of bodily functions including, inter alia, sexual impotence, diarrhea, constipation, problems with urination, and orthostatic hypotension. In addition, problems with the kidney, eyes, and wrists (carpal tunnel syndrome) are common. Accumulation of TTR protein in the leptomeninges can cause stroke and bleeding in the brain, hydrocephalus, ataxia, spastic paralysis, seizures, dementia, and various eye disorders. Cardiac amyloidosis patients present with arrhythmias, enlarged hearts, or orthostatic hypertension, which can lead to heart failure and death.

TTR amyloidosis typically leads to death within ten years of diagnosis or presentation of symptoms, and until recently, was considered incurable. Liver transplantation can represent an effective means of replacing disease-associated allele by a wild type (WT) allele in familial cases because the liver is typically the source of amyloidogenic TTR. While liver transplantation is effective as a form of gene therapy it is not without problems. Transplantation is complicated by the need for invasive surgery for the recipient and the donor, long-term post-transplantation immunosuppressive therapy, a shortage of donors, high cost, and the large number of TTR patients that are not good candidates because of advanced disease progression. Unfortunately, cardiac amyloidosis progresses in some familial patients even after liver transplantation because WT TTR often continues to deposit. Transplantation is not a viable option for the most prevalent TTR disease, senile systemic amyloidosis (SSA), affecting approximately 25% of those over 80 due to the deposition of WT TTR.

Alternative treatment options for ATTR in development include anti-sense technology as described in, for example, U.S. Patent Application Publication No. US2011/0294868 and the lipid nanoparticle (LNP)-encapsulated siRNA patisiran as described by Suhr et al., *Orphanet Journal of Rare diseases* 10:109, pp. 1-9 (2015). In addition, the CRISPR/Cas9 gene editing system has been used to reduce serum TTR levels in mice (see Finn et al., *Cell Reports* 22, pp. 2227-2235 (2018). Despite these recent efforts, there remains a need for alternative therapies that achieve a stable reduction in TTR levels in patients having ATTR disease.

Accordingly, described herein are methods and compositions for achieving a reduction in TTR levels using engineered homing endonucleases (also called a "meganuclease"). Homing endonucleases are a group of naturally-occurring nucleases that recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38: 49-95). Homing endonucleases are commonly grouped into four families: the LAGLIDADG (SEQ ID NO: 2) family, the GIY-YIG family, the His-Cys box family and the HNH family. These families are characterized by structural motifs, which affect catalytic activity and recognition sequence. For instance, members of the LAGLIDADG (SEQ ID NO: 2) family are characterized by having either one or two copies of the conserved LAGLIDADG (SEQ ID NO: 2) motif (see Chevalier et al. (2001), *Nucleic Acids Res.* 29(18): 3757-3774). The LAGLIDADG (SEQ ID NO: 2) homing endonucleases with a single copy of the LAGLIDADG (SEQ ID NO: 2) motif form homodimers, whereas members with two copies of the LAGLIDADG (SEQ ID NO: 2) motif are found as monomers. Methods for producing homing endonucleases are known in the art.

I-CreI (SEQ ID NO: 1) is a member of the LAGLIDADG (SEQ ID NO: 2) family of homing endonucleases, which recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58). Methods for rationally-designing mono-LAGLIDADG (SEQ ID NO: 2) homing endonucleases were described, which are capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li et al. (2009), *Nucleic Acids Res.* 37:1650-62; Grizot et al. (2009), *Nucleic Acids Res.* 37:5405-19). Thus, a functional "single-chain" meganuclease can be expressed from a single transcript. This coupled with the extremely low frequency of off-target cutting observed with engineered meganucleases makes them the preferred endonuclease for the present invention.

Accordingly, the present invention fulfills a need in the art for gene therapy approaches to treat ATTR or other TTR-associated diseases.

SUMMARY OF THE INVENTION

The present invention provides engineered meganucleases that bind and cleave a recognition sequence in exon 1 or exon 3 of a transthyretin (TTR) gene (e.g., TTR 15-16 recognition sequence (SEQ ID NO: 7) or TTR 5-6 recognition sequence (SEQ ID NO: 9), which are conserved in the TTR genes of mice, humans, and non-human primates). Cleavage at the recognition sequence by an engineered meganuclease disclosed herein can modify expression of TTR due to non-homologous end joining (NHEJ) at the cleavage site. NHEJ can result in insertions, deletions, or result in a frameshift mutation that can interfere with gene expression. Alternatively, a sequence of interest can be introduced into a TTR gene via homologous recombination. Accordingly, by interrupting normal gene expression, the expression of the endogenous TTR polypeptide can be reduced according to the methods disclosed herein. Such meganucleases are, therefore, useful for reducing TTR polypeptide levels in individuals having transthyretin amyloidosis (ATTR) or other TTR-associated diseases, such as senile systemic amyloidosis (SSA), familial amyloid polyneuropathy (FAP), or familial amyloid cardiopathy (FAC). Thus, the present invention also provides pharmaceutical compositions and methods for treatment of a subject having ATTR or other TTR-associated diseases, which utilize an engineered meganuclease having specificity for a recognition sequence comprising SEQ ID NO: 7 or 9 within a TTR gene.

Thus, in one aspect, the invention provides an engineered meganuclease that recognizes and cleaves a recognition sequence in a transthyretin (TTR) gene, wherein said engineered meganuclease comprises a first subunit and a second subunit, wherein said first subunit binds to a first recognition half-site of said recognition sequence and comprises a first hypervariable (HVR1) region, and wherein said second subunit binds to a second recognition half-site of said recognition sequence and comprises a second hypervariable (HVR2) region. In some embodiments, the recognition sequence comprises SEQ ID NO: 7.

In some embodiments, the HVR1 region comprises an amino acid sequence having at least 80%, at least 85%, at least 90%, at least 91%, at least 92%, at least 93%, at least 94%, at least 95%, at least 96%, at least 97%, at least 98%, at least 99%, or more sequence identity to an amino acid sequence corresponding to residues 24-79 of any one of SEQ ID NOs: 11-14. In certain embodiments, the HVR1 region comprises an amino acid sequence corresponding to residues 24-79 of any one of SEQ ID NOs: 11-14 with up to 1, 2, 3, 4, 5, 6, 7, 8, 9, 10, or 11 amino acid substitutions.

In some embodiments, the HVR1 region comprises one or more residues corresponding to residues 24, 26, 28, 30, 32, 33, 38, 40, 42, 44, 46, 68, 70, 75, and 77 of any one of SEQ ID NOs: 11-14. In some embodiments, the HVR1 region comprises residues corresponding to residues 24, 26, 28, 30, 32, 33, 38, 40, 42, 44, 46, 68, 70, 75, and 77 of any one of SEQ ID NOs: 11-14.

In certain embodiments, the HVR1 region comprises Y, R, K, or D at a residue corresponding to residue 66 of any one of SEQ ID NOs: 11-14.

In some embodiments, the HVR1 region comprises one or more residues corresponding to residues 48, 50, and 71-73, of any one of SEQ ID NOs: 11-14

In certain embodiments, the HVR1 region comprises residues 24-79 of any one of SEQ ID NOs: 11-14.

In particular embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 7-153 of any one of SEQ ID NOs: 11-14. In particular embodiments, the first subunit comprises an amino acid sequence corresponding to residues 7-153 of any one of SEQ ID NOs: 11-14 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In certain embodiments, the first subunit comprises G, S, or A at a residue corresponding to residue 19 of any one of SEQ ID NOs: 11-14.

In some embodiments, the first subunit comprises residues corresponding to residues 19 and 139 of any one of SEQ ID NOs: 11-14.

In certain embodiments, the first subunit comprises E, Q, or K at a residue corresponding to residue 80 of any one of SEQ ID NOs: 11-14.

In some embodiments, the first subunit comprises a residue corresponding to residue 80 of any one of SEQ ID NOs: 11-14. In particular embodiments, the first subunit comprises residues 7-153 of any one of SEQ ID NOs: 11-14.

In some embodiments, the HVR2 region comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 215-270 of any one of SEQ ID NOs: 11-14. In certain embodiments, the HVR2 region comprises an amino acid sequence corresponding to residues 215-270 of any one of SEQ ID NOs: 11-14 with up to 1, 2, 3, 4, 5, 6, 7, 8, 9, 10, or 11 amino acid substitutions.

In certain embodiments, the HVR2 region comprises one or more residues corresponding to residues 215, 217, 219, 221, 223, 224, 229, 231, 233, 235, 237, 259, 261, 266, and 268 of any one of SEQ ID NOs: 11-14. In certain embodiments, the HVR2 region comprises residues corresponding to residues 215, 217, 219, 221, 223, 224, 229, 231, 233, 235, 237, 259, 261, 266, and 268 of any one of SEQ ID NOs: 11-14.

In certain embodiments, the HVR2 region comprises Y, R, K, or D at a residue corresponding to residue 257 of any one of SEQ ID NOs: 11-14.

In particular embodiments, the HVR2 region comprises residues 215-270 of any one of any one of SEQ ID NOs: 11-14.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 198-344 of any one of SEQ ID NOs: 11-14. In particular embodiments, the second subunit comprises an amino acid sequence corresponding to residues 198-344 of any one of SEQ ID NOs: 11-14 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In certain embodiments, the second subunit comprises G, S, or A at a residue corresponding to residue 210 of any one of SEQ ID NOs: 11-14.

In certain embodiments, the second subunit comprises E, Q, or K at a residue corresponding to residue 271 of any one of SEQ ID NOs: 11-14. In some embodiments, the second subunit comprises a residue corresponding to residue 271 of any one of SEQ ID NO: 11.

In particular embodiments, the second subunit comprises residues 198-344 of any one of SEQ ID NOs: 11-14.

In some embodiments, the first subunit of the engineered meganuclease has at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 7-153 of any one of SEQ ID NOs: 11-14 and the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 198-344 of any one of SEQ ID NOs: 11-14. In certain embodiments, the first subunit and/or the second subunit can comprise up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions relative to residues 7-153 and residues 198-344, respectively, of any one of SEQ ID NOs: 11-14.

In certain embodiments, the engineered meganuclease is a single-chain meganuclease comprising a linker, wherein the linker covalently joins the first subunit and the second subunit.

In particular embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to any one of SEQ ID NOs: 11-14.

In particular embodiments, the engineered meganuclease comprises the amino acid sequence of any one of SEQ ID NOs: 11-14.

In particular embodiments, the engineered meganuclease is encoded by a nucleic acid sequence having at least 80%, at least 85%, at least 90%, at least 91%, at least 92%, at least 93%, at least 94%, at least 95%, at least 96%, at least 97%, at least 98%, at least 99%, or more, sequence identity to any one of SEQ ID NOs: 66-69.

In particular embodiments, the engineered meganuclease is encoded by a nucleic acid sequence of any one of SEQ ID NOs: 66-69.

In some embodiments, the recognition sequence comprises SEQ ID NO: 9.

In some embodiments, the HVR1 region comprises an amino acid sequence having at least 80%, at least 85%, at least 90%, at least 91%, at least 92%, at least 93%, at least 94%, at least 95%, at least 96%, at least 97%, at least 98%, at least 99%, or more sequence identity to an amino acid sequence corresponding to residues 24-79 of SEQ ID NO: 15. In particular embodiments, the first subunit comprises an amino acid sequence corresponding to residues 7-153 of SEQ ID NO: 15 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In some embodiments, the HVR1 region comprises one or more residues corresponding to residues 24, 26, 28, 30, 32, 33, 38, 40, 42, 44, 46, 68, 70, 75, and 77 of SEQ ID NO: 15. In some embodiments, the HVR1 region comprises residues corresponding to residues 24, 26, 28, 30, 32, 33, 38, 40, 42, 44, 46, 68, 70, 75, and 77 of SEQ ID NO: 15.

In certain embodiments, the HVR1 region comprises Y, R, K, or D at a residue corresponding to residue 66 of SEQ ID NO: 15.

In some embodiments, the HVR1 region comprises residues 24-79 of SEQ ID NO: 15.

In particular embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 7-153 of SEQ ID NO: 15. In particular embodiments, the first subunit comprises an amino acid sequence corresponding to residues 7-153 of SEQ ID NO: 15 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In certain embodiments, the first subunit comprises G, S, or A at a residue corresponding to residue 19 of SEQ ID NO: 15.

In certain embodiments, the first subunit comprises E, Q, or K at a residue corresponding to residue 80 of SEQ ID NO: 15. In some embodiments, the first subunit comprises a residue corresponding to residue 80 of SEQ ID NO: 15.

In particular embodiments, the first subunit comprises residues 7-153 of SEQ ID NO: 15. In some embodiments, the HVR2 region comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 215-270 of SEQ ID NO: 15. In particular embodiments, the second subunit comprises an amino acid sequence corresponding to residues 215-270 of SEQ ID NO: 15 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In certain embodiments, the HVR2 region comprises one or more residues corresponding to residues 215, 217, 219, 221, 223, 224, 229, 231, 233, 235, 237, 259, 261, 266, and 268 of SEQ ID NO: 15. In certain embodiments, the HVR2 region comprises residues corresponding to residues 215, 217, 219, 221, 223, 224, 229, 231, 233, 235, 237, 259, 261, 266, and 268 of SEQ ID NO: 15.

In certain embodiments, the HVR2 region comprises Y, R, K, or D at a residue corresponding to residue 257 of SEQ ID NO: 15.

In particular embodiments, the HVR2 region comprises one or more residues corresponding to residues 239, 241, and 263-265 of SEQ ID NO: 15. In some embodiments, the HVR2 region comprises residues corresponding to residues 239, 241, and 263-265 of SEQ ID NO: 15.

In particular embodiments, the HVR2 region comprises residues 215-270 of SEQ ID NO: 15.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 198-344 of SEQ ID NO: 15. In particular embodiments, the second subunit comprises an amino acid sequence corresponding to residues 198-344 of SEQ ID NO: 15 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In certain embodiments, the second subunit comprises G, S, or A at a residue corresponding to residue 210 of SEQ ID NO: 15. In some embodiments, the second subunit comprises a residue corresponding to residue 210 of SEQ ID NO: 15.

In certain embodiments, the second subunit comprises E, Q, or K at a residue corresponding to residue 271 of SEQ ID NO: 15. In some embodiments, the second subunit comprises a residue corresponding to residue 271 of SEQ ID NO: 15.

In particular embodiments, the second subunit comprises residues 198-344 of SEQ ID NO: 15.

In some embodiments, the first subunit of the engineered meganuclease has at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 7-153 of SEQ ID NO: 15 and the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 198-344 of SEQ ID NO: 15. In certain embodiments, the first subunit and/or the second subunit can comprise up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions relative to residues 7-153 and residues 198-344, respectively, of SEQ ID NO: 15.

In certain embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence of SEQ ID NO: 15.

In particular embodiments, the engineered meganuclease comprises the amino acid sequence of SEQ ID NO: 15.

In some embodiments, the engineered meganuclease is encoded by a nucleic acid sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of SEQ ID NO: 70.

In some embodiments, the engineered meganuclease is encoded by a nucleic acid sequence of SEQ ID NO: 70.

In another aspect, the invention provides a polynucleotide comprising a nucleic acid sequence encoding an engineered meganuclease described herein.

In certain embodiments, the polynucleotide is an mRNA.

In another aspect, the invention provides a recombinant DNA construct comprising a polynucleotide comprising a nucleic acid sequence described herein.

In certain embodiments, the recombinant DNA construct encodes a recombinant virus comprising the polynucleotide comprising a nucleic acid sequence encoding an engineered meganuclease disclosed herein. In some embodiments, the recombinant virus is a recombinant adenovirus, a recombinant lentivirus, a recombinant retrovirus, or a recombinant adeno-associated virus (AAV) In particular embodiments, the recombinant virus is a recombinant AAV. In some embodiments, the recombinant AAV encoded by the recombinant DNA construct has an AAV8 serotype. In some embodiments, the said nucleic acid sequence comprises a promoter sequence operably linked to the nucleic acid sequence encoding the engineered meganuclease. In some embodiments, the promoter is a liver specific promoter. In some embodiments, the liver specific promoter comprises a human thyroxine binding globulin (TBG) promoter, a human alpha-1 antitrypsin promoter, a hybrid liver specific promoter, or an apolipoprotein A-II promoter.

In another aspect, the invention provides a recombinant virus comprising a polynucleotide comprising a nucleic acid sequence encoding an engineered meganuclease described herein. In some embodiments, the recombinant virus is a recombinant adenovirus, a recombinant lentivirus, a recombinant retrovirus, or a recombinant AAV. In particular embodiments, the recombinant virus is a recombinant AAV. In some embodiments, the recombinant AAV has an AAV8 serotype.

In another aspect, the invention provides a method for producing a genetically-modified eukaryotic cell having a disrupted target sequence in a chromosome of the genetically-modified eukaryotic cell, the method comprising introducing into a eukaryotic cell a polynucleotide comprising a nucleic acid sequence encoding any engineered meganuclease of the invention, wherein the engineered meganuclease is expressed in the eukaryotic cell; wherein the engineered meganuclease produces a cleavage site in the chromosome at a recognition sequence comprising SEQ ID NO: 7 or 9; and wherein the target sequence is modified by non-homologous end-joining at said cleavage site.

In some embodiments, the method produces a modified TTR gene that does not encode a full-length endogenous TTR polypeptide. In some embodiments, the method is effective to reduce levels of an endogenous TTR polypeptide in the cell by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% relative to a reference level. In some embodiments, the TTR polypeptide levels are reduced by about 1-5%, 5%-10%, 10%-20%, 20%-30%, 30%-40%, 40%-50%, 50%-60%, 60%-70%, or 70%-80%, relative to a reference level.

In some embodiments, the eukaryotic cell is a mammalian cell. In one such embodiment, the mammalian cell is selected from a human cell, a non-human primate cell, or a mouse cell. In one embodiment, the mammalian cell is a hepatocyte. In certain embodiments, the hepatocyte is within the liver of a human, a non-human primate, or a mouse.

In some embodiments, the nucleic acid is introduced into the eukaryotic cell by an mRNA or a recombinant virus. In one such embodiment, the mRNA is packaged within a lipid nanoparticle. In another such an embodiment, the recombinant virus is a recombinant adenovirus, a recombinant lentivirus, a recombinant retrovirus, or a recombinant AAV. In a particular embodiment, the recombinant virus is a recombinant AAV.

In another aspect, the invention provides a method for producing a genetically-modified eukaryotic cell having a disrupted target sequence in a chromosome of the genetically-modified eukaryotic cell, the method comprising introducing into a eukaryotic cell any engineered meganuclease of the invention, wherein the engineered meganuclease produces a cleavage site in the chromosome at a recognition sequence comprising SEQ ID NO: 7 or 9; and wherein the target sequence is modified by non-homologous end-joining at the cleavage site.

In one embodiment, the method produces a modified TTR gene that does not encode a full-length endogenous TTR polypeptide. In some embodiments, the method is effective to reduce expression of an endogenous TTR polypeptide and thereby reduce TTR polypeptide levels in the cell by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, or at least about 80% relative to a reference level. In some embodiments, the TTR polypeptide levels are reduced by about 1-5%, 5%-10%, 10%-20%, 20%-30%, 30%-40%, 40%-50%, 50%-60%, 60%-70%, or 70%-80%, relative to a reference level.

In some embodiments, the eukaryotic cell is a mammalian cell. In some embodiments, the mammalian cell is selected from a human cell, a non-human primate cell, or a mouse cell. In particular embodiments, the mammalian cell is a hepatocyte. In some embodiments, the hepatocyte is within the liver of a human, a non-human primate, or a mouse.

In another aspect, the invention provides a method for producing a genetically-modified eukaryotic cell comprising an exogenous sequence of interest inserted into a chromosome of said genetically-modified eukaryotic cell, the method comprising introducing into a eukaryotic cell one or more polynucleotides comprising: (a) a first a nucleic acid sequence encoding any engineered meganuclease of the invention, wherein the engineered meganuclease is expressed in the eukaryotic cell; and (b) a second nucleic acid sequence including said sequence of interest; wherein the engineered meganuclease produces a cleavage site in the chromosome at a recognition sequence comprising SEQ ID NO: 7 or 9, and wherein the sequence of interest is inserted into said chromosome at said cleavage site.

In some embodiments, the second nucleic acid sequence further comprises nucleic acid sequences homologous to nucleic acid sequences flanking said cleavage site and said sequence of interest is inserted at said cleavage site by homologous recombination.

In some embodiments, the method produces a modified TTR gene that does not encode a full-length endogenous TTR polypeptide. In some embodiments, In some embodiments, the method is effective to reduce expression of an endogenous TTR polypeptide and thereby reduce TTR polypeptide levels in the cell by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or more, relative to a reference level. In some embodiments, the TTR polypeptide levels are reduced by about 1%-5%, 5%-10%, 10%-20%, 20%-30%, 30%-40%, 40%-50%, 50%-60%, 60%-70%, or 70%-80%, or more, relative to a reference level.

In some embodiments, the eukaryotic cell is a mammalian cell. In some embodiments, the mammalian cell is selected from a human cell, a non-human primate cell, or a mouse cell. In particular embodiments, the mammalian cell is a hepatocyte. In some embodiments, the hepatocyte is within the liver of a human, a non-human primate, or a mouse. In some embodiments, a polynucleotide comprising the first nucleic acid sequence is introduced into the eukaryotic cell by an mRNA or a recombinant virus. In one such embodiment, the mRNA is packaged within a lipid nanoparticle. In another such an embodiment, the recombinant virus is a recombinant adenovirus, a recombinant lentivirus, a recombinant retrovirus, or a recombinant AAV. In a particular embodiment, the recombinant virus is a recombinant AAV.

In some embodiments, a polynucleotide comprising the second nucleic acid sequence is introduced into the eukaryotic cell by a recombinant virus. In one such embodiment, the recombinant virus is a recombinant adenovirus, a recombinant lentivirus, a recombinant retrovirus, or a recombinant AAV. In a particular embodiment, the recombinant virus is a recombinant AAV.

In another aspect, the invention provides a method for producing a genetically-modified eukaryotic cell comprising an exogenous sequence of interest inserted into a chromosome of said genetically-modified eukaryotic cell, the method comprising (a) introducing into the eukaryotic cell any engineered meganuclease of the invention, and (b) introducing a polynucleotide comprising a nucleic acid sequence comprising the sequence of interest into the eukaryotic cell, wherein the engineered meganuclease produces a cleavage site in the chromosome at a recognition sequence comprising SEQ ID NO: 7 or 9, and wherein the sequence of interest is inserted into the chromosome at the cleavage site.

In some embodiments, the polynucleotide further comprises nucleic acid sequences homologous to nucleic acid sequences flanking the cleavage site and the sequence of interest is inserted at the cleavage site by homologous recombination. In some embodiments, the method produces a modified TTR gene that does not encode a full-length endogenous TTR polypeptide. In some embodiments, the method is effective to reduce TTR polypeptide levels in the cell by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or more, relative to a reference level. In some embodiments, the TTR polypeptide levels are reduced by about 1%-5%, 5%-10%, 10%-20%, 20%-30%, 30%-40%, 40%-50%, 50%-60%, 60%-70%, 70%-80%, or more, relative to a reference level.

In some embodiments, the eukaryotic cell is a mammalian cell. In some embodiments, the mammalian cell is selected from a human cell, a non-human primate cell, or a mouse cell. In particular embodiments, the mammalian cell is a hepatocyte. In some embodiments, the hepatocyte is within the liver of a human, a non-human primate, or a mouse.

In some embodiments, the polynucleotide is introduced into the eukaryotic cell by an mRNA or a recombinant virus. In one such embodiment, the mRNA is packaged within a lipid nanoparticle. In another such an embodiment, the recombinant virus is a recombinant adenovirus, a recombinant lentivirus, a recombinant retrovirus, or a recombinant AAV. In a particular embodiment, the recombinant virus is a recombinant AAV.

In another aspect, the invention provides a method for producing a genetically-modified eukaryotic cell comprising a modified TTR gene, the method comprising introducing into an eukaryotic cell (a) a polynucleotide comprising a nucleic acid sequence encoding an engineered nuclease having specificity for a recognition sequence within a TTR gene, wherein said engineered nuclease is expressed in the eukaryotic cell, or (b) the engineered nuclease having specificity for a recognition sequence within a TTR gene, wherein the engineered nuclease produces a cleavage site within the recognition sequence and generates a modified TTR gene that does not encode a full-length endogenous TTR polypeptide.

In some embodiment, the modified TTR gene comprises an insertion or deletion within exon 1 or exon 3.

In some embodiments the insertion or deletion is introduced at the engineered nuclease cleavage site.

In some embodiments, the engineered nuclease is an engineered nuclease having specificity for a recognition sequence comprising SEQ ID NO: 7 or 9. In certain embodiments, the engineered nuclease has specificity for a recognition sequence comprising SEQ ID NO: 7. In other embodiments, the engineered nuclease has specificity for a recognition sequence comprising SEQ ID NO: 9.

In some embodiments, the engineered nuclease is any engineered meganuclease of the invention.

In some embodiments, the method is effective to reduce TTR polypeptide levels in the cell by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or more, relative to a reference level. In some embodiments, the TTR polypeptide levels are reduced by about 1%-5%, 5%-10%, 10%-20%, 20%-30%, 30%-40%, 40%-50%, 50%-60%, 60%-70%, 70%-80%, or more, relative to a reference level.

In some embodiments, the eukaryotic cell is a mammalian cell. In some embodiments, the mammalian cell is selected from a human cell, a non-human primate cell, or a mouse cell. In particular embodiments, the mammalian cell is a liver cell, such as a hepatocyte. In some embodiments, the liver cell or hepatocyte is within the liver of a human, a non-human primate, or a mouse. In some embodiments, the liver cell is a liver progenitor cell or stem cell.

In some embodiments, the method is performed in vitro. In some embodiments, the method is performed in vivo.

In some embodiments, the polynucleotide is a recombinant DNA construct.

In some embodiments, the polynucleotide is introduced into said eukaryotic cell by a lipid nanoparticle.

In some embodiments, the polynucleotide is introduced into the eukaryotic cell by an mRNA or a recombinant virus. In one such embodiment, the mRNA is packaged within a lipid nanoparticle. In another such an embodiment, the recombinant virus is a recombinant adenovirus, a recombinant lentivirus, a recombinant retrovirus, or a recombinant AAV. In a particular embodiment, the recombinant virus is a recombinant AAV.

In another aspect, the invention provides a genetically-modified eukaryotic cell prepared by any method of the invention.

In another aspect, the invention provides a genetically-modified eukaryotic cell comprising a modified TTR gene, wherein the modified TTR gene comprises an insertion or deletion at an engineered meganuclease cleavage site within SEQ ID NO: 7 or SEQ ID NO: 9, and wherein said modified TTR gene does not encode a full-length endogenous TTR polypeptide.

In some embodiments, the genetically-modified eukaryotic cell has a reduction in TTR polypeptide levels of at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or more, relative to a reference level. In some embodiments, the TTR polypeptide levels are reduced by about 1%-5%, 5%-10%, 10%-20%, 20%-30%, 30%-40%, 40%-50%, 50%-60%, 60%-70%, 70%-80%, or more, relative to a reference level.

In some embodiments, the eukaryotic cell is a mammalian cell. In some embodiments, the mammalian cell is selected from a human cell, a non-human primate cell, or a mouse cell. In particular embodiments, the mammalian cell is a liver cell such as a hepatocyte. In some embodiments, the liver cell or hepatocyte is within the liver of a human, a non-human primate, or a mouse. In some embodiments, the liver cell is a liver progenitor cell or stem cell.

In another aspect, the invention provides a genetically-modified eukaryotic cell within the liver of a primate comprising a modified TTR gene, wherein the modified TTR gene comprises an insertion or deletion within exon 1 or exon 3, and wherein said modified TTR gene does not encode a full-length endogenous TTR polypeptide.

In some embodiments, the insertion or deletion is positioned at an engineered nuclease cleavage site. In some embodiments, the insertion or deletion is within exon 3. In certain embodiments, the engineered nuclease cleavage site is within an engineered meganuclease recognition sequence comprising SEQ ID NO: 7.

In some embodiments, the insertion or deletion is within exon 1. In certain embodiments, the engineered nuclease cleavage site is within an engineered meganuclease recognition sequence comprising SEQ ID NO: 9.

In some embodiments, the genetically-modified eukaryotic cell has a reduction in TTR polypeptide levels of at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or more, relative to a reference level. In some embodiments, the TTR polypeptide levels are reduced by about 1-5%, 5%-10%, 10%-20%, 20%-30%, 30%-40%, 40%-50%, 50%-60%, 60%-70%, 70%-80%, or more, relative to a reference level.

In some embodiments, the genetically-modified eukaryotic cell is a mammalian cell. In some embodiments, the mammalian cell is selected from a human cell, a non-human primate cell, or a mouse cell. In particular embodiments, the mammalian cell is a liver cell such as a hepatocyte. In some embodiments, the liver cell or hepatocyte is within the liver of a human, a non-human primate, or a mouse. In some embodiments, the liver cell is a liver progenitor cell or stem cell.

In some embodiments, the genetically-modified eukaryotic cell comprises a polynucleotide comprising a nucleic acid sequence encoding an engineered meganuclease described herein.

In another aspect, the invention provides a pharmaceutical composition comprising a pharmaceutically acceptable carrier and any engineered meganuclease of the invention, or a polynucleotide comprising a nucleic acid sequence encoding any such engineered meganuclease.

In some embodiments, the polynucleotide is an mRNA. In one such embodiment, the mRNA is packaged within a lipid nanoparticle.

In some embodiments of the pharmaceutical composition, the pharmaceutical composition comprises a recombinant DNA construct comprising the polynucleotide.

In some embodiments, the pharmaceutical composition comprises a recombinant virus comprising the polynucleotide. In some such embodiments, the recombinant virus is a recombinant adenovirus, a recombinant lentivirus, a recombinant retrovirus, or a recombinant AAV. In a particular embodiment, the recombinant virus is a recombinant AAV.

In some embodiments, the pharmaceutical composition comprises a lipid nanoparticle composition comprising lipid nanoparticles comprising a polynucleotide comprising a nucleic acid sequence encoding an engineered meganuclease described herein. In some embodiments, the polynucleotide is an mRNA.

In some embodiments, the pharmaceutical composition comprises about $1\times10^{10}$ gc/kg to about $1\times10^{14}$ gc/kg (e.g., $1\times10^{10}$ gc/kg, $1\times10^{11}$ gc/kg, $1\times10^{12}$ gc/kg, $1\times10^{13}$ gc/kg, or $1\times10^{14}$ gc/kg) of the polynucleotide comprising the nucleic acid sequence encoding the engineered meganuclease. In some embodiments, the pharmaceutical composition comprises at least about $1\times10^{10}$ gc/kg, at least about $1\times10^{11}$ gc/kg, at least about $1\times10^{12}$ gc/kg, at least about $1\times10^{13}$ gc/kg, or at least about $1\times10^{14}$ gc/kg of the polynucleotide comprising the nucleic acid sequence encoding the engineered meganuclease. In some embodiments, the pharmaceutical composition comprises about $1\times10^{10}$ gc/kg to about $1\times10^{11}$ gc/kg, about $1\times10^{11}$ gc/kg to about $1\times10^{12}$ gc/kg, about $1\times10^{12}$ gc/kg to about $1\times10^{13}$ gc/kg, or about $1\times10^{13}$ gc/kg to about $1\times10^{14}$ gc/kg of the polynucleotide comprising the nucleic acid sequence encoding the engineered meganuclease. In certain embodiments, the pharmaceutical composition comprises about $1\times10^{12}$ gc/kg to about $9\times10^{13}$ gc/kg (e.g., about $1\times10^{12}$ gc/kg, about $2\times10^{12}$ gc/kg, about $3\times10^{12}$ gc/kg, about $4\times10^{12}$ gc/kg, about $5\times10^{12}$ gc/kg, about $6\times10^{12}$ gc/kg, about $7\times10^{12}$ gc/kg, about $8\times10^{12}$ gc/kg, about $9\times10^{12}$ gc/kg, about $1\times10^{13}$ gc/kg, about $2\times10^{13}$ gc/kg, about $3\times10^{13}$ gc/kg, about $4\times10^{13}$ gc/kg, about $5\times10^{13}$ gc/kg, about $6\times10^{13}$ gc/kg, about $7\times10^{13}$ gc/kg, about $8\times10^{13}$ gc/kg, or about $9\times10^{13}$ gc/kg) of the polynucleotide comprising the nucleic acid sequence encoding the engineered meganuclease.

In some embodiments of the pharmaceutical composition, the pharmaceutical composition is for treatment of a subject having transthyretin amyloidosis (ATTR).

In another aspect, the invention provides a method for reducing TTR levels in a subject, the method comprising delivering to a target cell in the subject any engineered meganuclease of the invention, or a polynucleotide comprising a nucleic acid sequence encoding the engineered meganuclease, wherein the method is effective to reduce TTR levels in the subject relative to a reference level.

In some embodiments of the method, the target cell is a mammalian cell. In some embodiments, the mammalian cell is selected from a human cell, a non-human primate cell, or a mouse cell. In particular embodiments, the mammalian cell is a hepatocyte. In some embodiments, the hepatocyte is within the liver of a human, a non-human primate, or a mouse.

In some embodiments, the polynucleotide is an mRNA. In some embodiments, the polynucleotide is DNA.

In some embodiments, the polynucleotide is encapsulated in a lipid nanoparticle and the lipid nanoparticle is delivered to the target cell in the subject.

In some embodiments, the polynucleotide is delivered to the target cell using a recombinant virus comprising the polynucleotide. In some such embodiments, the recombinant virus is a recombinant adenovirus, a recombinant lentivirus, a recombinant retrovirus, or a recombinant AAV. In a particular embodiment, the recombinant virus is a recombinant AAV.

In some embodiments, about $1\times10^{10}$ gc/kg to about $1\times10^{14}$ gc/kg (e.g., $1\times10^{10}$ gc/kg, $1\times10^{11}$ gc/kg, $1\times10^{12}$ gc/kg, $1\times10^{13}$ gc/kg, or $1\times10^{14}$ gc/kg) of the polynucleotide comprising the nucleic acid sequence encoding the engineered meganuclease is administered to the subject. In some embodiments, at least about $1\times10^{10}$ gc/kg, at least about $1\times10^{11}$ gc/kg, at least about $1\times10^{12}$ gc/kg, at least about $1\times10^{13}$ gc/kg, or at least about $1\times10^{14}$ gc/kg of the polynucleotide comprising the nucleic acid sequence encoding the engineered meganuclease is administered to the subject. In some embodiments, about $1\times10^{10}$ gc/kg to about $1\times10^{11}$ gc/kg, about $1\times10^{11}$ gc/kg to about $1\times10^{12}$ gc/kg, about $1\times10^{12}$ gc/kg to about $1\times10^{13}$ gc/kg, or about $1\times10^{13}$ gc/kg to about $1\times10^{14}$ gc/kg of the polynucleotide comprising the nucleic acid sequence encoding the engineered meganuclease is administered to the subject. In certain embodiments, about $1\times10^{12}$ gc/kg to about $9\times10^{13}$ gc/kg (e.g., about $1\times10^{12}$ gc/kg, about $2\times10^{12}$ gc/kg, about $3\times10^{12}$ gc/kg, about $4\times10^{12}$ gc/kg, about $5\times10^{12}$ gc/kg, about $6\times10^{12}$ gc/kg, about $7\times10^{12}$ gc/kg, about $8\times10^{12}$ gc/kg, about $9\times10^{12}$ gc/kg, about $1\times10^{13}$ gc/kg, about $2\times10^{13}$ gc/kg, about $3\times10^{13}$ gc/kg, about $4\times10^{13}$ gc/kg, about $5\times10^{13}$ gc/kg, about $6\times10^{13}$ gc/kg, about $7\times10^{13}$ gc/kg, about $8\times10^{13}$ gc/kg, or about $9\times10^{13}$ gc/kg) of polynucleotide comprising the nucleic acid sequence encoding the engineered meganuclease is administered to the subject.

In some embodiments, circulating TTR levels are reduced in the subject relative to a reference control.

In some embodiments, the levels in one or more organs of the subject are reduced. In some embodiments, the organ comprises the brain, the heart, the kidneys, the eyes, the large intestine, the small intestine, the liver, or combinations thereof.

In some embodiments, TTR levels are reduced in one or more tissues of the subject relative to a reference control. In some embodiments, the tissue comprises a nerve tissue, a muscle tissue, a connective tissue, or a tissue of the meninges, or a combination thereof.

In some such embodiments, the level of TTR is reduced by about 10% to about 80% relative to a reference control. In some embodiments, the level of TTR is reduced by about 10%-20%, 20%-30%, 30%-40%, 40%-50%, 50%-60%, 60%-70%, 70%-80%, or more, relative to a reference level. In some such embodiments, the level of TTR is reduced by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or more, relative to a reference level.

In some embodiments, TTR amyloid formation is reduced in the subject relative to a reference control. In some embodiments, TTR amyloid formation is reduced by about 10% to about 100% relative to a reference control. In some embodiments, TTR amyloid formation is reduced by about 10%-20%, 20%-30%, 30%-40%, 40%-50%, 50%-60%, 60-70%, 70%-80%, 80%-90%, or 90%-100% relative to a reference level. In some embodiments, TTR amyloid formation is reduced by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, or about 100% relative to a reference level.

In another aspect, the invention provides a method for treating TTR amyloidosis or a TTR-associated disease in a subject in need thereof, said method comprising delivering to a target cell in said subject a polynucleotide comprising a nucleic acid sequence encoding an engineered meganuclease described herein, wherein said engineered meganuclease is expressed in said target cell, and wherein said engineered meganuclease produces a cleavage site in a TTR gene at a recognition sequence comprising SEQ ID NO: 7 or SEQ ID NO: 9, and wherein expression of said TTR gene is disrupted by non-homologous end-joining at said cleavage site.

In some embodiments, the method comprises administering to the subject an effective amount of any pharmaceutical composition of the invention.

In some embodiments, the method produces a modified TTR gene in the target cell that does not encode a full-length endogenous TTR polypeptide. In some embodiments, expression of a full-length endogenous TTR protein by the target cell is reduced compared to a control cell. In some embodiments, expression of full-length endogenous TTR protein is reduced in the subject relative to a control subject.

In some embodiments of the method, the target cell is a mammalian cell. In some embodiments, the mammalian cell is selected from a human cell, a non-human primate cell, or a mouse cell. In particular embodiments, the mammalian cell is a liver cell such as a hepatocyte. In some embodiments, the hepatocyte is within the liver of a human, a non-human primate, or a mouse. In some embodiments, the liver cell is a liver progenitor cell or stem cell.

In some embodiments, the polynucleotide is an mRNA. In some embodiments, the polynucleotide is DNA (i.e., a recombinant DNA construct).

In some embodiments, the polynucleotide is encapsulated in a lipid nanoparticle and the lipid nanoparticle is delivered to the target cell in the subject.

In some embodiments, the polynucleotide is delivered to the target cell with a recombinant virus comprising the polynucleotide. In some such embodiments, the recombinant virus is a recombinant adenovirus, a recombinant lentivirus, a recombinant retrovirus, or a recombinant AAV. In a particular embodiment, the recombinant virus is a recombinant AAV.

In some embodiments, the method is effective to reduce TTR levels in the subject relative to a reference level.

In some embodiments, circulating TTR levels are reduced in the subject relative to a reference control.

In some embodiments, TTR levels in one or more organs of the subject are reduced relative to a reference control. In some embodiments, the organ comprises the brain, the heart, the kidneys, the eyes, the large intestine, the small intestine, the liver, or combinations thereof.

In some embodiments, TTR levels are reduced in one or more tissues of the subject relative to a reference control. In some embodiments, the tissue comprises a nerve tissue, a muscle tissue, a connective tissue, or a tissue of the meninges, or a combination thereof.

In some such embodiments, the level of TTR is reduced by about 10% to about 80% relative to a reference control. In some embodiments, the level of TTR is reduced by about 10%-20%, 20%-30%, 30%-40%, 40%-50%, 50%-60%, 60%-70%, or 70%-80%, relative to a reference level. In some such embodiments, the level of TTR is reduced by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, or more, relative to a reference level.

In some embodiments, TTR amyloid formation is reduced in the subject relative to a reference control. In some embodiments, TTR amyloid formation is reduced by about 10% to about 100% relative to a reference control. In some embodiments, TTR amyloid formation is reduced by about 10%-20%, 20%-30%, 30%-40%, 40%-50%, 50%-60%, 60-70%, 70%-80%, 80%-90%, or 90%-100% relative to a reference level. In some embodiments, TTR amyloid formation is reduced by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, or about 100% relative to a reference level.

In some embodiments, the subject is a human subject.

In some embodiments, the subject has a mutation in a TTR gene that affects one or more tissues comprising the peripheral nervous system, the autonomic nervous system, the leptomeninges, or the heart.

In some embodiments, the subject has a mutation in a TTR gene encoding a TTR polypeptide comprising Gly6Ser, Cys10Arg, Leu12Pro, Asp18Gly, Val20Ile, Ala25Thr, Val30Met, Val30Ala, Val30Leu, Val30Gly, Phe33Ile, Phe33Leu, Ala36Pro, Glu42Gly, Phe44Ser, Ala45Thr, Gly47Arg, Gly47Ala, Gly47Arg, Thr49Ala, Ser50Arg, Ser50Ile, Gly53Glu, Leu55Pro, Leu58His, Leu58Arg, Thr60Ala, Glu61Lys, Phe64Leu, Phe64Ser, Ile68Leu, Tyr69His, Lys70Asn, Val71Ala, Ser77Tyr, Ile84Ser, Glu89Gln, His90Asn, Ala97Gly, Ala97Ser, Arg104His, Ile107Val, Ala109Thr, Ala109Val, Leu111Met, Tyr114Cys, Tyr114His, Tyr116Val, Thr119Met, Val122Ile, Val122Del, or combinations thereof.

In another aspect, the invention provides an engineered meganuclease described herein for use as a medicament. The invention further provides the use of an engineered meganuclease, described herein in the manufacture of a medicament for treating a disease in a subject in need thereof (e.g., a subject having transthyretin amyloidosis) and/or for reducing the level of TTR in a subject.

In another aspect, the invention provides a polynucleotide for use as a medicament, wherein the polynucleotide comprises a nucleic acid sequence encoding an engineered meganuclease disclosed herein. The invention further provides the use of a polynucleotide in the manufacture of a medicament for treating a disease in a subject in need thereof (e.g., a subject having transthyretin amyloidosis) and/or for reducing the level of TTR in a subject.

In another aspect, the invention provides a method for modifying a TTR gene in a target cell in a subject, wherein the method comprises delivering to a target cell: (a) a polynucleotide comprising a nucleic acid sequence encoding an engineered meganuclease described herein, wherein the engineered meganuclease is expressed in the target cell; or (b)

an engineered meganuclease described herein; wherein the engineered meganuclease produces a cleavage site in the TTR gene at a recognition sequence comprising SEQ ID NO: 7 or SEQ ID NO: 9 and generates a modified TTR gene in the target cell.

In some embodiments, the cleavage site is repaired by non-homologous end joining, and wherein the modified TTR gene comprises an insertion or deletion that disrupts expression of the encoded TTR protein.

In some embodiments, the modified TTR gene does not encode a full-length endogenous TTR protein.

In some embodiments, expression of a full-length endogenous TTR protein by the target cell is reduced compared to a control cell.

In some embodiments, expression of full-length endogenous TTR protein is reduced in the subject relative to a control subject.

In some embodiments, the subject is a mammal.

In some embodiments, the target cell is a liver cell. In some embodiments, the target cell is a liver progenitor cell or stem cell.

In some embodiments, the subject is a human.

In some embodiments, the polynucleotide is an mRNA, such as an mRNA described herein.

In some embodiments, the polynucleotide is a recombinant DNA construct, such as a recombinant DNA construct described herein.

In some embodiments, the polynucleotide is delivered to the target cell by a lipid nanoparticle.

In some embodiments, the polynucleotide is delivered to the target cell by a recombinant virus, such as any recombinant virus described herein.

In some embodiments, the target cell comprising the modified TTR gene comprises reduced levels of a full-length endogenous TTR protein compared to a control cell.

In some embodiments, the subject comprises reduced serum levels of a full-length endogenous TTR protein compared to a control subject following modification of the TTR gene in the target cell.

In some embodiments, the subject exhibits a reduction in one or more symptoms of ATTR or a TTR-associated disease compared to a control subject following modification of the TTR gene in the target cell.

In some embodiments, the subject has a mutation in a TTR gene that affects one or more tissues comprising the peripheral nervous system, the autonomic nervous system, the leptomeninges, or the heart.

In some embodiments, the subject has a mutation in a TTR gene comprising Gly6Ser, Cys10Arg, Leu12Pro, Asp18Gly, Val20Ile, Ala25Thr, Val30Met, Val30Ala, Val30Leu, Val30Gly, Phe33Ile, Phe33Leu, Ala36Pro, Glu42Gly, Phe44Ser, Ala45Thr, Gly47Arg, Gly47Ala, Gly47Arg, Thr49Ala, Ser50Arg, Ser50Ile, Gly53Glu, Leu55Pro, Leu58His, Leu58Arg, Thr60Ala, Glu61Lys, Phe64Leu, Phe64Ser, Ile68Leu, Tyr69His, Lys70Asn, Val71Ala, Ser77Tyr, Ile84Ser, Glu89Gln, His90Asn, Ala97Gly, Ala97Ser, Arg104His, Ile107Val, Ala109Thr, Ala109Val, Leu111Met, Tyr114Cys, Tyr114His, Tyr116Val, Thr119Met, Val122Ile, Val122Del, or combinations thereof.

BRIEF DESCRIPTION OF THE FIGURES

FIG. 1. TTR 15-16 recognition sequence in the human TTR gene. The TTR 15-16 recognition sequence targeted by recombinant meganucleases of the invention comprises two recognition half-sites. Each recognition half-site comprises 9 base pairs, separated by a 4 base pair central sequence. The TTR 15-16 recognition sequence (SEQ ID NO: 7) spans nucleotides 3,377 to 3,398 of the human TTR gene (SEQ ID NO: 3) and comprises two recognition half-sites referred to as TTR15-16 (1) and TTR15-16 (2).

FIG. 2. TTR 5-6 recognition sequence in the human TTR gene. The TTR 5-6 recognition sequence targeted by recombinant meganucleases of the invention comprises two recognition half-sites. Each recognition half-site comprises 9 base pairs, separated by a 4 base pair central sequence. The TTR 5-6 recognition sequence (SEQ ID NO: 9) spans nucleotides 170 to 191 of the human TTR gene (SEQ ID NO: 3) and comprises two recognition half-sites referred to as TTR5-6 (1) and TTR5-6 (2).

FIGS. 4A-4B. FIG. 4A provides the sequence of the TTR 5-6L.1204 meganuclease. FIG. 4B is a multi-sequence alignment between the TTR 15-16L.164, TTR 15-16L.161, TTR 15-16x.81, and TTR 15-16L.181 meganucleases. Asterisks indicate conserved residues amongst all aligned nucleases, and a space indicates that at least one amino acid differed amongst the meganucleases.

FIG. 6A shows results using a human recognition sequence and FIG. 6B shows results using a model NHP recognition sequence.

In FIG. 10A the gray and black bars indicate indels measured at day 1 (D1) and day 7 (D7) post transfection, respectively. In FIG. 10B, the bars indicate indels measured at D7 at the indicated concentration of administered meganuclease.

FIG. 14C provides the percentage of indels of d18, which represents the same data shown in FIG. 14B and at day 128 (d128) post-AAV administration assessed by ddPCR at two different doses ($6\times10^{12}$ [animals 1305048 and 1404128] and $3\times10^{13}$ GC/kg [animals 1305168 and T1466224]).

BRIEF DESCRIPTION OF THE SEQUENCES

Figure 3:
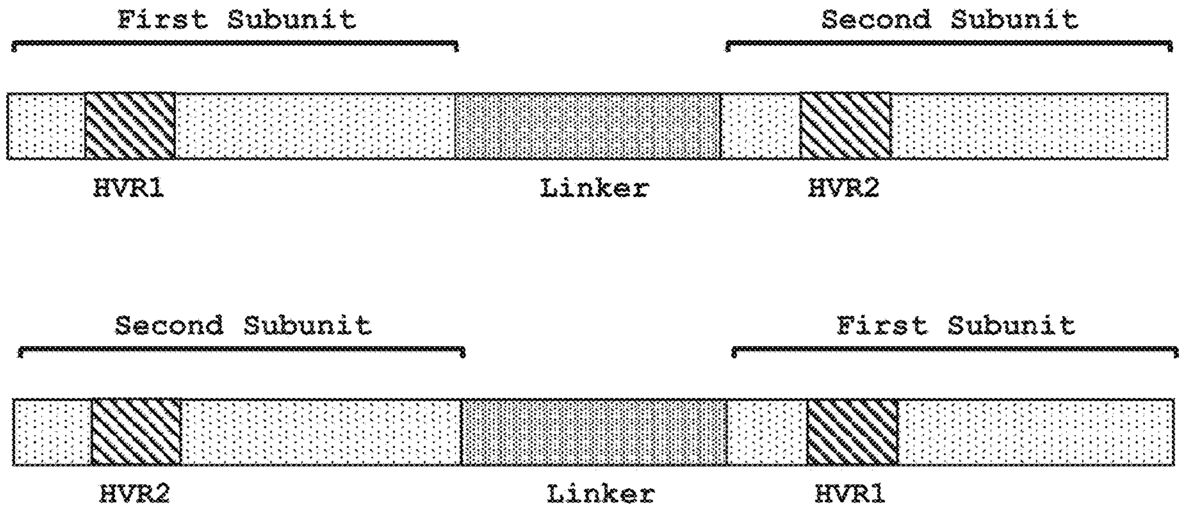
FIG. 3. The recombinant meganucleases described herein comprise two subunits, wherein the first subunit comprising the HVR1 region binds to a first recognition half-site (e.g., TTR5-6 (1)) and the second subunit comprising the HVR2 region binds to a second recognition half-site (e.g., TTR5-6 (2)). In embodiments where the recombinant meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.

SEQ ID NO: 1 sets forth the amino acid sequence of the wild-type I-CreI meganuclease from *Chlamydomonas reinhardtii.*

SEQ ID NO: 2 sets forth the amino acid sequence of the LAGLIDADG motif.

SEQ ID NO: 3 sets forth the nucleic acid sequence of the human TTR gene sequence (NCBI GENE ID: 7276).

SEQ ID NO: 4 sets forth the amino acid sequence of the human TTR protein sequence.

SEQ ID NO: 5 sets forth the amino acid sequence of the mature human TTR protein sequence (a 127 Amino acid processed protein without the first 20 amino acids that are part of the pre-segment).

SEQ ID NO: 6 sets forth the amino acid sequence of the mature human TTR protein sequence having the amino acid substitution V30M.

SEQ ID NO: 7 sets forth the nucleic acid sequence of the sense strand of the TTR 15-16 recognition sequence.

SEQ ID NO: 8 sets forth the nucleic acid sequence of the antisense strand of the TTR 15-16 recognition sequence.

SEQ ID NO: 9 sets forth the nucleic acid sequence of the sense strand of the TTR 5-6 recognition sequence.

SEQ ID NO: 10 sets forth the nucleic acid sequence of the antisense strand of the TTR 5-6 recognition sequence.

SEQ ID NO: 11 sets forth the amino acid sequence of the TTR 15-16x.81 meganuclease.

SEQ ID NO: 12 sets forth the amino acid sequence of the TTR 15-16L.161 meganuclease.

SEQ ID NO: 13 sets forth the amino acid sequence of the TTR 15-16L.164 meganuclease.

SEQ ID NO: 14 sets forth the amino acid sequence of the TTR 15-16L.181 meganuclease.

SEQ ID NO: 15 sets forth the amino acid sequence of the TTR 5-6L.1204 meganuclease.

SEQ ID NO: 16 sets forth the amino acid sequence of the TTR 15-16x.81 meganuclease TTR15-binding subunit.

SEQ ID NO: 17 sets forth the amino acid sequence of the TTR 15-16L.161 meganuclease TTR15-binding subunit.

SEQ ID NO: 18 sets forth the amino acid sequence of the TTR 15-16L.164 meganuclease TTR15-binding subunit.

SEQ ID NO: 19 sets forth the amino acid sequence of the TTR 15-16L.181 meganuclease TTR15-binding subunit.

SEQ ID NO: 20 sets forth the amino acid sequence of the TTR 15-16x.81 meganuclease TTR16-binding subunit.

SEQ ID NO: 21 sets forth the amino acid sequence of the TTR 15-16L.161 meganuclease TTR16-binding subunit.

SEQ ID NO: 22 sets forth the amino acid sequence of the TTR 15-16L.164 meganuclease TTR16-binding subunit.

SEQ ID NO: 23 sets forth the amino acid sequence of the TTR 15-16L.181 meganuclease TTR16-binding subunit.

SEQ ID NO: 24 sets forth the amino acid sequence of the TTR 5-6L.1204 meganuclease TTR5-binding subunit.

SEQ ID NO: 25 sets forth the amino acid sequence of the TTR 5-6L.1204 meganuclease TTR6-binding subunit.

SEQ ID NO: 26 sets forth the nucleic acid sequence of the sense strand of the TTR 15 half-site recognition sequence.

SEQ ID NO: 27 sets forth the nucleic acid sequence of the anti-sense strand of the TTR 15 half-site recognition sequence.

SEQ ID NO: 28 sets forth the nucleic acid sequence of the sense strand of the TTR 16 half-site recognition sequence.

SEQ ID NO: 29 sets forth the nucleic acid sequence of the sense anti-sense strand of the TTR 16 half-site recognition sequence.

SEQ ID NO: 30 sets forth the nucleic acid sequence of the sense strand of the TTR 5 half-site recognition sequence.

SEQ ID NO: 31 sets forth the nucleic acid sequence of the anti-sense strand of the TTR 5 half-site recognition sequence.

SEQ ID NO: 32 sets forth the nucleic acid sequence of the sense strand of the TTR 6 half-site recognition sequence.

SEQ ID NO: 33 sets forth the nucleic acid sequence of the sense anti-sense strand of the TTR 6 half-site recognition sequence.

SEQ ID NO: 34 sets forth the TTR 5-6 model NHP recognition sequence used in the GFP reporter assay of Examples 1 and 3.

SEQ ID NO: 35 sets forth the nucleic acid sequence of an artificial probe used in digital PCR assay for assessing indel % at the TTR 5-6 site in human cells.

SEQ ID NO: 36 sets forth the nucleic acid sequence of an artificial forward primer used in digital PCR assay for assessing indel % at the TTR 5-6 site in human cells.

SEQ ID NO: 37 sets forth the nucleic acid sequence of an artificial reverse primer used in digital PCR assay for assessing indel % at the TTR 5-6 site in human cells.

SEQ ID NO: 38 sets forth the nucleic acid sequence of an artificial probe used in digital PCR assay for a reference level in assessing indel % for the TTR 5-6 site in human cells.

SEQ ID NO: 39 sets forth the nucleic acid sequence of an artificial forward primer used in digital PCR assay for a reference level in assessing indel % for the TTR 5-6 site in human cells.

SEQ ID NO: 40 sets forth the nucleic acid sequence of an artificial reverse primer used in digital PCR assay for a reference level in assessing indel % for the TTR 5-6 site in human cells.

SEQ ID NO: 41 sets forth the nucleic acid sequence of an artificial probe used in digital PCR assay for assessing indel % at the TTR 15-16 site in human cells.

SEQ ID NO: 42 sets forth the nucleic acid sequence of an artificial forward primer used in digital PCR assay for assessing indel % at the TTR 15-16 site in human cells.

SEQ ID NO: 43 sets forth the nucleic acid sequence of an artificial reverse primer used in digital PCR assay for assessing indel % at the TTR 15-16 site in human cells.

SEQ ID NO: 44 sets forth the nucleic acid sequence of an artificial probe used in digital PCR assay for a reference level in assessing indel % for the TTR 15-16 site in human cells.

SEQ ID NO: 45 sets forth the nucleic acid sequence of an artificial forward primer used in digital PCR assay for a reference level in assessing indel % for the TTR 15-16 site in human cells.

SEQ ID NO: 46 sets forth the nucleic acid sequence of an artificial reverse primer used in digital PCR assay for a reference level in assessing indel % for the TTR 15-16 site in human cells.

SEQ ID NO: 47 sets forth the nucleic acid sequence of an artificial forward primer used in digital PCR assay for a reference level in assessing indel % for the TTR 5-6 site in mouse cells.

SEQ ID NO: 48 sets forth the nucleic acid sequence of an artificial reverse primer used in digital PCR assay for a reference level in assessing indel % for the TTR 5-6 site in mouse cells.

SEQ ID NO: 49 sets forth the nucleic acid sequence of an artificial probe used in digital PCR assay for assessing indel % at the TTR 5-6 site in mouse cells.

SEQ ID NO: 50 sets forth the nucleic acid sequence of an artificial probe used in digital PCR assay for a reference level in assessing indel % for the TTR 5-6 site in mouse cells.

SEQ ID NO: 51 sets forth the nucleic acid sequence of an artificial forward primer used in digital PCR assay for assessing indel % for the TTR 5-6 site in non-human primates.

SEQ ID NO: 52 sets forth the nucleic acid sequence of an artificial reverse primer used in digital PCR assay for assessing indel % for the TTR 5-6 site in non-human primates.

SEQ ID NO: 53 sets forth the nucleic acid sequence of an artificial probe used in digital PCR assay for assessing indel % at the TTR 5-6 site in non-human primates.

SEQ ID NO: 54 sets forth the nucleic acid sequence of an artificial forward primer used in digital PCR assay for assessing indel % for the TTR 5-6 site in non-human primates.

SEQ ID NO: 55 sets forth the nucleic acid sequence of an artificial reverse primer used in digital PCR assay for assessing indel % for the TTR 5-6 site in non-human primates.

SEQ ID NO: 56 sets forth the nucleic acid sequence of an artificial probe used in digital PCR assay for assessing indel % at the TTR 5-6 site in non-human primates.

SEQ ID NO: 57 sets forth the nucleic acid sequence of an artificial forward primer used in digital PCR assay for assessing AAV copy number in non-human primates transduced with an AAV encoding the TTR 5-6L.1204 or TTR 15-16x.81 meganucleases.

SEQ ID NO: 58 sets forth the nucleic acid sequence of an artificial reverse primer used in digital PCR assay for a reference level in assessing AAV copy number in non-human primates transduced with an AAV encoding the TTR 5-6L.1204 or TTR 15-16x.81 meganucleases.

SEQ ID NO: 59 sets forth the nucleic acid sequence of an artificial probe used in digital PCR assay for assessing AAV copy number in non-human primates transduced with an AAV encoding the TTR 5-6L.1204 or TTR 15-16x.81 meganucleases.

SEQ ID NO: 60 sets forth the nucleic acid sequence of an artificial forward primer used in digital PCR assay for a reference level in assessing AAV copy number in non-human primates transduced with an AAV encoding the TTR 5-6L.1204 or TTR 15-16x.81 meganucleases.

SEQ ID NO: 61 sets forth the nucleic acid sequence of an artificial reverse primer used in digital PCR assay for a reference level in assessing AAV copy number in non-human primates transduced with an AAV encoding the TTR 5-6L.1204 or TTR 15-16x.81 meganucleases.

SEQ ID NO: 62 sets forth the nucleic acid sequence of an artificial probe used in digital PCR assay for assessing AAV copy number in non-human primates transduced with an AAV encoding the TTR 5-6L.1204 or TTR 15-16x.81 meganucleases.

SEQ ID NO: 63 sets forth the nucleic acid sequence of an artificial forward primer used in digital PCR assay for assessing indel % for the TTR 15-16 site in non-human primates.

SEQ ID NO: 64 sets forth the nucleic acid sequence of an artificial reverse primer used in digital PCR assay for assessing indel % for the TTR 15-16 site in non-human primates.

SEQ ID NO: 65 sets forth the amino acid sequence of a polypeptide linker.

SEQ ID NO: 66 sets forth the amino acid sequence of the TTR 15-16x.81 meganuclease.

SEQ ID NO: 67 sets forth the amino acid sequence of the TTR 15-16L.161 meganuclease.

SEQ ID NO: 68 sets forth the amino acid sequence of the TTR 15-16L.164 meganuclease.

SEQ ID NO: 69 sets forth the amino acid sequence of the TTR 15-16L.181 meganuclease.

SEQ ID NO: 70 sets forth the amino acid sequence of the TTR 5-6L.1204 meganuclease.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" are used interchangeably to refer to naturally-occurring or engineered enzymes, which cleave a phosphodiester bond within a polynucleotide chain.

As used herein, the terms "cleave" or "cleavage" refer to the hydrolysis of phosphodiester bonds within the backbone of a recognition sequence within a target sequence that results in a double-stranded break within the target sequence, referred to herein as a "cleavage site".

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI (SEQ ID NO: 1), and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in the targeted cells as described herein such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will bind non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two nuclease subunits into a single polypeptide. A linker may have a sequence that is found in natural proteins or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. Nos. 8,445,251, 9,340,777, 9,434,931, and 10,041,053, each of which is incorporated by reference in its entirety. In some embodiments, a linker may have at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 65, which sets forth residues 154-195 of any one of SEQ ID NOs: 11-15. In some embodiments, a linker may have an amino acid sequence comprising SEQ ID NO:51, which sets forth residues 154-195 of any one of SEQ ID NOs: 11-15.

As used herein, the terms "recombinant" or "engineered," with respect to a protein, means having an altered amino acid sequence as a result of the application of genetic engineering techniques to nucleic acids that encode the protein and cells or organisms that express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation, and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant or engineered.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein, the term with respect to recombinant proteins, the term "modification" means any insertion, deletion, or substitution of an amino acid residue in the recombinant sequence relative to a reference sequence (e.g., a wild-type or a native sequence).

As used herein, the terms "recognition sequence" or "recognition site" refers to a DNA sequence that is bound and cleaved by a nuclease. In the case of a meganuclease, a recognition sequence comprises a pair of inverted, 9 basepair "half sites," which are separated by four basepairs. In the case of a single-chain meganuclease, the N-terminal domain of the protein contacts a first half-site and the C-terminal domain of the protein contacts a second half-site. Cleavage by a meganuclease produces four basepair 3' overhangs. "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence.

As used herein, the terms "target site" or "target sequence" refers to a region of the chromosomal DNA of a cell comprising a recognition sequence for a nuclease.

As used herein, the terms "DNA-binding affinity" or "binding affinity" means the tendency of a nuclease to non-covalently associate with a reference DNA molecule (e.g., a recognition sequence or an arbitrary sequence). Binding affinity is measured by a dissociation constant, Kd. As used herein, a nuclease has "altered" binding affinity if the Kd of the nuclease for a reference recognition sequence is increased or decreased by a statistically significant percent change relative to a reference nuclease.

As used herein, the term "specificity" means the ability of a nuclease to bind and cleave double-stranded DNA molecules only at a particular sequence of base pairs referred to as the recognition sequence, or only at a particular set of recognition sequences. The set of recognition sequences will share certain conserved positions or sequence motifs but may be degenerate at one or more positions. A highly-specific nuclease is capable of cleaving only one or a very few recognition sequences. Specificity can be determined by any method known in the art.

As used herein, the term "homologous recombination" or "HR" refers to the natural, cellular process in which a double-stranded DNA-break is repaired using a homologous DNA sequence as the repair template (see, e.g. Cahill et al. (2006), Front. Biosci. 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), Front. Biosci. 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases can be used to effectively knock-out a gene in a population of cells.

As used herein, the term "homology arms" or "sequences homologous to sequences flanking a nuclease cleavage site" refer to sequences flanking the 5' and 3' ends of a nucleic acid molecule, which promote insertion of the nucleic acid molecule into a cleavage site generated by a nuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome. In some embodiments, the homology arms are about 500 base pairs.

As used herein, the term with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), J. Mol. Biol. 215:403-410; Gish and States (1993), Nature Genet. 3:266-272; Madden et al. (1996), Meth. Enzymol. 266:131-141; Altschul et al. (1997), Nucleic Acids Res. 25:33 89-3402); Zhang et al. (2000), J. Comput. Biol. 7(1-2):203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein, the term "corresponding to" with respect to modifications of two proteins or amino acid sequences is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment and despite the fact that X and Y may be different numbers.

As used herein, the term "recognition half-site," "recognition sequence half-site," or simply "half-site" means a nucleic acid sequence in a double-stranded DNA molecule that is recognized and bound by a monomer of a homodimeric or heterodimeric meganuclease or by one subunit of a single-chain meganuclease or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs: 11-15. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-20 residues that exhibit variability and can be modified to influence base preference and/or DNA-binding affinity. In some embodiments, variable residues within a hypervariable region correspond to one or more of positions 24, 26, 28, 30, 32, 33, 38, 40, 42, 44, 46, 68, 70, 75, and 77 of any one of SEQ ID NOs: 11-15. In certain embodiments, variable residues within a hypervariable region can further correspond to residues 48, 50, and 71-73 of any one of SEQ ID NOs: 11-15. In other embodiments, variable residues within a hypervariable region correspond to one or more of positions 215, 217, 219, 221, 223, 224, 229, 231, 233, 235, 237, 239, 241, 259, 261, 262, 263, 264, 266, and 268 of any one of SEQ ID NOs: 11-15. In certain embodiments, variable residues within a hypervariable region can further correspond to residues 239, 241, and 263-265 of SEQ ID NO: 15.

As used herein, the term "transthyretin" or "TTR," as used herein, refers to any TTR polynucleotide or polypeptide (e.g., precursor polypeptide or mature polypeptide) including but not limited to mammalian TTR, such as human TTR, mouse TTR, or non-human primate TTR, or pathogenic or likely pathogenic variants thereof, including TTR polypeptides having one or more amino acid substitutions selected from Gly6Ser, Cys10Arg, Leu12Pro, Asp18Gly, Val20Ile, Ala25Thr, Val30Met, Val30Ala, Val30Leu, Val30Gly, Phe33Ile, Phe33Leu, Ala36Pro, Glu42Gly, Phe44Ser, Ala45Thr, Gly47Arg, Gly47Ala, Gly47Arg, Thr49Ala, Ser50Arg, Ser50Ile, Gly53Glu, Leu55Pro, Leu58His, Leu58Arg, Thr60Ala, Glu61Lys, Phe64Leu, Phe64Ser, Ile68Leu, Tyr69His, Lys70Asn, Val71Ala, Ser77Tyr, Ile84Ser, Glu89Gln, His90Asn, Ala97Gly, Ala97Ser, Arg104His, Ile107Val, Ala109Thr, Ala109Val, Leu111Met, Tyr114Cys, Tyr114His, Tyr116Val, Thr119Met, Val122Ile, or a Val122Del. TTR is also known as, inter alia, prealbumin, HsT2651, PALB, and TBPA.

Normally, the TTR protein is a serum/plasma and cerebrospinal fluid protein responsible for the transport of thyroxine and retinol. It is synthesized primarily by the liver, the choroid plexus of the brain, and to a minor extent in the retina in humans. TTR synthesized in the liver is secreted into the blood, and TTR originating in the choroid plexus is destined for the cerebrospinal fluid. The sequence of a human TTR mRNA transcript can be found at National Center for Biotechnology Information (NCBI) RefSeq accession number NM_000371.3. The sequence of a mouse TTR mRNA can be found at RefSeq accession number NM_013697.5. The sequence of a Rhesus monkey TTR mRNA can be found at RefSeq accession number NM_001261679.1.

A "TTR-associated disease," as used herein, includes any disease or symptoms caused by or correlated with one or more mutations in a TTR gene or polypeptide and any disease or symptom caused by the wild type or mutated TTR protein. Such a disease may be caused, for example, by excess production of the wild type or otherwise mutated TTR protein, accumulation of the wild type or otherwise mutated TTR protein as amyloid deposits, by TTR gene mutations, by abnormal cleavage of the TTR protein, by abnormal interactions between TTR and other proteins or other endogenous or exogenous substances. A "TTR-associated disease" includes any type of TTR amyloidosis (ATTR) wherein TTR plays a role in the formation of abnormal extracellular aggregates or amyloid deposits. TTR-associated diseases include, inter alia, senile systemic amyloidosis (SSA), systemic familial amyloidosis, familial amyloid polyneuropathy (FAP), familial amyloid cardiomyopathy (FAC), leptomeningeal/Central Nervous System (CNS) amyloidosis, amyloidotic vitreous opacities, carpal tunnel syndrome, and hyperthyroxinemia. Symptoms of ATTR include sensory neuropathy (e.g., paresthesia or hypoesthesia in distal limbs), autonomic neuropathy (e.g., gastrointestinal dysfunction, such as gastric ulcer, or orthostatic hypotension), motor neuropathy, seizures, dementia, myelopathy, polyneuropathy, carpal tunnel syndrome, autonomic insufficiency, cardiomyopathy, vitreous opacities, renal insufficiency, nephropathy, substantially reduced mBMI (modified Body Mass Index), cranial nerve dysfunction, and corneal lattice dystrophy.

The term "TTR levels" as used herein refers to TTR levels as measured in one or more cells, tissues, organs, and/or biological fluids (e.g., blood, serum, liver, or cerebrospinal fluid). TTR levels may be measured in a control or in a cell or subject treated with any meganuclease of the invention, or a nucleic acid encoding the meganuclease. TTR levels may be assessed based on the level of any variable associated with TTR gene expression, e.g., TTR mRNA level, TTR protein level, retinol binding protein level, vitamin A level, or the number or extent of amyloid deposits.

The terms a "decrease" or "reduction" in TTR levels refers to any decrease in the levels of TTR expression relative to a reference level including a reduction of TTR expression of at least 1%, 2%, 3%, 4%, 5%10%, 15%, 20%, 25%, 30%, 40%, 50%, 60%, 70%, 80%, 90%, 95%, or 100% when compared to a reference level or control. In some embodiments, a decrease in TTR levels refers to a decrease in full-length TTR polypeptide expression relative to a reference level including a reduction of full-length TTR polypeptide expression of at least 1%, 2%, 3%, 4%, 5%10%, 15%, 20%, 25%, 30%, 40%, 50%, 60%, 70%, 80%, 90%, 95%, or 100% when compared to a reference level or control. In certain embodiments, a TTR polypeptide that is not the full-length polypeptide has a reduced amyloid formation of at least 1%, 2%, 3%, 4%, 5%, 10%, 15%, 20%, 25%, 30%, 40%, 50%, 60%, 70%, 80%, 90%, 95%, or 100% when compared to the amyloid formation of the full-length TTR polypeptide.

As used herein, the term "modified TTR gene" refers to any modification to a TTR gene, such as an insertion, deletion, or substitution within the TTR gene. In some embodiments, the modification to a TTR gene alters (e.g., decreases) TTR levels or otherwise reduces the level of TTR amyloids in a cell or a subject relative to a reference level.

As used herein, the term "reference level" refers to a level of TTR as measured in, for example, a control cell, control cell population or a control subject, at a previous time point in the control cell, the control cell population or the subject undergoing treatment (e.g., a pre-dose baseline level obtained from the control cell, control cell population or subject), or a pre-defined threshold level of TTR (e.g., a threshold level identified through previous experimentation).

As used herein, the term "a control" or "a control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype. A control subject may comprise, for example: a wild-type subject, i.e., of the same genotype as the starting subject for the genetic alteration which resulted in the genetically-modified subject (e.g., a subject having the same mutation in a TTR gene), which is not exposed to conditions or stimuli or further genetic modifications that would induce expression of altered genotype or phenotype in the subject.

As used herein, the term "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, the term "vector" or "recombinant DNA vector" may be a construct that includes a replication system and sequences that are capable of transcription and translation of a polypeptide-encoding sequence in a given host cell. If a vector is used, then the choice of vector is dependent upon the method that will be used to transform host cells as is well known to those skilled in the art. Vectors can include, without limitation, plasmid vectors and recombinant AAV vectors, or any other vector known in the art suitable for delivering a gene to a target cell. The skilled artisan is well aware of the genetic elements that must be present on the vector in order to successfully transform, select and propagate host cells comprising any of the isolated nucleotides or nucleic acid sequences of the invention. In some embodiments, a "vector" also refers to a viral vector. Viral vectors can include, without limitation, retroviral vectors, lentiviral vectors, adenoviral vectors, and adeno-associated viral vectors (AAV).

As used herein, the term "operably linked" is intended to mean a functional linkage between two or more elements. For example, an operable linkage between a nucleic acid sequence encoding a nuclease as disclosed herein and a regulatory sequence (e.g., a promoter) is a functional link that allows for expression of the nucleic acid sequence encoding the nuclease. Operably linked elements may be contiguous or non-contiguous. When used to refer to the joining of two protein coding regions, by operably linked is intended that the coding regions are in the same reading frame.

As used herein, the term "self-cleaving" recombinant DNA construct refers to a DNA construct that comprises at least one coding sequence for a nuclease and at least one recognition sequence for the same nuclease. When expressed in a cell (i.e., in vivo), the nuclease recognizes and cleaves the recognition sequence, resulting in linearization of the DNA construct.

As used herein, the terms "treatment" or "treating a subject" refers to the administration of an engineered meganuclease of the invention, or a nucleic acid encoding an engineered meganuclease of the invention to a subject having a TTR-associated disease (e.g., transthyretin amyloidosis) for the purpose of reducing TTR levels in the subject. Such treatment reduces TTR levels, and either provides partial or complete relief of one or more symptoms of a TTR-associated disease (e.g., transthyretin amyloidosis) in the subject, such as but not limited to sensory neuropathy (e.g., paresthesia or hypoesthesia in distal limbs), autonomic neuropathy (e.g., gastrointestinal dysfunction, such as gastric ulcer, or orthostatic hypotension), motor neuropathy, seizures, dementia, myelopathy, polyneuropathy, carpal tunnel syndrome, autonomic insufficiency, cardiomyopathy, vitreous opacities, renal insufficiency, nephropathy, substantially reduced mBMI (modified Body Mass Index), cranial nerve dysfunction, and corneal lattice dystrophy. Means to assess reduction of TTR levels may include measurement of TTR levels based on the level of any variable associated with TTR gene expression, e.g., TTR mRNA level, TTR protein level, retinol binding protein level, vitamin A level, or the number or extent of amyloid deposits. The terms "treatment" or "treating a subject" can further refer to the administration of a cell (e.g., hepatocyte cell) comprising a nucleic acid encoding an engineered meganuclease, wherein the cell is delivered to a target tissue (e.g., liver) and produces the engineered meganuclease in an amount sufficient to treat a TTR-associated disease (e.g., transthyretin amyloidosis) in the subject, thereby resulting in either partial or complete relief of one or more symptoms of the TTR-associated disease. In some aspects, an engineered meganuclease of the invention, a nucleic acid encoding the same, or a genetically-modified cell or population of genetically-modified cells described herein is administered during treatment in the form of a pharmaceutical composition of the invention.

As used herein, the term "gc/kg" or "gene copies/kilogram" refers to the number of copies of a nucleic acid encoding an engineered nuclease or the number of copies of a template nucleic acid described herein per weight in kilograms of a subject that is administered the nucleic acid encoding the engineered nuclease and/or the template nucleic acid.

As used herein, the term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition and responsiveness of the subject to be treated. In specific embodiments, an effective amount of the engineered meganuclease or pharmaceutical compositions disclosed herein reduces the level of TTR, reduces the level of TTR amyloids, or reduces at least one symptom of a TTR-associated disease (e.g., transthyretin amyloidosis) in a subject. In some specific embodiments, an effective amount of a nucleic acid encoding an engineered meganuclease comprises about $1\times10^{10}$ gc/kg to about $1\times10^{14}$ gc/kg (e.g., $1\times10^{10}$ gc/kg, $1\times10^{11}$ gc/kg, $1\times10^{12}$ gc/kg, $1\times10^{13}$ gc/kg, or $1\times10^{14}$ gc/kg) of a polynucleotide comprising a nucleic acid encoding the engineered nuclease or of a template polynucleotide. In specific embodiments, an effective amount of a polynucleotide comprising a nucleic acid sequence encoding an engineered nuclease and/or a template polynucleotide, or a pharmaceutical composition comprising a polynucleotide comprising a nucleic acid sequence encoding an engineered nuclease and/or a template polynucleotide disclosed herein, reduces at least one symptom of a disease in a subject.

As used herein, the term "lipid nanoparticle" refers to a lipid composition having a typically spherical structure with an average diameter between 10 and 1000 nanometers. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use in the invention.

As used herein, the recitation of a numerical range for a variable is intended to convey that the present disclosure may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values ≥0 and ≤2 if the variable is inherently continuous.

2.1 Principle of the Invention

The present invention is based, in part, on the hypothesis that engineered meganucleases can be designed to bind and cleave recognition sequences found within a TTR gene (e.g., the human TTR gene; SEQ ID NO: 3), particularly within exon 1 or exon 3. As described further herein, targeting meganucleases to recognition sites within exon 1 or exon 3 of a TTR gene is an effective approach to disrupt the expression of TTR. Disruption of the expression of the TTR protein(s) can reduce TTR levels or reduce TTR amyloids in a subject having a TTR-associated disease, such as transthyretin amyloidosis.

In particular, cleavage within exon 1 or exon 3 of a TTR gene (e.g., at the TTR 5-6 or TTR 15-16 recognition sequences) can allow for non-homologous end joining (NHEJ) at the cleavage site and can disrupt expression of TTR due to NHEJ at the cleavage site that results in insertions, deletions, or frameshift mutations. Additionally, cleavage within exon 1 or exon 3 of a TTR gene (e.g., at the TTR 5-6 or TTR 15-16 recognition sequences) can further allow for homologous recombination of exogenous nucleic acid sequences directly into the TTR gene to disrupt TTR expression.

Thus, the present invention encompasses engineered meganucleases which bind and cleave within exon 1 or exon 3 of a TTR gene (e.g., at the TTR 5-6 or TTR 15-16 recognition sequences). The present invention also encompasses methods of using such engineered meganucleases to produce genetically-modified cells. Further, the invention encompasses pharmaceutical compositions, comprising engineered meganuclease proteins, or nucleic acids encoding engineered meganucleases, and the use of such compositions for the treatment of TTR-associated diseases, such as transthyretin amyloidosis.

2.2 Meganucleases that Bind and Cleave Recognition Sequences within a TTR Gene It is known in the art that it is possible to use a site-specific nuclease to make a DNA break in the genome of a living cell, and that such a DNA break can result in permanent modification of the genome via homologous recombination with a transgenic DNA sequence. The use of nucleases to induce a double-strand break in a target locus is known to stimulate homologous recombination, particularly of transgenic DNA sequences flanked by sequences that are homologous to the genomic target. In this manner, exogenous nucleic acid sequences can be inserted into a target locus.

It is further known in the art that it is possible to use a site-specific nuclease to make a DNA break in the genome of a living cell, and that such a DNA break can result in permanent modification of the genome via mutagenic NHEJ repair or via homologous recombination with a transgenic DNA sequence. NHEJ can produce mutagenesis at the cleavage site, resulting in inactivation of the allele. NHEJ-associated mutagenesis may inactivate an allele via generation of early stop codons, frameshift mutations producing aberrant non-functional proteins, or could trigger mechanisms such as nonsense-mediated mRNA decay. The use of nucleases to induce mutagenesis via NHEJ can be used to target a specific mutation or a sequence present in a wild-type allele. Further, the use of nucleases to induce a double-strand break in a target locus is known to stimulate homologous recombination, particularly of transgenic DNA sequences flanked by sequences that are homologous to the genomic target. In this manner, exogenous nucleic acid sequences can be inserted into a target locus. Such exogenous nucleic acids can encode any sequence or polypeptide of interest.

In some embodiments, the nucleases used to practice the invention are meganucleases. In particular embodiments, the nucleases used to practice the invention are single-chain meganucleases. A single-chain meganuclease comprises an N-terminal subunit and a C-terminal subunit joined by a linker peptide. Each of the two domains recognizes and binds to half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

In other embodiments, nucleases of the invention have been engineered to bind and cleave a TTR 15-16 recognition sequence (SEQ ID NO: 7). The TTR 15-16 recognition sequence is positioned within exon 3 of the TTR gene. An exemplary TTR 15-16 meganuclease (e.g., TTR 15-16x.81, TTR 15-16L.161, TTR 15-16L.164, and TTR 15-16L.181) is provided in SEQ ID NOs: 11-14.

In some embodiments, nucleases of the invention have been engineered to bind and cleave a TTR 5-6 recognition sequence (SEQ ID NO: 9). The TTR 5-6 recognition sequence is positioned within exon 1 of the TTR gene. An exemplary TTR 5-6 meganucleases (e.g., TTR 5-6L.1204) is provided in SEQ ID NO: 15.

Engineered meganucleases of the invention comprise a first subunit, comprising a first hypervariable (HVR1) region, and a second subunit, comprising a second hypervariable (HVR2) region. Further, the first subunit binds to a first recognition half-site in the recognition sequence (i.e., the TTR 5 or TTR 15 half-site), and the second subunit binds to a second recognition half-site in the recognition sequence (i.e., the TTR 6 or TTR 16 half-site). In embodiments where the engineered meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary TTR meganucleases of the invention are provided in SEQ ID NOs: 11-15 and summarized in Tables 1 and 2 and the descriptions below.

TABLE 1

Exemplary engineered meganucleases which bind and cleave the consensus TTR 15-16 recognition sequence (SEQ ID NO: 7).

| Meganuclease | AA SEQ ID | TTR15 Subunit Residues | TTR15 Subunit SEQ ID | *TTR15 Subunit % | TTR16 Subunit Residues | TTR16 Subunit SEQ ID | TTR16 Subunit % |
|---|---|---|---|---|---|---|---|
| TTR 15-16x.81 | 11 | 7-153 | 16 | 100 | 198-344 | 20 | 100 |
| TTR 15-16L.161 | 12 | 7-153 | 17 | 97.96 | 198-344 | 21 | 100 |
| TTR 15-16L.164 | 13 | 7-153 | 18 | 97.96 | 198-344 | 22 | 99.32 |
| TTR 15-16L.181 | 14 | 7-153 | 19 | 99.32 | 198-344 | 23 | 99.32 |

"TTR15 Subunit %" and "TTR16 Subunit %" represent the amino acid sequence identity between the TTR15-binding and TTR16-binding subunit regions of each meganuclease and the TTR15-binding and TTR16-binding subunit regions, respectively, of the TTR 15-16x.81 meganuclease.

TABLE 2

Exemplary engineered meganucleases which bind and cleave the consensus TTR 5-6 recognition sequence (SEQ ID NO: 9).

| Meganuclease | AA SEQ ID | TTR5 Subunit Residues | TTR5 Subunit SEQ ID | *TTR5 Subunit % | TTR6 Subunit Residues | TTR6 Subunit SEQ ID | TTR6 Subunit % |
|---|---|---|---|---|---|---|---|
| TTR 5-6L.1204 | 15 | 7-153 | 24 | 100 | 198-344 | 25 | 100 |

In certain embodiments of the invention, the engineered meganuclease binds and cleaves a recognition sequence comprising SEQ ID NO: 7 within an TTR gene, wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

TTR 15-16x.81 (SEQ ID NO: 11)

In some embodiments, the HVR1 region comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to an amino acid sequence corresponding to residues 24-79 of SEQ ID NO: 11. In some such embodiments, the HVR1 region comprises one or more residues corresponding to residues 24, 26, 28, 30, 32, 33, 38, 40, 42, 44, 46, 68, 70, 75, and 77 of SEQ ID NO: 11. In some such embodiments, the HVR1 region comprises residues corresponding to residues 24, 26, 28, 30, 32, 33, 38, 40, 42, 44, 46, 68, 70, 75, and 77 of SEQ ID NO: 11. In some such embodiments, the HVR1 region comprises Y, R, K, or D at a residue corresponding to residue 66 of SEQ ID NO: 11. In some such embodiments, said HVR1 region comprises one or more residues corresponding to residues 48, 50, and 71-73, of SEQ ID NO: 11. In some such embodiments, said HVR1 region comprises residues corresponding to residues 48, 50, and 71-73, of SEQ ID NO: 11. In some such embodiments, the HVR1 region comprises residues 24-79 of SEQ ID NO: 11. In some such embodiments, the HVR2 region comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to an amino acid sequence corresponding to residues 215-270 of SEQ ID NO: 11. In some such embodiments, the HVR2 region comprises one or more residues corresponding to residues 215, 217, 219, 221, 223, 224, 229, 231, 233, 235, 237, 259, 261, 266, and 268 of SEQ ID NO: 11. In some such embodiments, the HVR2 region comprises residues corresponding to residues 215, 217, 219, 221, 223, 224, 229, 231, 233, 235, 237, 259, 261, 266, and 268 of SEQ ID NO: 11. In some such embodiments, the HVR2 region comprises Y, R, K, or D at a residue corresponding to residue 257 of SEQ ID NO: 11. In some such embodiments, the HVR2 region comprises residues 215-270 of SEQ ID NO: 11. In some such embodiments, the first subunit comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to residues 7-153 of SEQ ID NO: 11, and wherein the second subunit comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to residues 198-344 of SEQ ID NO: 11. In some such embodiments, the first subunit comprises G, S, or A at a residue corresponding to residue 19 of SEQ ID NO: 11. In some such embodiments, said first subunit comprises one or more residues corresponding to residues 19 and 139 of SEQ ID NO: 11. In some such embodiments, said first subunit comprises residues corresponding to residues 19 and 139 of SEQ ID NO: 11. In some such embodiments, the first subunit comprises E, Q, or K at a residue corresponding to residue 80 of SEQ ID NO: 11. In some such embodiments, the second subunit comprises G, S, or A at a residue corresponding to residue 210 of SEQ ID NO: 11. In some such embodiments, the second subunit comprises E, Q, or K at a residue corresponding to residue 271 of SEQ ID NO: 11. In some such embodiments, the first subunit comprises a residue corresponding to residue 80 of SEQ ID NO: 11. In some such embodiments, the second subunit comprises a residue corresponding to residue 271 of SEQ ID NO: 11. In some such embodiments, the engineered meganuclease is a single-chain meganuclease comprising a linker, wherein the linker covalently joins the first subunit and the second subunit. In some such embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to SEQ ID NO: 11. In some such embodiments, the engineered meganuclease comprises the amino acid sequence of SEQ ID NO: 11. In some embodiments, the engineered meganuclease is encoded by a nucleic acid sequence having at least 80%, at least 85%, at least 90%, at least 91%, at least 92%, at least 93%, at least 94%, at least 95%, at least 96%, at least 97%, at least 98%, or at least 99% sequence identity to a nucleic acid sequence of SEQ ID NO: 66. In some embodiments, the engineered meganuclease is encoded by a nucleic acid sequence of SEQ ID NO: 66.

TTR 15-16L.161 (SEQ ID NO: 12)

In some embodiments, the HVR1 region comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to an amino acid sequence corresponding to residues 24-79 of SEQ ID NO: 12. In some such embodiments, the HVR1 region comprises one or more residues corresponding to residues 24, 26, 28, 30, 32, 33, 38, 40, 42, 44, 46, 68, 70, 75, and 77 of SEQ ID NO: 12. In some such embodiments, the HVR1 region comprises residues corresponding to residues 24, 26, 28, 30, 32, 33, 38, 40, 42, 44, 46, 68, 70, 75, and 77 of SEQ ID NO: 12. In some such embodiments, the HVR1 region comprises Y, R, K, or D at a residue corresponding to residue 66 of SEQ ID NO: 12. In some such embodiments, said HVR1 region comprises one or more residues corresponding to residues 48, 50, and 71-73, of SEQ ID NO: 12. In some such embodiments, said HVR1 region comprises residues corresponding to residues 48, 50, and 71-73, of SEQ ID NO: 12. In some such embodiments, the HVR1 region comprises residues 24-79 of SEQ ID NO: 12. In some such embodiments, the HVR2 region comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to an amino acid sequence corresponding to residues 215-270 of SEQ ID NO: 12. In some such embodiments, the HVR2 region comprises one or more residues corresponding to residues 215, 217, 219, 221, 223, 224, 229, 231, 233, 235, 237, 259, 261, 266, and 268 of SEQ ID NO: 12. In some such embodiments, the HVR2 region comprises residues corresponding to residues 215, 217, 219, 221, 223, 224, 229, 231, 233, 235, 237, 259, 261, 266, and 268 of SEQ ID NO: 12. In some such embodiments, the HVR2 region comprises Y, R, K, or D at a residue corresponding to residue 257 of SEQ ID NO: 12. In some such embodiments, the HVR2 region comprises residues 215-270 of SEQ ID NO: 12. In some such embodiments, the first subunit comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to residues 7-153 of SEQ ID NO: 12, and wherein the second subunit comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to residues 198-344 of SEQ ID NO: 12. In some such embodiments, the first subunit comprises G, S, or A at a residue corresponding to residue 19 of SEQ ID NO: 12. In some such embodiments, said first subunit comprises one or more residues corresponding to residues 19 and 139 of SEQ ID NO: 12. In some such embodiments, said first subunit comprises residues corresponding to residues 19 and 139 of SEQ ID NO: 12. In some such embodiments, the first subunit comprises E, Q, or K at a residue corresponding to residue 80 of SEQ ID NO:

12. In some such embodiments, the second subunit comprises G, S, or A at a residue corresponding to residue 210 of SEQ ID NO: 12. In some such embodiments, the second subunit comprises E, Q, or K at a residue corresponding to residue 271 of SEQ ID NO: 12. In some such embodiments, the first subunit comprises a residue corresponding to residue 80 of SEQ ID NO: 12. In some such embodiments, the second subunit comprises a residue corresponding to residue 271 of SEQ ID NO: 12. In some such embodiments, the engineered meganuclease is a single-chain meganuclease comprising a linker, wherein the linker covalently joins the first subunit and the second subunit. In some such embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to SEQ ID NO: 12. In some such embodiments, the engineered meganuclease comprises the amino acid sequence of SEQ ID NO: 12. In some embodiments, the engineered meganuclease is encoded by a nucleic acid sequence having at least 80%, at least 85%, at least 90%, at least 91%, at least 92%, at least 93%, at least 94%, at least 95%, at least 96%, at least 97%, at least 98%, or at least 99% sequence identity to a nucleic acid sequence of SEQ ID NO: 67. In some embodiments, the engineered meganuclease is encoded by a nucleic acid sequence of SEQ ID NO: 67.

TTR 15-16L.164 (SEQ ID NO: 13)

In some embodiments, the HVR1 region comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to an amino acid sequence corresponding to residues 24-79 of SEQ ID NO: 13. In some such embodiments, the HVR1 region comprises one or more residues corresponding to residues 24, 26, 28, 30, 32, 33, 38, 40, 42, 44, 46, 68, 70, 75, and 77 of SEQ ID NO: 13. In some such embodiments, the HVR1 region comprises residues corresponding to residues 24, 26, 28, 30, 32, 33, 38, 40, 42, 44, 46, 68, 70, 75, and 77 of SEQ ID NO: 13. In some such embodiments, the HVR1 region comprises Y, R, K, or D at a residue corresponding to residue 66 of SEQ ID NO: 13. In some such embodiments, said HVR1 region comprises one or more residues corresponding to residues 48, 50, and 71-73, of SEQ ID NO: 13. In some such embodiments, said HVR1 region comprises residues corresponding to residues 48, 50, and 71-73, of SEQ ID NO: 13. In some such embodiments, the HVR1 region comprises residues 24-79 of SEQ ID NO: 13. In some such embodiments, the HVR2 region comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to an amino acid sequence corresponding to residues 215-270 of SEQ ID NO: 13. In some such embodiments, the HVR2 region comprises one or more residues corresponding to residues 215, 217, 219, 221, 223, 224, 229, 231, 233, 235, 237, 259, 261, 266, and 268 of SEQ ID NO: 13. In some such embodiments, the HVR2 region comprises residues corresponding to residues 215, 217, 219, 221, 223, 224, 229, 231, 233, 235, 237, 259, 261, 266, and 268 of SEQ ID NO: 13. In some such embodiments, the HVR2 region comprises Y, R, K, or D at a residue corresponding to residue 257 of SEQ ID NO: 13. In some such embodiments, the HVR2 region comprises residues 215-270 of SEQ ID NO: 13. In some such embodiments, the first subunit comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to residues 7-153 of SEQ ID NO: 13, and wherein the second subunit comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to residues 198-344 of SEQ ID NO: 13. In some such embodiments, the first subunit comprises G, S, or A at a residue corresponding to residue 19 of SEQ ID NO: 13. In some such embodiments, said first subunit comprises one or more residues corresponding to residues 19 and 139 of SEQ ID NO: 13. In some such embodiments, said first subunit comprises residues corresponding to residues 19 and 139 of SEQ ID NO: 13. In some such embodiments, the first subunit comprises E, Q, or K at a residue corresponding to residue 80 of SEQ ID NO: 13. In some such embodiments, the second subunit comprises G, S, or A at a residue corresponding to residue 210 of SEQ ID NO: 13. In some such embodiments, the second subunit comprises E, Q, or K at a residue corresponding to residue 271 of SEQ ID NO: 13. In some such embodiments, the first subunit comprises a residue corresponding to residue 80 of SEQ ID NO: 13. In some such embodiments, the second subunit comprises a residue corresponding to residue 271 of SEQ ID NO: 13. In some such embodiments, the engineered meganuclease is a single-chain meganuclease comprising a linker, wherein the linker covalently joins the first subunit and the second subunit. In some such embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to SEQ ID NO: 13. In some such embodiments, the engineered meganuclease comprises the amino acid sequence of SEQ ID NO: 13. In some embodiments, the engineered meganuclease is encoded by a nucleic acid sequence having at least 80%, at least 85%, at least 90%, at least 91%, at least 92%, at least 93%, at least 94%, at least 95%, at least 96%, at least 97%, at least 98%, or at least 99% sequence identity to a nucleic acid sequence of SEQ ID NO: 68. In some embodiments, the engineered meganuclease is encoded by a nucleic acid sequence of SEQ ID NO: 68.

TTR 15-16L.181 (SEQ ID NO: 14)

In some embodiments, the HVR1 region comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to an amino acid sequence corresponding to residues 24-79 of SEQ ID NO: 14. In some such embodiments, the HVR1 region comprises one or more residues corresponding to residues 24, 26, 28, 30, 32, 33, 38, 40, 42, 44, 46, 68, 70, 75, and 77 of SEQ ID NO: 14. In some such embodiments, the HVR1 region comprises residues corresponding to residues 24, 26, 28, 30, 32, 33, 38, 40, 42, 44, 46, 68, 70, 75, and 77 of SEQ ID NO: 14. In some such embodiments, the HVR1 region comprises Y, R, K, or D at a residue corresponding to residue 66 of SEQ ID NO: 14. In some such embodiments, said HVR1 region comprises one or more residues corresponding to residues 48, 50, and 71-73, of SEQ ID NO: 14. In some such embodiments, said HVR1 region comprises residues corresponding to residues 48, 50, and 71-73, of SEQ ID NO: 14. In some such embodiments, the HVR1 region comprises residues 24-79 of SEQ ID NO: 14. In some such embodiments, the HVR2 region comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to an amino acid sequence corresponding to residues 215-270 of SEQ ID NO: 14. In some such embodiments, the HVR2 region comprises one or more residues corresponding to residues 215, 217, 219, 221, 223, 224, 229, 231, 233, 235, 237, 259, 261, 266, and 268 of SEQ ID NO: 14. In some such embodiments, the HVR2 region comprises residues corresponding to residues 215, 217, 219, 221, 223, 224, 229, 231, 233, 235, 237, 259, 261, 266, and 268 of SEQ ID NO: 14. In some such embodiments, the HVR2 region comprises Y, R, K, or D at a residue corresponding to residue 257 of SEQ ID NO: 14. In some such embodiments, the HVR2 region comprises residues 215-270 of SEQ ID NO: 14. In some such embodiments, the first subunit comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to residues 7-153 of SEQ ID NO: 14, and wherein the second subunit comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to residues 198-344 of SEQ ID NO: 14. In some such embodiments, the first subunit comprises G, S, or A at a residue corresponding to residue 19 of SEQ ID NO: 14. In some such embodiments, said first subunit comprises one or more residues corresponding to residues 19 and 139 of SEQ ID NO: 14. In some such embodiments, said first subunit comprises residues corresponding to residues 19 and 139 of SEQ ID NO: 14. In some such embodiments, the first subunit comprises E, Q, or K at a residue corresponding to residue 80 of SEQ ID NO: 14. In some such embodiments, the second subunit comprises G, S, or A at a residue corresponding to residue 210 of SEQ ID NO: 14. In some such embodiments, the second subunit comprises E, Q, or K at a residue corresponding to residue 271 of SEQ ID NO: 14. In some such embodiments, the first subunit comprises a residue corresponding to residue 80 of SEQ ID NO: 14. In some such embodiments, the second subunit comprises a residue corresponding to residue 271 of SEQ ID NO: 14. In some such embodiments, the engineered meganuclease is a single-chain meganuclease comprising a linker, wherein the linker covalently joins the first subunit and the second subunit. In some such embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to SEQ ID NO: 14. In some such embodiments, the engineered meganuclease comprises the amino acid sequence of SEQ ID NO: 14. In some embodiments, the engineered meganuclease is encoded by a nucleic acid sequence having at least 80%, at least 85%, at least 90%, at least 91%, at least 92%, at least 93%, at least 94%, at least 95%, at least 96%, at least 97%, at least 98%, or at least 99% sequence identity to a nucleic acid sequence of SEQ ID NO: 69. In some embodiments, the engineered meganuclease is encoded by a nucleic acid sequence of SEQ ID NO: 69.

In certain embodiments of the invention, the engineered meganuclease binds and cleaves a recognition sequence comprising SEQ ID NO: 9 within an TTR gene, wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

TTR 5-6L.1204 (SEQ ID NO: 15)

In some embodiments, the HVR1 region comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to an amino acid sequence corresponding to residues 24-79 of SEQ ID NO: 15. In some such embodiments, the HVR1 region comprises one or more residues corresponding to residues 24, 26, 28, 30, 32, 33, 38, 40, 42, 44, 46, 68, 70, 75, and 77 of SEQ ID NO: 15. In some such embodiments, the HVR1 region comprises residues corresponding to residues 24, 26, 28, 30, 32, 33, 38, 40, 42, 44, 46, 68, 70, 75, and 77 of SEQ ID NO: 15. In some such embodiments, the HVR1 region comprises Y, R, K, or D at a residue corresponding to residue 66 of SEQ ID NO: 15. In some such embodiments, the HVR1 region comprises residues 24-79 of SEQ ID NO: 15. In some such embodiments, the HVR2 region comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to an amino acid sequence corresponding to residues 215-270 of SEQ ID NO: 15. In some such embodiments, the HVR2 region comprises one or more residues corresponding to residues 215, 217, 219, 221, 223, 224, 229, 231, 233, 235, 237, 259, 261, 266, and 268 of SEQ ID NO: 15. In some such embodiments, the HVR2 region comprises residues corresponding to residues 215, 217, 219, 221, 223, 224, 229, 231, 233, 235, 237, 259, 261, 266, and 268 of SEQ ID NO: 15. In some such embodiments, the HVR2 region comprises Y, R, K, or D at a residue corresponding to residue 257 of SEQ ID NO: 15. In some such embodiments, said HVR2 region comprises one or more residues corresponding to residues 239, 241, and 263-265 of SEQ ID NO: 15. In some such embodiments, said HVR2 region comprises residues corresponding to residues 239, 241, and 263-265 of SEQ ID NO: 15. In some such embodiments, the HVR2 region comprises residues 215-270 of SEQ ID NO: 15. In some such embodiments, the first subunit comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to residues 7-153 of SEQ ID NO: 15, and wherein the second subunit comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to residues 198-344 of SEQ ID NO: 15. In some such embodiments, the first subunit comprises G, S, or A at a residue corresponding to residue 19 of SEQ ID NO: 15. In some such embodiments, the first subunit comprises E, Q, or K at a residue corresponding to residue 80 of SEQ ID NO: 15. In some such embodiments, the second subunit comprises G, S, or A at a residue corresponding to residue 210 of SEQ ID NO: 15. In some such embodiments, the second subunit comprises E, Q, or K at a residue corresponding to residue 271 of SEQ ID NO: 15. In some such embodiments, the first subunit comprises a residue corresponding to residue 80 of SEQ ID NO: 15. In some such embodiments, said second subunit comprises a residue corresponding to residue 210 of SEQ ID NO: 15. In some such embodiments, the second subunit comprises a residue corresponding to residue 271 of SEQ ID NO: 15. In some such embodiments, the engineered meganuclease is a single-chain meganuclease comprising a linker, wherein the linker covalently joins the first subunit and the second subunit. In some such embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to SEQ ID NO: 15. In some such embodiments, the engineered meganuclease comprises the amino acid sequence of SEQ ID NO: 15. In some embodiments, the engineered meganuclease is encoded by a nucleic acid sequence having at least 80%, at least 85%, at least 90%, at least 91%, at least 92%, at least 93%, at least 94%, at least 95%, at least 96%, at least 97%, at least 98%, or at least 99% sequence identity to a nucleic acid sequence of SEQ ID NO: 70. In some embodiments, the engineered meganuclease is encoded by a nucleic acid sequence of SEQ ID NO: 70.

2.3 Methods for Delivering and Expressing Meganucleases

The invention provides methods for producing genetically-modified cells using engineered nucleases that bind and cleave recognition sequences found within a TTR gene (e.g., the human TTR gene; SEQ ID NO:3). Cleavage at such recognition sequences can allow for NHEJ at the cleavage site and/or insertion of an exogenous sequence via homologous recombination, thereby disrupting expression of the endogenous TTR polypeptide in the genetically-modified cell. The invention further provides methods for treating a disease in a subject by administering a pharmaceutical composition comprising a pharmaceutically acceptable carrier and a nucleic acid encoding an engineered nuclease or the engineered nuclease polypeptide. In each case, the invention includes that an engineered nuclease of the invention, or a nucleic acid encoding the engineered nuclease, can be delivered (i.e., introduced) into cells that would typically produce a TTR gene product (e.g., a TTR polypeptide).

Accordingly, provided herein are methods for treating TTR-associated diseases (e.g., transthyretin amyloidosis), reducing the level of TTR, reducing the level of TTR amyloids, or reducing the symptoms associated with TTR-associated diseases (e.g., transthyretin amyloidosis) in a subject. In particular, provided are methods for administering a pharmaceutical composition comprising a pharmaceutically acceptable carrier and an engineered meganuclease disclosed herein (or a nucleic acid encoding the engineered meganuclease or a cell expressing the engineered meganuclease). Engineered nucleases of the invention can be delivered into a cell in the form of protein or, preferably, as a nucleic acid encoding the engineered nuclease. Such nucleic acid can be DNA (e.g., circular or linearized plasmid DNA or PCR products) or RNA (e.g., mRNA).

The methods of the invention can be used in the treatment of any TTR-associated disease, such as TTR amyloidosis (ATTR), wherein TTR plays a role in the formation of abnormal extracellular aggregates or amyloid deposits. TTR-associated diseases include senile systemic amyloidosis (SSA), systemic familial amyloidosis, familial amyloid polyneuropathy (FAP), familial amyloid cardiomyopathy (FAC), leptomeningeal/Central Nervous System (CNS) amyloidosis, amyloidotic vitreous opacities, carpal tunnel syndrome, and hyperthyroxinemia. In certain embodiments, the methods are effective to treat ATTR. In particular embodiments, the ATTR is neuropathic ATTR, leptomeningeal ATTR, or cardiac ATTR.

Further, the methods can be effective to reduce one or more symptoms of TTR amyloidosis including sensory neuropathy (e.g., paresthesia or hypoesthesia in distal limbs), autonomic neuropathy (e.g., gastrointestinal dysfunction, such as gastric ulcer, or orthostatic hypotension), motor neuropathy, seizures, dementia, myelopathy, polyneuropathy, carpal tunnel syndrome, autonomic insufficiency, cardiomyopathy, vitreous opacities, renal insufficiency, nephropathy, substantially reduced mBMI (modified Body Mass Index), cranial nerve dysfunction, and/or corneal lattice dystrophy.

A subject having TTR-associated diseases or a subject who may be particularly receptive to treatment with the engineered meganucleases herein may be identified by ascertaining the presence or absence of one or more risk factors, diagnostic, or prognostic indicators, such as those described herein. For example, in some instances, the subject has a mutation in a TTR gene that affects the peripheral nervous system, the autonomic nervous system, the leptomeninges, and/or the heart. In certain instances, the subject undergoing treatment in accordance with the methods and compositions provided herein can be characterized by one or more (e.g., 1, 2, 3, 4, 5, 6, 7, 8, 9, 10, 15, 20, 25, or 27) mutations in the TTR gene or polypeptide. For example, the subject undergoing treatment may have a TTR gene encoding a TTR polypeptide with one or more amino acid substitutions selected from Gly6Ser, Cys10Arg, Leu12Pro, Asp18Gly, Val20Ile, Ala25Thr, Val30Met, Val30Ala, Val30Leu, Val30Gly, Phe33Ile, Phe33Leu, Ala36Pro, Glu42Gly, Phe44Ser, Ala45Thr, Gly47Arg, Gly47Ala, Gly47Arg, Thr49Ala, Ser50Arg, Ser50Ile, Gly53Glu, Leu55Pro, Leu58His, Leu58Arg, Thr60Ala, Glu61Lys, Phe64Leu, Phe64Ser, Ile68Leu, Tyr69His, Lys70Asn, Val71Ala, Ser77Tyr, Ile84Ser, Glu89Gln, His90Asn, Ala97Gly, Ala97Ser, Arg104His, Ile107Val, Ala109Thr, Ala109Val, Leu111Met, Tyr114Cys, Tyr114His, Tyr116Val, Thr119Met, Val122Ile, or a Val122Del mutation. In certain embodiments, the subject undergoing treatment has a Val30Met (V30M) amino acid substitution in the TTR polypeptide (SEQ ID NO: 6).

TTR expression in a genetically-modified cell or subject can be detected using standard methods in the art. For example, TTR levels may be assessed based on the level of any variable associated with TTR gene expression, e.g., TTR mRNA level, TTR protein level, retinol binding protein level, vitamin A level, or the number or extent of amyloid deposits. Reduction of TTR levels or expression may be assessed by a decrease in an absolute or relative level of one or more of these variables compared with a reference level. TTR levels may be measured in a biological sample isolated from a subject, such as a tissue biopsy or a bodily fluid including blood, serum, plasma, cerebrospinal fluid, or urine. Optionally, TTR levels are normalized to a standard protein or substance in the sample. Further, TTR levels can be assessed any time before, during, or after treatment in accordance with the methods herein.

The methods include administration of any of the engineered meganucleases described herein, or nucleic acids encoding the meganucleases, to reduce TTR levels or reduce TTR amyloid formation in a genetically-modified cell or a subject (e.g., as measured in a cell, a tissue, an organ, or a biological sample obtained from the subject), e.g., by at least 1%, 2%, 3%, 4%, 5%, 10%, 15%, 20%, 25%, 30%, 40%, 50%, 60%, 70%, 80%, 90%, 95%, or 100% relative to a reference level. In some embodiments, the methods herein are effective to reduce the level of TTR by about 10% to about 80% (e.g., 10%-20%, 20%-30%, 30%-40%, 40%-50%, 50%-60%, 60%-70%, 70%-80%, or more) relative to a reference level. In some embodiments, a decrease in TTR levels refers to a decrease in full-length TTR polypeptide expression relative to a reference level including a reduction of full-length TTR polypeptide expression of at least 1%, 2%, 3%, 4%, 5%, 10%, 15%, 20%, 25%, 30%, 40%, 50%, 60%, 70%, 80%, 90%, 95%, or 100% when compared to a reference level or control. In certain embodiments, a TTR polypeptide that is not the full-length polypeptide has reduced activity including reduced activity of at least 1%, 2%, 3%, 4%, 5%, 10%, 15%, 20%, 25%, 30%, 40%, 50%, 60%, 70%, 80%, 90%, 95%, or 100% when compared to the activity of the full-length TTR polypeptide.

In certain embodiments, the methods herein may be effective to reduce TTR amyloid formation in a subject. For example, TTR amyloid formation may be reduced by about 10% to about 100% (e.g., 10%-20%, 20%-30%, 30%-40%, 40%-50%, 50%-60%, 60-70%, 70%-80%, 80%-90%, or 90%-100%) relative to a reference level. In some embodiments, TTR amyloid formation is reduced by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, or about 100% relative to a reference level.

Engineered meganucleases disclosed herein can be delivered into a cell in the form of protein or, preferably, as a nucleic acid encoding the engineered meganuclease. Such nucleic acid can be DNA (e.g., circular or linearized plasmid DNA or PCR products) or RNA (e.g., mRNA). For embodiments in which the engineered meganuclease coding sequence is delivered in DNA form, it should be operably linked to a promoter to facilitate transcription of the nuclease gene. Mammalian promoters suitable for the invention include constitutive promoters such as the cytomegalovirus early (CMV) promoter (Thomsen et al. (1984), *Proc Natl Acad Sci USA.* 81(3):659-63) or the SV40 early promoter (Benoist and Chambon (1981), *Nature.* 290(5804):304-10) as well as inducible promoters such as the tetracycline-inducible promoter (Dingermann et al. (1992), *Mol Cell Biol.* 12(9):4038-45). An engineered nuclease of the invention can also be operably linked to a synthetic promoter. Synthetic promoters can include, without limitation, the JeT promoter (WO 2002/012514). In specific embodiments, a nucleic acid sequence encoding an engineered nuclease of the invention is operably linked to a tissue-specific promoter, such as a liver-specific promoter. Examples of liver-specific promoters include, without limitation, the human thyroxine binding globulin (TBG) promoter, the human alpha-1 antitrypsin promoter, hybrid liver-specific promoter (hepatic locus control region from ApoE gene (ApoE-HCR) and a liver-specific alpha1-antitrypsin promoter), and apolipoprotein A-II promoter.

In specific embodiments, a nucleic acid sequence encoding at least one engineered nuclease is delivered on a recombinant DNA construct or expression cassette. For example, the recombinant DNA construct can comprise an expression cassette (i.e., "cassette") comprising a promoter and a nucleic acid sequence encoding an engineered nuclease described herein.

In some embodiments, mRNA encoding the engineered nuclease is delivered to a cell because this reduces the likelihood that the gene encoding the engineered nuclease will integrate into the genome of the cell.

Such mRNA encoding an engineered meganuclease can be produced using methods known in the art such as in vitro transcription. In some embodiments, the mRNA is 5' capped using 7-methyl-guanosine, anti-reverse cap analogs (ARCA) (U.S. Pat. No. 7,074,596), CleanCap® analogs such as Cap 1 analogs (Trilink, San Diego, CA), or enzymatically capped using vaccinia capping enzyme or similar. In some embodiments, the mRNA may be polyadenylated. The mRNA may contain various 5' and 3' untranslated sequence elements to enhance expression the encoded engineered meganuclease and/or stability of the mRNA itself. Such elements can include, for example, posttranslational regulatory elements such as a woodchuck hepatitis virus posttranslational regulatory element. The mRNA may contain nucleoside analogs or naturally-occurring nucleosides, such as pseudouridine, 5-methylcytidine, N6-methyladenosine, 5-methyluridine, or 2-thiouridine. Additional nucleoside analogs include, for example, those described in U.S. Pat. No. 8,278,036.

Purified nuclease proteins can be delivered into cells to cleave genomic DNA, which allows for homologous recombination or non-homologous end-joining at the cleavage site with an exogenous nucleic acid molecule encoding a polypeptide of interest as described herein, by a variety of different mechanisms known in the art, including those further detailed herein.

In another particular embodiment, a nucleic acid encoding a nuclease of the invention is introduced into the cell using a single-stranded DNA template. The single-stranded DNA can further comprise a 5' and/or a 3' AAV inverted terminal repeat (ITR) upstream and/or downstream of the sequence encoding the engineered nuclease. The single-stranded DNA can further comprise a 5' and/or a 3' homology arm upstream and/or downstream of the sequence encoding the engineered meganuclease.

In another particular embodiment, genes encoding a nuclease of the invention is introduced into a cell using a linearized DNA template. Such linearized DNA templates can be produced by methods known in the art. For example, a plasmid DNA encoding a nuclease can be digested by one or more restriction enzymes such that the circular plasmid DNA is linearized prior to being introduced into a cell.

Purified engineered nuclease proteins, or nucleic acids encoding engineered nucleases, can be delivered into cells to cleave genomic DNA by a variety of different mechanisms known in the art, including those further detailed herein below.

In some embodiments, nuclease proteins, DNA/mRNA encoding nucleases, or cells expressing nuclease proteins are formulated for systemic administration, or administration to target tissues, in a pharmaceutically acceptable carrier in accordance with known techniques. See, e.g., Remington, The Science And Practice of Pharmacy (21st ed., Philadelphia, Lippincott, Williams & Wilkins, 2005). In the manufacture of a pharmaceutical formulation according to the invention, proteins/RNA/mRNA/cells are typically admixed with a pharmaceutically acceptable carrier. The carrier must be acceptable in the sense of being compatible with any other ingredients in the formulation and must not be deleterious to the patient. The carrier can be a solid or a liquid, or both, and can be formulated with the compound as a unit-dose formulation.

In some embodiments, the nuclease proteins, or DNA/mRNA encoding the nuclease, are coupled to a cell penetrating peptide or targeting ligand to facilitate cellular uptake. Examples of cell penetrating peptides known in the art include poly-arginine (Jearawiriyapaisarn, et al. (2008)

*Mol Ther.* 16:1624-9), TAT peptide from the HIV virus (Hudecz et al. (2005), *Med. Res. Rev.* 25: 679-736), MPG (Simeoni, et al. (2003) *Nucleic Acids Res.* 31:2717-2724), Pep-1 (Deshayes et al. (2004) *Biochemistry* 43: 7698-7706, and HSV-1 VP-22 (Deshayes et al. (2005) *Cell Mol Life Sci.* 62:1839-49. In an alternative embodiment, engineered nucleases, or DNA/mRNA encoding nucleases, are coupled covalently or non-covalently to an antibody that recognizes a specific cell-surface receptor expressed on target cells such that the nuclease protein/DNA/mRNA binds to and is internalized by the target cells. Alternatively, engineered nuclease protein/DNA/mRNA can be coupled covalently or non-covalently to the natural ligand (or a portion of the natural ligand) for such a cell-surface receptor. (McCall, et al. (2014) *Tissue Barriers.* 2(4):e944449; Dinda, et al. (2013) *Curr Pharm Biotechnol.* 14:1264-74; Kang, et al. (2014) *Curr Pharm Biotechnol.* 15(3):220-30; Qian et al. (2014) *Expert Opin Drug Metab Toxicol.* 10(11):1491-508).

In some embodiments, nuclease proteins, or DNA/mRNA encoding nucleases, are encapsulated within biodegradable hydrogels for injection or implantation within the desired region of the liver (e.g., in proximity to hepatic sinusoidal endothelial cells or hematopoietic endothelial cells, or progenitor cells which differentiate into the same). Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Kang Derwent et al. (2008) Trans Am Ophthalmol Soc. 106:206-214).

In some embodiments, meganuclease proteins, or DNA/mRNA encoding meganucleases, are coupled covalently or, preferably, non-covalently to a nanoparticle or encapsulated within such a nanoparticle using methods known in the art (Sharma, et al. (2014) *Biomed Res Int.* 2014). A nanoparticle is a nanoscale delivery system whose length scale is <1 μm, preferably <100 nm. Such nanoparticles may be designed using a core composed of metal, lipid, polymer, or biological macromolecule, and multiple copies of the meganuclease proteins, mRNA, or DNA can be attached to or encapsulated with the nanoparticle core. This increases the copy number of the protein/mRNA/DNA that is delivered to each cell and, so, increases the intracellular expression of each meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) *Biomaterials.* 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the nuclease proteins or DNA/mRNA encoding the nucleases are encapsulated within liposomes or complexed using cationic lipids (see, e.g., LIPOFECTAMINE™, Life Technologies Corp., Carlsbad, CA; Zuris et al. (2015) Nat Biotechnol. 33: 73-80; Mishra et al. (2011) J Drug Deliv. 2011:863734). The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, meganuclease proteins, or DNA/mRNA encoding meganucleases, are encapsulated within polymeric scaffolds (e.g., PLGA) or complexed using cationic polymers (e.g., PEI, PLL) (Tamboli et al. (2011) *Ther Deliv.* 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, meganuclease proteins, or DNA/mRNA encoding engineered meganucleases, are combined with amphiphilic molecules that self-assemble into micelles (Tong et al. (2007) *J Gene Med.* 9(11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, meganuclease proteins, or DNA/mRNA encoding meganucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in U.S. Pat. Nos. 6,015,832, 6,506,803, 6,635,676, 6,559,189, and 7,767,216, each of which is incorporated herein by reference in its entirety.

In some embodiments, meganuclease proteins, or DNA/mRNA encoding meganucleases, are covalently attached to, or non-covalently associated with, multifunctional polymer conjugates, DNA dendrimers, and polymeric dendrimers (Mastorakos et al. (2015) *Nanoscale.* 7(9): 3845-56; Cheng et al. (2008) *J Pharm Sci.* 97(1): 123-43). The dendrimer generation can control the payload capacity and size and can provide a high payload capacity. Moreover, display of multiple surface groups can be leveraged to improve stability, reduce nonspecific interactions, and enhance cell-specific targeting and drug release.

In some embodiments, genes encoding a nuclease are introduced into a cell using a recombinant virus (i.e., a recombinant viral vector). Such recombinant viruses are known in the art and include recombinant retroviruses, recombinant lentiviruses, recombinant adenoviruses, and recombinant adeno-associated viruses (AAVs) (reviewed in Vannucci, et al. (2013 *New Microbiol.* 36:1-22). Recombinant AAVs useful in the invention can have any serotype that allows for transduction of the virus into a target cell type and expression of the nuclease gene in the target cell. For example, in some embodiments, recombinant AAVs have a serotype of AAV2, AAV6, AAV8, or AAV9. In some embodiments, the recombinant viruses are injected directly into target tissues. In alternative embodiments, the recombinant viruses are delivered systemically via the circulatory system. It is known in the art that different AAVs tend to localize to different tissues. In liver target tissues, effective transduction of hepatocytes has been shown, for example, with AAV serotypes 2, 8, and 9 (Sands (2011) Methods Mol. Biol. 807:141-157). Accordingly, in some embodiments, the AAV serotype is AAV2. In alternative embodiments, the AAV serotype is AAV6. In other embodiments, the AAV serotype is AAV8. In still other embodiments, the AAV serotype is AAV9. AAVs can also be self-complementary such that they do not require second-strand DNA synthesis in the host cell (McCarty, et al. (2001) Gene Ther. 8:1248-54). Nucleic acid molecules delivered by recombinant AAVs can include left (5') and right (3') inverted terminal repeats.

In one embodiment, a recombinant virus used for meganuclease gene delivery is a self-limiting recombinant virus. A self-limiting virus can have limited persistence time in a cell or organism due to the presence of a recognition sequence for an engineered meganuclease within the viral genome. Thus, a self-limiting recombinant virus can be engineered to provide coding for a promoter, a meganuclease described herein, and a meganuclease recognition site within the ITRs. The self-limiting recombinant virus delivers the meganuclease gene to a cell, tissue, or organism, such that the meganuclease is expressed and able to cut the genome of the cell at an endogenous recognition sequence within the genome. The delivered meganuclease will also find its target site within the self-limiting recombinant viral genome, and cut the recombinant viral genome at this target site. Once cut, the 5' and 3' ends of the viral genome will be exposed and degraded by exonucleases, thus killing the virus and ceasing production of the meganuclease.

If the meganuclease genes are delivered in DNA form (e.g. plasmid) and/or via a recombinant virus (e.g. AAV) they can be operably linked to a promoter. In some embodiments, this can be a viral promoter such as endogenous promoters from the recombinant virus (e.g. the LTR of a lentivirus) or the well-known cytomegalovirus- or SV40 virus-early promoters. In a particular embodiment, nuclease genes are operably linked to a promoter that drives gene expression preferentially in the target cells. Examples of liver-specific promoters include, without limitation, the human alpha-1 antitrypsin promoter, hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter.

In some embodiments, a subject is administered a pharmaceutical composition at a dose of about $1\times10^{10}$ gc/kg to about $1\times10^{14}$ gc/kg (e.g., $1\times10^{10}$ gc/kg, $1\times10^{11}$ gc/kg, $1\times10^{12}$ gc/kg, $1\times10^{13}$ gc/kg, or $1\times10^{14}$ gc/kg) of a polynucleotide comprising a nucleic acid sequence encoding an engineered nuclease. In some embodiments, a subject is administered a pharmaceutical composition at a dose of at least about $1\times10^{10}$ gc/kg, at least about $1\times10^{11}$ gc/kg, at least about $1\times10^{12}$ gc/kg, at least about $1\times10^{13}$ gc/kg, or at least about $1\times10^{14}$ gc/kg of a polynucleotide comprising a nucleic acid sequence encoding an engineered nuclease. In some embodiments, a subject is administered a pharmaceutical composition at a dose of about $1\times10^{10}$ gc/kg to about $1\times10^{11}$ gc/kg, about $1\times10^{11}$ gc/kg to about $1\times10^{12}$ gc/kg, about $1\times10^{12}$ gc/kg to about $1\times10^{13}$ gc/kg, or about $1\times10^{13}$ gc/kg to about $1\times10^{14}$ gc/kg of a polynucleotide comprising a nucleic acid sequence encoding an engineered nuclease. In certain embodiments, a subject is administered a pharmaceutical composition at a dose of about $1\times10^{12}$ gc/kg to about $9\times10^{13}$ gc/kg (e.g., about $1\times10^{12}$ gc/kg, about $2\times10^{12}$ gc/kg, about $3\times10^{12}$ gc/kg, about $4\times10^{12}$ gc/kg, about $5\times10^{12}$ gc/kg, about $6\times10^{12}$ gc/kg, about $7\times10^{12}$ gc/kg, about $8\times10^{12}$ gc/kg, about $9\times10^{12}$ gc/kg, about $1\times10^{13}$ gc/kg, about $2\times10^{13}$ gc/kg, about $3\times10^{13}$ gc/kg, about $4\times10^{13}$ gc/kg, about $5\times10^{13}$ gc/kg, about $6\times10^{13}$ gc/kg, about $7\times10^{13}$ gc/kg, about $8\times10^{13}$ gc/kg, or about $9\times10^{13}$ gc/kg) of a polynucleotide comprising a nucleic acid sequence encoding an engineered nuclease.

In some embodiments, a subject is administered a lipid nanoparticle formulation at a dose of about 0.1 mg/kg to about 3 mg/kg of mRNA encoding an engineered nuclease. In some embodiments, the subject is administered a lipid nanoparticle formulation at a dose of at least about 0.1 mg/kg, at least about 0.25 mg/kg, at least about 0.5 mg/kg, at least about 0.75 mg/kg, at least about 1.0 mg/kg, at least about 1.5 mg/kg, at least about 2.0 mg/kg, at least about 2.5 mg/kg, or at least about 3.0 mg/kg of mRNA encoding an engineered nuclease. In some embodiments, the subject is administered a lipid nanoparticle formulation at a dose of within about 0.1 mg/kg to about 0.25 mg/kg, about 0.25 mg/kg to about 0.5 mg/kg, about 0.5 mg/kg to about 0.75 mg/kg, about 0.75 mg/kg to about 1.0 mg/kg, about 1.0 mg/kg to about 1.5 mg/kg, about 1.5 mg/kg to about 2.0 mg/kg, about 2.0 mg/kg to about 2.5 mg/kg, or about 2.5 mg/kg to about 3.0 mg/kg of mRNA encoding an engineered nuclease.

The target tissue(s) for delivery of engineered meganucleases of the invention include, without limitation, cells of the liver, such as a hepatocyte cell or preferably a primary hepatocyte, more preferably a human hepatocyte or a human primary hepatocyte, a HepG2.2.15 or a HepG2-hNTCP cell. As discussed, meganucleases of the invention can be delivered as purified protein or as RNA or DNA encoding the meganuclease. In one embodiment, meganuclease proteins, or mRNA, or DNA vectors encoding meganucleases, are supplied to target cells (e.g., cells in the liver) via injection directly to the target tissue. Alternatively, meganuclease protein, mRNA, DNA, or cells expressing meganucleases can be delivered systemically via the circulatory system.

Methods and compositions are provided for delivering a nuclease disclosed herein to the liver of a subject. In one embodiment, native hepatocytes, which have been removed from the mammal, can be transduced with a vector encoding the engineered nuclease. Alternatively, native hepatocytes of the subject can be transduced ex vivo with a recombinant virus, such as a recombinant AAV, which encodes the engineered nuclease and/or a molecule that stimulates liver regeneration, such as a hepatotoxin. Preferably the hepatotoxin is uPA and has been modified to inhibit its secretion from the hepatocyte once expressed by the recombinant virus. In another embodiment, the recombinant virus comprises a nucleic acid sequence encoding tPA, which can stimulate hepatocyte regeneration de novo. The transduced hepatocytes, which have been removed from the mammal, can then be returned to the mammal where conditions are provided that are conducive to expression of the engineered nuclease. Typically the transduced hepatocytes can be returned to the patient by infusion through the spleen or portal vasculature, and administration may be single or multiple over a period of 1 to 5 or more days.

In an in vivo aspect of the methods of the invention, a retrovirus, pseudotype, or recombinant AAV is constructed, which encodes the engineered nuclease and is administered to the subject. Administration of a recombinant virus comprising a nucleic acid sequence encoding the engineered nuclease can occur, for example, with administration of a recombinant AAV that comprises a nucleic acid sequence encoding a secretion-impaired hepatotoxin, or encoding tPA, which stimulates hepatocyte regeneration without acting as a hepatotoxin.

In various embodiments of the methods described herein, the one or more engineered nucleases, polynucleotides comprising nucleic acid sequences encoding such engineered nucleases, or recombinant viruses comprising one or more polynucleotides comprising a nucleotide sequence encoding such engineered nucleases, as described herein, can be administered via any suitable route of administration known in the art. Accordingly, the one or more engineered nucleases, polynucleotides encoding such engineered nucleases, or vectors comprising one or more polynucleotides encoding such engineered nucleases, as described herein may be administered by an administration route comprising intravenous, intramuscular, intraperitoneal, subcutaneous, intrahepatic, transmucosal, transdermal, intraarterial, and sublingual. In some embodiments, nuclease proteins, or mRNA, or DNA vectors encoding nucleases, are supplied to target cells (e.g., cells in the liver) via injection directly to the target tissue. Other suitable routes of administration of the engineered nucleases, polynucleotides encoding such engineered nucleases, or recombinant viruses comprising one or more polynucleotides encoding such engineered nucleases may be readily determined by the treating physician as necessary.

In some embodiments, a therapeutically effective amount of an engineered nuclease described herein is administered to a subject in need thereof. As appropriate, the dosage or dosing frequency of the engineered nuclease may be adjusted over the course of the treatment, based on the judgment of the administering physician. Appropriate doses will depend, among other factors, on the specifics of any AAV chosen (e.g., serotype, etc.), on the route of administration, on the subject being treated (i.e., age, weight, sex, and general condition of the subject), and the mode of administration. Thus, the appropriate dosage may vary from patient to patient. An appropriate effective amount can be readily determined by one of skill in the art. Dosage treatment may be a single dose schedule or a multiple dose schedule. Moreover, the subject may be administered as many doses as appropriate. One of skill in the art can readily determine an appropriate number of doses. The dosage may need to be adjusted to take into consideration an alternative route of administration or balance the therapeutic benefit against any side effects.

In some embodiments, the methods comprise delivering an engineered meganuclease described herein (or a polynucleotide comprising a nucleic acid sequence encoding the same) and a polynucleotide comprising a nucleic acid sequence encoding a sequence of interest and nucleic acid sequences homologous to nucleic acid sequences flanking the meganuclease cleavage site, wherein the engineered meganuclease recognizes and cleaves a recognition sequence comprising SEQ ID NO: 7 or SEQ ID NO: 9 within a TTR gene, thus cleaving the TTR gene, wherein the sequence of interest is inserted at the cleavage site by homologous recombination.

Exogenous nucleic acid molecules of the invention may be introduced into a cell and/or delivered to a subject by any of the means previously discussed. In a particular embodiment, exogenous nucleic acid molecules are introduced by way of a recombinant virus (i.e., a viral vector), such as a recombinant lentivirus, recombinant retrovirus, recombinant adenovirus, or a recombinant AAV. Recombinant AAV useful for introducing an exogenous nucleic acid molecule can have any serotype that allows for transduction of the virus into the cell and insertion of the exogenous nucleic acid molecule sequence into the cell genome. In some embodiments, the recombinant AAV has a serotype of AAV2, AAV6, AAV8, or AAV9. In some embodiments, the recombinant AAV has a serotype of AAV2. In some embodiments, the recombinant AAV has a serotype of AAV6. In some embodiments, the recombinant AAV has a serotype of AAV8. The recombinant AAV can also be self-complementary such that it does not require second-strand DNA synthesis in the host cell. Exogenous nucleic acid molecules introduced using a recombinant AAV can be flanked by a 5' (left) and 3' (right) inverted terminal repeat.

In another particular embodiment, an exogenous nucleic acid molecule can be introduced into a cell using a single-stranded DNA template. The single-stranded DNA can comprise the exogenous nucleic acid molecule and, in particular embodiments, can comprise 5' and 3' homology arms to promote insertion of the nucleic acid sequence into the nuclease cleavage site by homologous recombination. The single-stranded DNA can further comprise a 5' AAV inverted terminal repeat (ITR) sequence 5' upstream of the 5' homology arm, and a 3' AAV ITR sequence 3' downstream of the 3' homology arm.

In another particular embodiment, genes encoding a nuclease of the invention and/or an exogenous nucleic acid molecule of the invention can be introduced into a cell by transfection with a linearized DNA template. A plasmid DNA encoding an engineered nuclease and/or an exogenous nucleic acid molecule can, for example, be digested by one or more restriction enzymes such that the circular plasmid DNA is linearized prior to transfection into the cell.

When delivered to a cell, an exogenous nucleic acid of the invention can be operably linked to any promoter suitable for expression of the encoded polypeptide in the cell, including those mammalian promoters and inducible promoters previously discussed. An exogenous nucleic acid of the invention can also be operably linked to a synthetic promoter. Synthetic promoters can include, without limitation, the JeT promoter (WO 2002/012514). In specific embodiments, a nucleic acid sequence encoding an engineered meganuclease as disclosed herein can be operably linked to a liver-specific promoter. Examples of liver-specific promoters include, without limitation, human alpha-1 antitrypsin promoter and apolipoprotein A-II promoter.

2.4 Pharmaceutical Compositions

In some embodiments, the invention provides a pharmaceutical composition comprising a pharmaceutically acceptable carrier and an engineered meganuclease of the invention, or a pharmaceutically acceptable carrier and an isolated polynucleotide comprising a nucleic acid encoding an engineered meganuclease of the invention. In other embodiments, the invention provides a pharmaceutical composition comprising a pharmaceutically acceptable carrier and a genetically-modified cell of the invention, which can be delivered to a target tissue where the cell expresses the engineered meganuclease as disclosed herein. In particular, pharmaceutical compositions are provided that comprise a pharmaceutically acceptable carrier and a therapeutically effective amount of a nucleic acid encoding an engineered meganuclease or an engineered meganuclease, wherein the engineered nuclease has specificity for a recognition sequence within a TTR gene, such as TTR 5-6 (SEQ ID NO: 9) or TTR 15-16 (SEQ ID NO: 7).

Accordingly, pharmaceutical compositions of the invention can be useful for treating TTR-associated diseases (e.g., transthyretin amyloidosis), reducing the level of TTR, reducing the level of TTR amyloids, or reducing the symptoms associated with TTR-associated diseases (e.g., transthyretin amyloidosis) in a subject. A subject having TTR-associated diseases or a subject who may be particularly receptive to treatment with the engineered meganucleases herein may be identified by ascertaining the presence or absence of one or more risk factors, diagnostic, or prognostic indicators, such as those described herein. For example, in some instances, the subject has a mutation in a TTR gene that affects the peripheral nervous system, the autonomic nervous system, the leptomeninges, and/or the heart. In certain instances, the subject undergoing treatment in accordance with the methods and compositions provided herein can be characterized by one or more (e.g., 1, 2, 3, 4, 5, 6, 7, 8, 9, 10, 15, 20, 25, or more) mutations in the TTR gene. For example, the subject undergoing treatment has a mutation in a TTR gene encoding a TTR polypeptide comprising one or more amino acid substitutions comprising a Gly6Ser, Cys10Arg, Leu12Pro, Asp18Gly, Val20Ile, Ala25Thr, Val30Met, Val30Ala, Val30Leu, Val30Gly, Phe33Ile, Phe33Leu, Ala36Pro, Glu42Gly, Phe44Ser, Ala45Thr, Gly47Arg, Gly47Ala, Gly47Arg, Thr49Ala, Ser50Arg, Ser50Ile, Gly53Glu, Leu55Pro, Leu58His, Leu58Arg, Thr60Ala, Glu61Lys, Phe64Leu, Phe64Ser, Ile68Leu, Tyr69His, Lys70Asn, Val71Ala, Ser77Tyr, Ile84Ser, Glu89Gln, His90Asn, Ala97Gly, Ala97Ser, Arg104His, Ile107Val, Ala109Thr, Ala109Val, Leu111Met, Tyr114Cys, Tyr114His, Tyr116Val, Thr119Met, Val122Ile, or a Val122Del mutation.

TTR levels can be assessed any time before, during, or after treatment in accordance with the methods herein using any methods known in the art. TTR levels may be assessed based on the level of any variable associated with TTR gene expression, e.g., TTR mRNA level, TTR protein level, retinol binding protein level, vitamin A level, or the number or extent of amyloid deposits. Reduction of TTR levels or expression may be assessed by a decrease in an absolute or relative level of one or more of these variables compared with a reference level. TTR levels may be measured in a biological sample isolated from a subject, such as a tissue biopsy or a bodily fluid including blood, serum, plasma, cerebrospinal fluid, or urine. Optionally, TTR levels are normalized to a standard protein or substance in the sample. In some embodiments, the claimed methods include administration of any of the engineered meganucleases described herein, or nucleic acids encoding the meganucleases, to reduce TTR levels in a subject, by at least 1%, 2%, 3%, 4%, 5%, 10%, 15%, 20%, 25%, 30%, 40%, 50%, 60%, 70%, 80%, 90%, 95%, or 100% relative to a reference level.

Such pharmaceutical compositions can be prepared in accordance with known techniques. See, e.g., Remington, The Science And Practice of Pharmacy (21st ed., Philadelphia, Lippincott, Williams & Wilkins, 2005). In the manufacture of a pharmaceutical formulation according to the invention, meganuclease polypeptides (or DNA/RNA encoding the same or cells expressing the same) are typically admixed with a pharmaceutically acceptable carrier and the resulting composition is administered to a subject. The carrier must be acceptable in the sense of being compatible with any other ingredients in the formulation and must not be deleterious to the subject. In some embodiments, pharmaceutical compositions of the invention can further comprise one or more additional agents or biological molecules useful in the treatment of a disease in the subject. Likewise, the additional agent(s) and/or biological molecule(s) can be co-administered as a separate composition.

The pharmaceutical compositions described herein can include an effective amount of any meganuclease, or nucleic acid encoding any meganuclease, of the invention. In some embodiments, the pharmaceutical composition comprises about $1\times10^{10}$ gc/kg to about $1\times10^{14}$ gc/kg (e.g., $1\times10^{10}$ gc/kg, $1\times10^{11}$ gc/kg, $1\times10^{12}$ gc/kg, $1\times10^{13}$ gc/kg, or $1\times10^{14}$ gc/kg) of a polynucleotide comprising a nucleic acid sequence encoding the engineered nuclease. In some embodiments, the pharmaceutical composition comprises at least about $1\times10^{10}$ gc/kg, at least about $1\times10^{11}$ gc/kg, at least about $1\times10^{12}$ gc/kg, at least about $1\times10^{13}$ gc/kg, or at least about $1\times10^{14}$ gc/kg of a polynucleotide comprising a nucleic acid sequence encoding the engineered nuclease. In some embodiments, the pharmaceutical composition comprises about $1\times10^{10}$ gc/kg to about $1\times10^{11}$ gc/kg, about $1\times10^{11}$ gc/kg to about $1\times10^{12}$ gc/kg, about $1\times10^{12}$ gc/kg to about $1\times10^{13}$ gc/kg, or about $1\times10^{13}$ gc/kg to about $1\times10^{14}$ gc/kg of a polynucleotide comprising a nucleic acid sequence encoding the engineered nuclease. In certain embodiments, the pharmaceutical composition comprises about $1\times10^{12}$ gc/kg to about $9\times10^{13}$ gc/kg (e.g., about $1\times10^{12}$ gc/kg, about $2\times10^{12}$ gc/kg, about $3\times10^{12}$ gc/kg, about $4\times10^{12}$ gc/kg, about $5\times10^{12}$ gc/kg, about $6\times10^{12}$ gc/kg, about $7\times10^{12}$ gc/kg, about $8\times10^{2}$ gc/kg, about $9\times10^{12}$ gc/kg, about $1\times10^{13}$ gc/kg, about $2\times10^{13}$ gc/kg, about $3\times10^{13}$ gc/kg, about $4\times10^{13}$ gc/kg, about $5\times10^{13}$ gc/kg, about $6\times10^{13}$ gc/kg, about $7\times10^{13}$ gc/kg, about $8\times10^{13}$ gc/kg, or about $9\times10^{13}$ gc/kg) of a polynucleotide comprising a nucleic acid sequence encoding the engineered meganuclease.

In particular embodiments of the invention, the pharmaceutical composition can comprise one or more mRNAs described herein encapsulated within lipid nanoparticles, which are described elsewhere herein. In particular embodiments, lipid nanoparticles can comprise two or more mRNAs described herein. In other embodiments, lipid nanoparticles can comprise at least two mRNAs, wherein at least a first mRNA is an mRNA described herein that encodes an engineered meganuclease described herein that recognizes and cleaves the TTR 5-6 recognition sequence, and wherein at least a second mRNA encodes a second engineered meganuclease that recognizes and cleaves a recognition sequence within TTR gene other than the TTR 5-6 recognition sequence (e.g., TTR 15-16).

Some lipid nanoparticles contemplated for use in the invention comprise at least one cationic lipid, at least one non-cationic lipid, and at least one conjugated lipid. In more particular examples, lipid nanoparticles can comprise from about 50 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology. In other particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate and are produced in such a manner as to have a non-lamellar (i.e., non-bilayer) morphology.

Cationic lipids can include, for example, one or more of the following: palmitoyi-oleoyl-nor-arginine (PONA), MPDACA, GUADACA, ((6Z,9Z,28Z,31Z)-heptatriaconta-6,9,28,31-tetraen-19-yl 4-(dimethylamino)butanoate) (MC3), LenMC3, CP-LenMC3, T-LenMC3, CP-T-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2 (spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. The cationic lipid can also be DLinDMA, DLin-K-C2-DMA ("XTC2"), MC3, LenMC3, CP-LenMC3, 7-LenMC3, CP-7-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid may comprise from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid may comprise from about 40 mol % to about 90 mol %, from about 40 mol % to about 85 mol %, from about 40 mol % to about 80 mol % from about 40 mol % to about 75 mol %, from about 40 mol % to about 70 mol %, from about 40 mol % to about 65 mol %, or from about 40 mol % to about 60 mol % of the total lipid present in the particle.

The non-cationic lipid may comprise, e.g., one or more anionic lipids and/or neutral lipids. In particular embodiments, the non-cationic lipid comprises one of the following neutral lipid components: (1) cholesterol or a derivative thereof; (2) a phospholipid; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

The conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one particular embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-di lauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676. Yet additional PEG-lipid conjugates suitable for use in the invention include, without limitation, 1-[8'-(1,2-dimyristoyl-3-propanoxy)-carboxamido-3',6'-dioxaoctanyl]carbamoyl-ω-methyl-poly(ethylene glycol) (2KPEG-DMG). The synthesis of 2KPEG-DMG is described in U.S. Pat. No. 7,404,969.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In other embodiments, the composition may comprise amphoteric liposomes, which contain at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

Cationic compounds useful for amphoteric liposomes include those cationic compounds previously described herein above. Without limitation, strongly cationic compounds can include, for example: DC-Chol 3-β-[N—(N',N'-dimethylmethane) carbamoyl] cholesterol, TC-Chol 3-β-[N—(N',N',N'-trimethylaminoethane) carbamoyl cholesterol, BGSC bisguanidinium-spermidine-cholesterol, BGTC bis-guadinium-tren-cholesterol, DOTAP (1,2-dioleoyloxypropyl)-N,N,N-trimethylammonium chloride, DOSPER (1,3-dioleoyloxy-2-(6-carboxy-spermyl)-propylarnide, DOTMA (1,2-dioleoyloxypropyl)-N,N,N-trimethylamronium chloride) (Lipofectin®), DORIE 1,2-dioleoyloxypropyl)-3-dimethylhydroxyethylammonium bromide, DOSC (1,2-dioleoyl-3-succinyl-sn-glyceryl choline ester), DOGSDSO (1,2-dioleoyl-sn-glycero-3-succinyl-2-hydroxyethyl disulfide omithine), DDAB dimethyldioctadecylammonium bromide, DOGS ((C18)2GlySper3+) N,N-dioctadecylamido-glycol-spermin (Transfectam®) (C18)2Gly+N, N-dioctadecylamido-glycine, CTAB cetyltrimethylarnmonium bromide, CpyC cetylpyridinium chloride, DOEPC 1,2-dioleoly-sn-glycero-3-ethylphosphocholine or other O-alkyl-phosphatidylcholine or ethanolamines, amides from lysine, arginine or ornithine and phosphatidyl ethanolamine.

Examples of weakly cationic compounds include, without limitation: His-Chol (histaminyl-cholesterol hemisuccinate), Mo-Chol (morpholine-N-ethylamino-cholesterol hemisuccinate), or histidinyl-PE.

Examples of neutral compounds include, without limitation: cholesterol, ceramides, phosphatidyl cholines, phosphatidyl ethanolamines, tetraether lipids, or diacyl glycerols.

Anionic compounds useful for amphoteric liposomes include those non-cationic compounds previously described herein. Without limitation, examples of weakly anionic compounds can include: CHEMS (cholesterol hemisuccinate), alkyl carboxylic acids with 8 to 25 carbon atoms, or diacyl glycerol hemisuccinate. Additional weakly anionic compounds can include the amides of aspartic acid, or glutamic acid and PE as well as PS and its amides with glycine, alanine, glutamine, asparagine, serine, cysteine, threonine, tyrosine, glutamic acid, aspartic acid or other amino acids or aminodicarboxylic acids. According to the same principle, the esters of hydroxycarboxylic acids or hydroxydicarboxylic acids and PS are also weakly anionic compounds.

In some embodiments, amphoteric liposomes may contain a conjugated lipid, such as those described herein above. Particular examples of useful conjugated lipids include, without limitation, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particular examples are PEG-modified diacylglycerols and dialkylglycerols.

In some embodiments, the neutral lipids may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

Considering the total amount of neutral and conjugated lipids, the remaining balance of the amphoteric liposome can comprise a mixture of cationic compounds and anionic compounds formulated at various ratios. The ratio of cationic to anionic lipid may selected in order to achieve the desired properties of nucleic acid encapsulation, zeta potential, pKa, or other physicochemical property that is at least in part dependent on the presence of charged lipid components.

In some embodiments, the lipid nanoparticles have a composition, which specifically enhances delivery and uptake in the liver, and specifically within hepatocytes.

In some embodiments, pharmaceutical compositions of the invention can further comprise one or more additional agents useful in the treatment of TTR-associated diseases (e.g., transthyretin amyloidosis) in the subject.

The present disclosure also provides engineered meganucleases described herein (or nucleic acids encoding the same or cells expressing the engineered meganucleases) for use as a medicament. The present disclosure further provides the use of an engineered meganuclease described herein (or a nucleic acid encoding the same or cells expressing an engineered meganuclease) in the manufacture of a medicament for treating TTR-associated diseases (e.g., transthyretin amyloidosis), for reducing the level of TTR, for reducing the level of TTR amyloids, or reducing the symptoms associated with TTR-associated diseases (e.g., transthyretin amyloidosis).

2.5 Methods for Producing Recombinant Viruses

In some embodiments, the invention provides recombinant viruses (i.e., recombinant viral vectors; e.g., recombinant AAV vectors) for use in the methods of the invention. Recombinant AAVs are typically produced in mammalian cell lines such as HEK-293. Because the viral cap and rep genes are removed from the recombinant virus to prevent its self-replication to make room for the therapeutic gene(s) to be delivered (e.g. the meganuclease gene), it is necessary to provide these in trans in the packaging cell line. In addition, it is necessary to provide the "helper" (e.g. adenoviral) components necessary to support replication (Cots D et al., (2013) Curr. Gene Ther. 13(5): 370-81). Frequently, recombinant AAVs are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the engineered meganuclease is not expressed in the packaging cells. Because the recombinant viral genomes of the invention may comprise a recognition sequence for the meganuclease, any meganuclease expressed in the packaging cell line may be capable of cleaving the viral genome before it can be packaged into viral particles. This will result in reduced packaging efficiency and/or the packaging of fragmented genomes. Several approaches can be used to prevent meganuclease expression in the packaging cells.

The nuclease can be placed under the control of a tissue-specific promoter that is not active in the packaging cells. For example, if a recombinant virus is developed for delivery of (a) meganuclease gene(s) to muscle tissue, a muscle-specific promoter can be used. Examples of muscle-specific promoters include C5-12 (Liu, et al. (2004) Hum Gene Ther. 15:783-92), the muscle-specific creatine kinase (MCK) promoter (Yuasa, et al. (2002) Gene Ther. 9:1576-88), or the smooth muscle 22 (SM22) promoter (Haase, et al. (2013) BMC Biotechnol. 13:49-54). Examples of CNS (neuron)-specific promoters include the NSE, Synapsin, and MeCP2 promoters (Lentz, et al. (2012) Neurobiol Dis. 48:179-88). Examples of liver-specific promoters include albumin promoters (such as Palb), human al-antitrypsin (such as PalAT), and hemopexin (such as Phpx) (Kramer et al., (2003) Mol. Therapy 7:375-85), hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter. Examples of eye-specific promoters include opsin, and corneal epithelium-specific K12 promoters (Martin et al. (2002) Methods (28): 267-75) (Tong et al., (2007) J Gene Med, 9:956-66). These promoters, or other tissue-specific promoters known in the art, are not highly-active in HEK-293 cells and, thus, will not be expected to yield significant levels of meganuclease gene expression in packaging cells when incorporated into viral vectors of the present invention. Similarly, the recombinant viruses of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASB5 (muscle), PPP1R12B (heart), SLC5A12 (kidney), cholesterol regulation APOM (liver), ADPRHL1 (heart), and monogenic malformation syndromes TP73L (muscle). (Jacox et al., (2010), PLoS One v.5(8):e12274).

Alternatively, the recombinant virus can be packaged in cells from a different species in which the meganuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a particular embodiment, viral particles are produced in insect cells using the baculovirus system as described by Gao, et al. (Gao et al. (2007), J. Biotechnol. 131(2):138-43). A meganuclease under the control of a mammalian promoter is unlikely to be expressed in these cells (Airenne et al. (2013), Mol. Ther. 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of a meganuclease. Because these introns are not spliced efficiently from pre-mRNA transcripts in insect cells, insect cells will not express a functional meganuclease and will package the full-length genome. In contrast, mammalian cells to which the resulting recombinant AAV particles are delivered will properly splice the pre-mRNA and will express functional meganuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen, H (2012) Mol Ther Nucleic Acids. 1(11): e57).

The meganuclease gene can be operably linked to an inducible promoter such that a small-molecule inducer is required for meganuclease expression. Examples of inducible promoters include the Tet-On system (Clontech; Chen et al. (2015), BMC Biotechnol. 15(1):4)) and the RheoSwitch system (Intrexon; Sowa et al. (2011), Spine, 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the meganuclease gene under the control of a promoter that responds to the corresponding transcription factor, the meganuclease gene having (a) binding site(s) for the transcription factor; and 2) including the gene encoding the transcription factor in the packaged viral genome The latter step is necessary because the meganuclease will not be expressed in the target cells or tissues following recombinant AAV delivery if the transcription activator is not also provided to the same cells. The transcription activator then induces meganuclease gene expression only in cells or tissues that are treated with the cognate small-molecule activator. This approach is advantageous because it enables meganuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

In another particular embodiment, recombinant AAV particles are produced in a mammalian cell line that expresses a transcription repressor that prevents expression of the meganuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the meganuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang and Roninson (1996), Gene 183:137-42). The use of a non-human transcription repressor ensures that transcription of the meganuclease gene will be repressed only in the packaging cells expressing the repressor and not in target cells or tissues transduced with the resulting recombinant AAV.

2.6 Engineered Meganuclease Variants

Embodiments of the invention encompass the engineered meganucleases described herein, and variants thereof. Further embodiments of the invention encompass isolated polynucleotides comprising a nucleic acid sequence encoding the meganucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to bind and cleave the TTR 5-6 recognition sequence (SEQ ID NO: 7) within the TTR gene or TTR 15-16 recognition sequence (SEQ ID NO: 9). Such variants may result, for example, from human manipulation. Biologically active variants of a native polypeptide of the embodiments (e.g., SEQ ID NOs: 11-15), or biologically active variants of the recognition half-site binding subunits described herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide, native subunit, native HVR1 region, and/or native HVR2 region, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

In some embodiments, engineered meganucleases of the invention can comprise variants of the HVR1 and HVR2 regions disclosed herein. Parental HVR regions can comprise, for example, residues 24-79 or residues 215-270 of the exemplified engineered meganucleases. Thus, variant HVRs can comprise an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 24-79 or residues 215-270 of the engineered meganucleases exemplified herein, such that the variant HVR regions maintain the biological activity of the engineered meganuclease (i.e., binding to and cleaving the recognition sequence). Further, in some embodiments of the invention, a variant HVR1 region or variant HVR2 region can comprise residues corresponding to the amino acid residues found at specific positions within the parental HVR. In this context, "corresponding to" means that an amino acid residue in the variant HVR is the same amino acid residue (i.e., a separate identical residue) present in the parental HVR sequence in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative (i.e., corresponding) to parental position 26. to parental position 26.

In particular embodiments, engineered meganucleases of the invention comprise an HVR1 that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 24-79 of any one of SEQ ID NOs: 11-15.

at least 91%, at least 92%, at least 93%, at least 94%, at least 95%, at least 96%, at least 97%, at least 98%, at least 99%, or more sequence identity to an amino acid sequence corresponding to residues 215-270 of any one of SEQ ID NOs: 11-15.

A substantial number of amino acid modifications to the DNA recognition domain of the wild-type I-CreI meganuclease have previously been identified (e.g., U.S. Pat. No. 8,021,867), which singly or in combination, result in engineered meganucleases with specificities altered at individual bases within the DNA recognition sequence half-site, such that the resulting rationally-designed meganucleases have half-site specificities different from the wild-type enzyme. Table 3 provides potential substitutions that can be made in an engineered meganuclease monomer or subunit to enhance specificity based on the base present at each half-site position (−1 through −9) of a recognition half-site.

TABLE 3

| | Favored Sense-Strand Base | | | | | | | | | | |
|---|---|---|---|---|---|---|---|---|---|---|---|
| Posn. | A | C | G | T | A/T | A/C | A/G | C/T | G/T | A/G/T | A/C/G/T |
| −1 | Y75<br>L75*<br>C75*<br>Y139*<br>C46*<br>A46* | **R70***<br>H75*<br>R75*<br>H46*<br>K46*<br>R46* | K70<br>E70*<br>E75*<br>E46*<br>D46* | Q70*<br>C70<br>L70<br>Y75*<br>Q75*<br>H75*<br>H139<br>Q46*<br>H46* | | | | **T46*** | | | G70<br>A70<br>S70<br>G46* |
| −2 | Q70<br>T44*<br>A44*<br>V44*<br>I44*<br>L44*<br>N44* | E70<br>D70<br>K44*<br>R44* | H70<br>D44*<br>E44* | **Q44*** | C44* | | | | | | |
| −3 | Q68<br>C24*<br>**I24*** | E68<br>F68<br>K24*<br>R24* | **R68** | M68<br>C68<br>L68<br>F68 | | H68 | | Y68 | K68 | | |
| −4 | A26*<br>Q77 | E77<br>K26* | R77<br>E26* | | | | | S77<br>**Q26*** | | | S26* |
| −5 | | E42 | R42 | | | **K28*** | C28*<br>Q42 | | | | M66<br>K66 |
| −6 | Q40<br>C28* | E40<br>R28* | R40 | C40<br>I40<br>V40<br>C79<br>I79<br>V79<br>Q28* | A40<br>A79<br>A28*<br>H28* | | | | | | **S40**<br>S28* |
| −7 | **N30*** | E38<br>K30* | K38 | I38 | | | C38 | | | | H38<br>N38 |
| | **Q38** | R30* | R38<br>E30* | L38 | | | | | | | Q30* |
| −8 | F33<br>**Y33** | E33<br>D33 | F33<br>H33 | L33<br>V33<br>I33<br>F33<br>C33 | | R32* | R33 | | | | |
| −9 | | E32 | R32<br>K32 | L32<br>V32<br>A32<br>C32 | | | | D32<br>I32 | | | **S32**<br>N32<br>H32<br>Q32<br>T32 |

Bolded entries are wild-type contact residues and do not constitute "modifications" as used herein. An asterisk indicates that the residue contacts the base on the antisense strand.

In certain embodiments, engineered meganucleases of the invention comprise an HVR2 that has 80%, at least 81%, at least 82%, at least 83%, at least 84%, at least 85%, at least 86%, at least 87%, at least 88%, at least 89%, at least 90%, Certain modifications can be made in an engineered meganuclease monomer or subunit to modulate DNA-binding affinity and/or activity. For example, an engineered meganuclease monomer or subunit described herein can comprise a G, S, or A at a residue corresponding to position 19 of I-CreI or any one of SEQ ID NOs: 11-15 (WO 2009001159), a Y, R, K, or D at a residue corresponding to position 66 of I-CreI or any one of SEQ ID NOs: 11-15, and/or an E, Q, or K at a residue corresponding to position 80 of I-CreI or any one of SEQ ID NOs: 11-15 (U.S. Pat. No. 8,021,867).

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a recombinant nuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide its intended activity. For example, variants of an engineered nuclease would be screened for their ability to preferentially bind and cleave recognition sequences found within a TTR gene.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Characterization of Meganucleases that Bind and Cleave TTR 5-6 Recognition Sequences

1. Meganucleases that Bind and Cleave the TTR 5-6 Recognition Sequence

Recombinant meganucleases that target in the TTR 5-6 recognition site (SEQ ID NO: 15), collectively referred to herein as "TTR 5-6 meganucleases," were engineered to bind and cleave the TTR 5-6 recognition sequence in the human or non-human primate (NHP) genome (SEQ ID NO: 9). Each recognition sequence is present in the TTR gene, specifically within exon 1. Each TTR 5-6 recombinant meganuclease comprises an N-terminal nuclease-localization signal derived from SV40, a first meganuclease subunit, a linker sequence, and a second meganuclease subunit. A first subunit in each TTR 5-6 meganuclease binds to a first TTR 5-6 recognition half-site (SEQ ID NO: 30), while a second subunit binds to a second TTR 5-6 recognition half-site (SEQ ID NO: 32; see, FIG. 1).

The TTR5-6 binding subunits each comprise a 56 base pair hypervariable region, referred to as HVR1 and HVR2, respectively. The HVR1 region of each TTR 5-6 meganuclease binding subunit consists of residues 24-79 of SEQ ID NO: 15. The HVR2 region of each TTR 5-6 meganuclease consists of residues 215-270 of SEQ ID NO: 15. The TTR 5-6 binding regions of SEQ ID NO: 15 are provided as SEQ ID NOs: 24-25.

2. Cleavage of TTR 5-6 Recognition Sequences in a CHO Cell Reporter Assay

Figure 5:
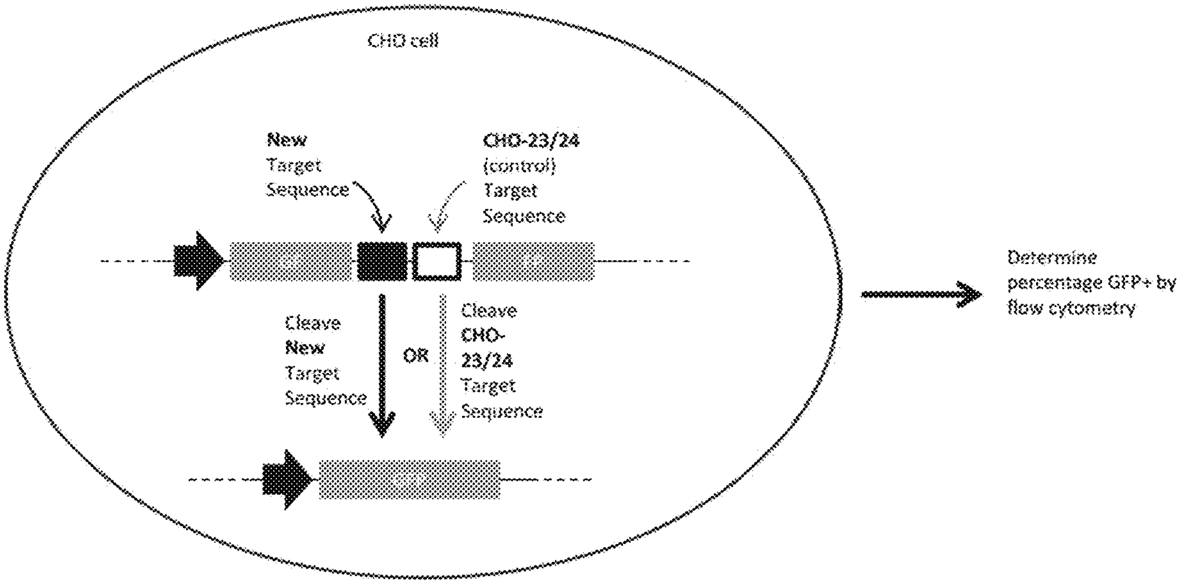
FIG. 5. Schematic of reporter assay in CHO cells for evaluating recombinant meganucleases targeting recognition sequences found in the TTR gene (SEQ ID NO: 3). For the recombinant meganucleases described herein, a CHO cell line was produced in which a reporter cassette was integrated stably into the genome of the cell. The reporter cassette comprised, in 5' to 3' order: an SV40 Early Promoter; the 5' 2/3 of the GFP gene; the recognition sequence for an engineered meganuclease described herein (e.g., the TTR 5-6 or 15-16 recognition sequences); the recognition sequence for the CHO-23/24 meganuclease (WO/2012/167192); and the 3' 2/3 of the GFP gene. Cells stably transfected with this cassette did not express GFP in the absence of a DNA break-inducing agent. Meganucleases were introduced by transduction of an mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.

To determine whether TTR 5-6 meganucleases could bind and cleave both the human and non-human primate 5-6 recognition sequence (SEQ ID NO: 9), each recombinant meganuclease was evaluated using the CHO cell reporter assay previously described (see, WO/2012/167192 and FIG. 5). To perform the assays, CHO cell reporter lines were produced, which carried a non-functional Green Fluorescent Protein (GFP) gene expression cassette integrated into the genome of the cells. The GFP gene in each cell line was interrupted by a pair of recognition sequences such that intracellular cleavage of either recognition sequence by a meganuclease would stimulate a homologous recombination event resulting in a functional GFP gene.

In CHO reporter cell lines developed for this study, one recognition sequence inserted into the GFP gene was the human 5-6 recognition sequence (SEQ ID NO: 9) or a model NHP target sequence (SEQ ID NO: 34). The 5-6 target site in human, mice, and NHP is conserved and identical to SEQ ID NO: 9. However, the immediate upstream genomic sequence in mouse and NHP contains a CpG island, which could represent a potential methylation site that could affect meganuclease binding and cutting. Therefore, the model NHP target sequence (SEQ ID NO: 34) was prepared to determine the efficiency of the 5-6 meganucleases in the GFP reporter assay. The second recognition sequence inserted into the GFP gene was a CHO-23/24 recognition sequence, which is recognized and cleaved by a control meganuclease called "CHO-23/24." CHO reporter cells comprising the human TTR 5-6 recognition sequence and the CHO-23/24 recognition sequence are referred to as "TTR 5-6 h cells." CHO reporter cells comprising the model NHP 5-6 recognition sequence and the CHO-23/24 recognition sequence are referred to as "TTR 5-6nhp cells."

CHO reporter cells were transfected with mRNA encoding the TTR 5-6L.1204 meganuclease. CHO reporter cells were also transfected with mRNA encoding the CHO-23/24 meganuclease. In each assay, 5e4 CHO reporter cells were transfected with 90 ng of mRNA in a 96-well plate using Lipofectamine® MessengerMax (ThermoFisher) according to the manufacturer's instructions. TTR 5-6 h and TTR 5-6nhp cells were evaluated by flow cytometry at 2 days, 5 days, and 7 days post transfection to determine the percentage of GFP-positive cells compared to an untransfected negative control. Data obtained at each time point was normalized to the % GFP positive cells observed using the CHO-23/24 meganuclease to determine an "activity score,"

and the normalized data from the earliest time point was subtracted from that of the latest time point to determine a "toxicity score." The activity and toxicity scores were then added together to determine an "activity index," which was then normalized to the activity index of the CHO-23/24 meganuclease to compare data between cell lines.

3. Results

Figure 6A:
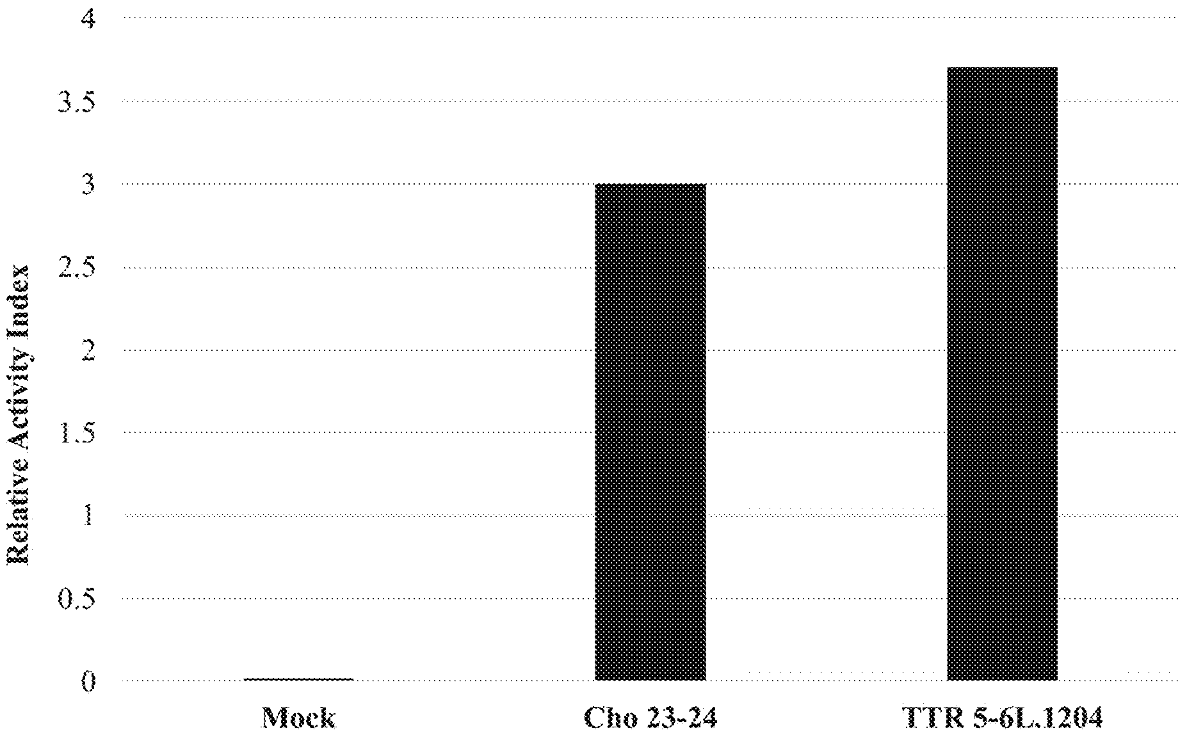
FIGS. 6A and 6B. Efficiency of an engineered TTR5-6 meganuclease described herein for recognizing and cleaving human and non-human primate (NHP) recognition sequences in a CHO cell reporter assay. The activity index represents % GFP positive cells for each cell line expressing the test meganuclease normalized to the cell line expressing the CHO-23/24 meganuclease accounting for the toxicity of the meganuclease.
Figure 6B:
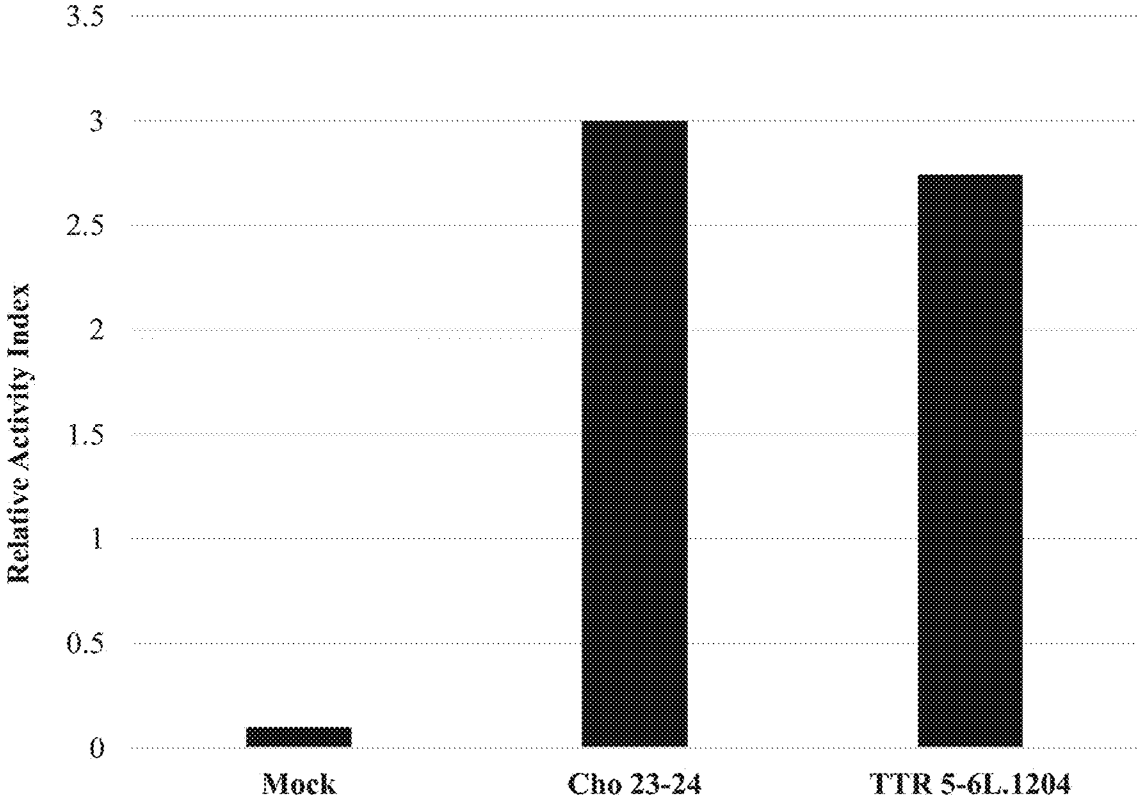

As shown in FIGS. 6A and 6B, the TTR 5-6L.1204 meganuclease cleaved both the human (FIG. 6A) and model NHP (FIG. 6B) recognition sequences with high frequency.

4. Conclusions

These studies demonstrated that an engineered meganuclease targeting the TTR 5-6 recognition site (e.g., meganuclease of SEQ ID NO: 15) encompassed by the invention can efficiently target and cleave their respective recognition sequences in cells having either a human or a model NHP recognition sequence.

Example 2

Characterization of Insertions and Deletions of a Meganuclease that Binds and Cleaves the TTR 5-6 Recognition Sequence 1. Methods In order to evaluate TTR 5-6 nucleases, 1e6 HepG2 cells were electroporated with 500 ng mRNA encoding each TTR nuclease or GFP using the Lonza Amaxa 4D system. Additionally, 7e5 HEK293 cells were electroporated with 700 ng mRNA of TTR nucleases or GFP. Cells were collected at two days post electroporation for gDNA preparation and evaluated for transfection efficiency using a Beckman Coulter CytoFlex S cytometer. Transfection efficiency exceeded 90% for both cell lines. Additional time points were collected at six- and nine-days post electroporation for gDNA extractions. gDNA was prepared using the Macherey Nagel NucleoSpin Blood QuickPure kit.

Digital droplet PCR was utilized to determine the frequency of target insertions and deletions (indel %) at the TTR 5-6 binding site using primers P1, F1, and R1 to generate an amplicon surrounding the binding site, as well as primers P2, F2, R2 to generate a reference amplicon. Amplifications were multiplexed in a 20 μL reaction containing 1×ddPCR Supermix for Probes (no dUTP, BioRad), 250 nM of each probe, 900 nM of each primer, 5 U of HindIII-IF, and about 50 ng cellular gDNA. Droplets were generated using a QX100 droplet generator (BioRad). Cycling conditions were as follows: 1 cycle of 95° C. (2° C./s ramp) for 10 minutes, 45 cycles of 94° C. (2° C./s ramp) for 10 seconds, 60° C. (2° C./s ramp) for 30 seconds, 72 C (2° C./s ramp) for 1 minute, 1 cycle of 98° C. for 10 minutes, 4° C. hold. Droplets were analyzed using a QX200 droplet reader (BioRad) and QuantaSoft analysis software (BioRad) was used to acquire and analyze data. Indel frequencies were calculated by dividing the number of positive copies for the binding site probe by the number of positive copies for the reference probe and comparing loss of FAM+ copies in nuclease-treated cells to mock-transfected cells.

```
P1:
                                        (SEQ ID NO: 35)
56-FAM/TGCTGGACT/ZEN/GGTATTTGTGTCTGA/3IABkFQ

F1:
                                        (SEQ ID NO: 36)
CCACTCATTCTTGGCAGGAT

R1:
                                        (SEQ ID NO: 37)
CACAGAAACACTCACCGTAGG

P2:
                                        (SEQ ID NO: 38)
5HEX/AAATTCCTC/ZEN/CTCAGTTGTGAGCCC/3IABkFQ

F2:
                                        (SEQ ID NO: 39)
AGTCTGGAGAGCTGCAT

R2:
                                        (SEQ ID NO: 40)
CCAGTAAGATTTGGTGTCTATTTC
```

2. Results

Figure 7A:
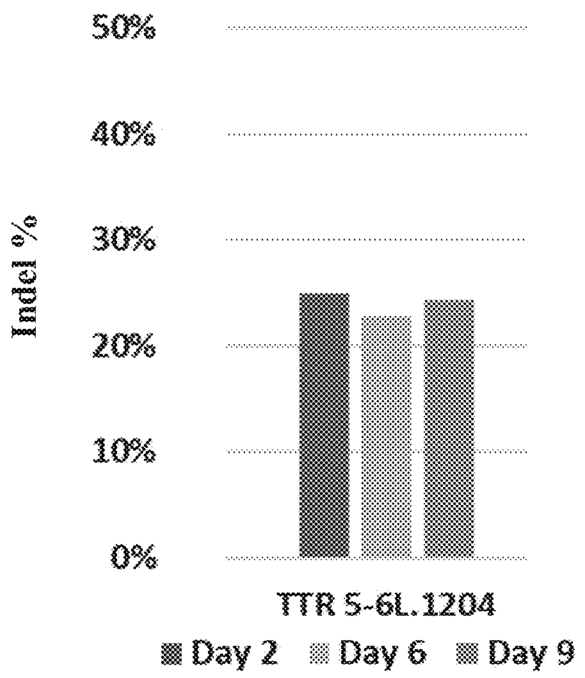
FIGS. 7A and 7B. Bar graph showing the percentage frequency of insertions and deletions (indel) of the tested meganuclease targeting the TTR 5-6 recognition sequence in HepG2 cells (FIG. 7A) and HEK 293 cells (FIG. 7B). The meganuclease was tested at three time points (days 2, 6, and 9) following transfection of the meganuclease.
Figure 7B:
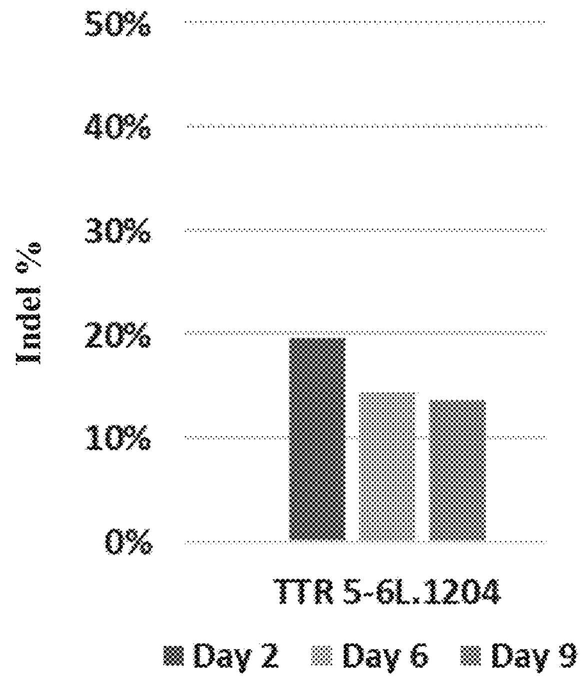
Figure 8:
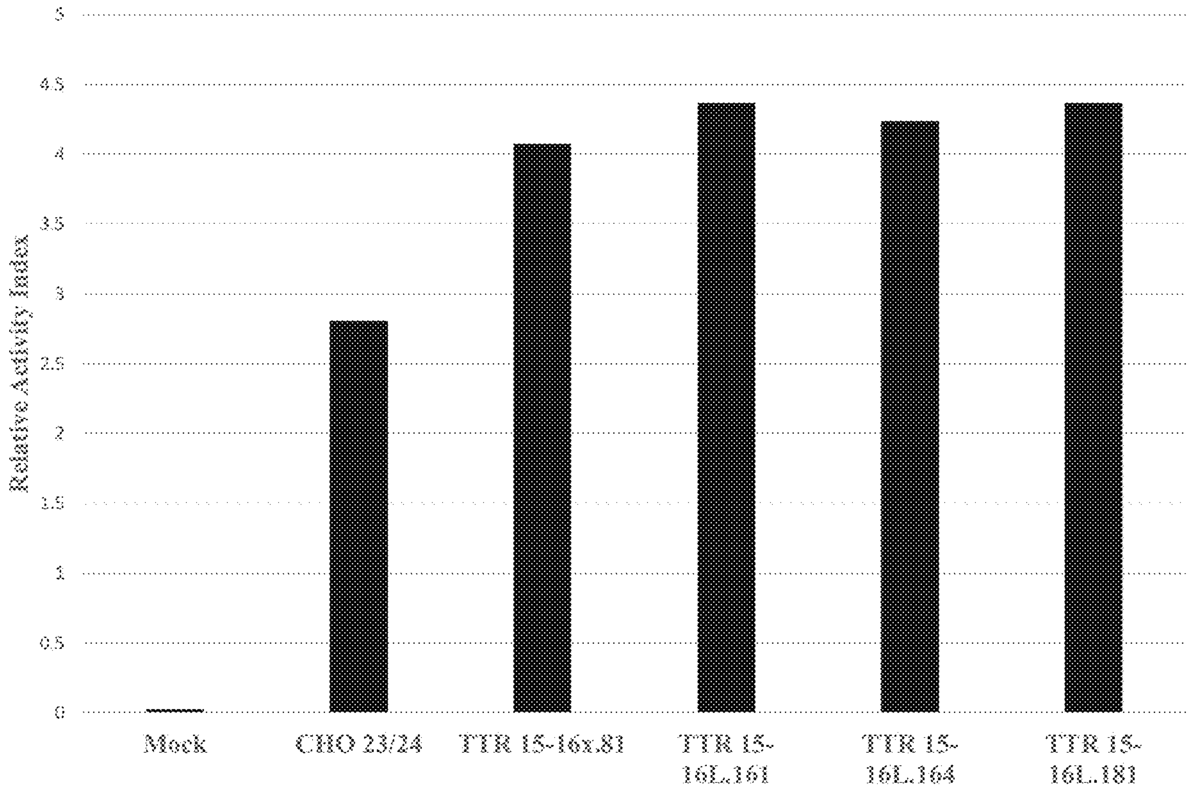
FIG. 8. Efficiency of engineered TTR15-16 meganucleases described herein for recognizing and cleaving the TTR 15-16 recognition sequence in a CHO cell reporter assay. The activity index represents % GFP positive cells for each cell line expressing the test meganuclease normalized to the cell line expressing the CHO-23/24 meganuclease accounting for the toxicity of the meganuclease.

Engineered meganucleases were designed against the TTR 5-6 binding site and evaluated for indel formation in two cell lines. TTR 5-6L.1204 showed activity in each cell line, giving rise to about 25% indels in HepG2 cells (FIG. 7A) and about 15% indels in HEK293 cells (FIG. 7B). This meganuclease showed stable indels at 2, 6, and 9 days post electroporation in both cell lines, indicating that they were well-tolerated (see FIGS. 7A and 7B).

3. Conclusions

These data indicate that TTR meganucleases give rise to high levels of on-target editing at the TTR 5-6 site in vitro. The nuclease tested show consistent editing throughout the course of the experiment, which indicated it was well-tolerated by the cells and the genomic edits are persistent.

Example 3

Characterization of Meganucleases that Bind and Cleave TTR 15-16 Recognition Sequences 1. Meganucleases that Bind and Cleave the TTR 15-16 Recognition Sequence Recombinant meganucleases that target in the TTR 15-16 recognition site (SEQ ID NOs: 11-14), collectively referred to herein as "TTR 15-16 meganucleases," were engineered to bind and cleave the TTR 15-16 recognition sequence in the human genome (SEQ ID NO: 7). Each recognition sequence is present in the TTR gene, specifically within exon 3. Each TTR 15-16 recombinant meganuclease comprises an N-terminal nuclease-localization signal derived from SV40, a first meganuclease subunit, a linker sequence, and a second meganuclease subunit. A first subunit in each TTR 15-16 meganuclease binds to a first TTR 15-16 recognition half-site (SEQ ID NO: 26), while a second subunit binds to a second TTR 15-16 recognition half-site (SEQ ID NO: 28; see, FIG. 2).

The TTR15-16 binding subunits each comprise a 56 base pair hypervariable region, referred to as HVR1 and HVR2, respectively. The HVR1 region of each TTR 15-16 meganuclease binding subunit consists of residues 24-79 of any one of SEQ ID NOs: 11-14. The HVR2 region of each TTR 15-16 meganuclease consists of residues 215-270 of any one of SEQ ID NOs: 11-14. The TTR 15-16 binding regions of SEQ ID NOs: 11-14 are provided as SEQ ID NOs: 16-23, respectively.

2. Cleavage of TTR 15-16 Recognition Sequences in a CHO Cell Reporter Assay

To determine whether TTR 15-16 meganucleases could bind and cleave the human 15-16 recognition sequence (SEQ ID NO: 7), the recombinant meganucleases TTR 15-16x.81, TTR 15-16L.161, TTR 15-16L.164, and TTR 15-16L.181 were evaluated using the CHO cell reporter assay previously described (see, WO/2012/167192, FIG. 5, and as described in Example 1 above).

In CHO reporter cell lines developed for this study, one recognition sequence inserted into the GFP gene was the human TTR 15-16 recognition sequence (SEQ ID NO: 7). As described for Example 1, the second recognition sequence inserted into the GFP gene was a CHO-23/24 recognition sequence, which is recognized and cleaved by a control meganuclease called "CHO-23/24." CHO reporter cells were transfected with mRNA encoding the TTR 15-16x.81, TTR 15-16L.161, TTR 15-16L.164, and TTR 15-16L.181 meganucleases. CHO reporter cells were also transfected with mRNA encoding the CHO-23/24 meganuclease and the data was obtained and analyzed as described in Example 1.

3. Results

As shown in FIG. 9, the TTR 15-16x.81, TTR 15-16L.161, TTR 15-16L.164, and TTR 15-16L.181 meganucleases cleaved the human TTR 15-16 recognition sequence with high frequency.

3. Conclusions

These studies demonstrated that an engineered meganuclease targeting the TTR 15-16 recognition site (e.g., meganucleases of SEQ ID NOs: 11-14) encompassed by the invention can efficiently target and cleave the respective recognition sequences in cells.

Example 4

Characterization of Insertions and Deletions of Meganucleases that Bind and Cleave TTR 15-16 Recognition Sequences 1. Methods In order to evaluate TTR 15-16 meganucleases, HepG2 and HEK293 cells were electroporated with mRNA encoding each TTR 15-16 meganuclease or GFP and harvested and analyzed for transfection efficiency as described in Example 3. Transfection efficiency exceeded 90% for both cell lines. An additional time point was collected at six- or seven-days post electroporation for gDNA extractions as described in Example 3. A further experiment was conducted to determine indel frequency across different dosages in HepG2, HEK293, and Hep3B cells.

Digital droplet PCR (ddPCR) was utilized to determine indel frequency at the TTR 15-16 binding site using oligos P3, F3, and R3 to generate an amplicon surrounding the binding site, as well as P4, F4, R4 to generate a reference amplicon. The ddPCR assay was carried out as described in Example 2.

```
P3:
                                        (SEQ ID NO: 41)
56-FAM/ATGGGCTCA/ZEN/CAACTGAGGAGGAAT/3IABkFQ

F3:
                                        (SEQ ID NO: 42)
TCCAGACTTTCACACCTTATAG

R3:
                                        (SEQ ID NO: 43)
TCCACTTTGTATATCCCTTCTAC

P4:
                                        (SEQ ID NO: 44)
5HEX/TGCTGGACT/ZEN/GGTATTTGTGTCTGA/3IABkFQ

F4:
                                        (SEQ ID NO: 45)
CCACTCATTCTTGGCAGGAT

R4:
                                        (SEQ ID NO: 46)
CACAGAAACACTCACCGTAGG
```

2. Results

Figure 9A:
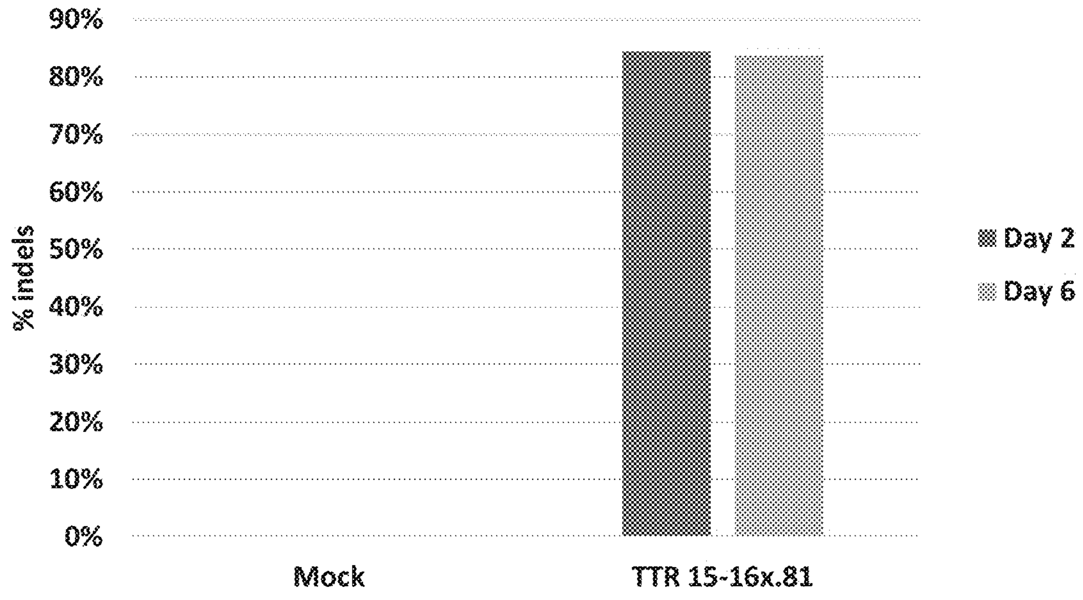
FIGS. 9A-9C. Bar graph showing the percentage frequency of insertions and deletions (indel) of the TTR 15-16x.81 meganuclease targeting the TTR 15-16 recognition sequence in HepG2 cells (FIG. 9A) and HEK 293 cells (FIG. 9B). The meganuclease was tested at two time points (days 2 and 7) following transfection of the meganuclease in FIGS. 9A and 9B. Dose response curves for the TTR 15-16x.81 meganuclease in HepG2, HEK 293, and Hep3B cells is provided in FIG. 9C.
Figure 9B:
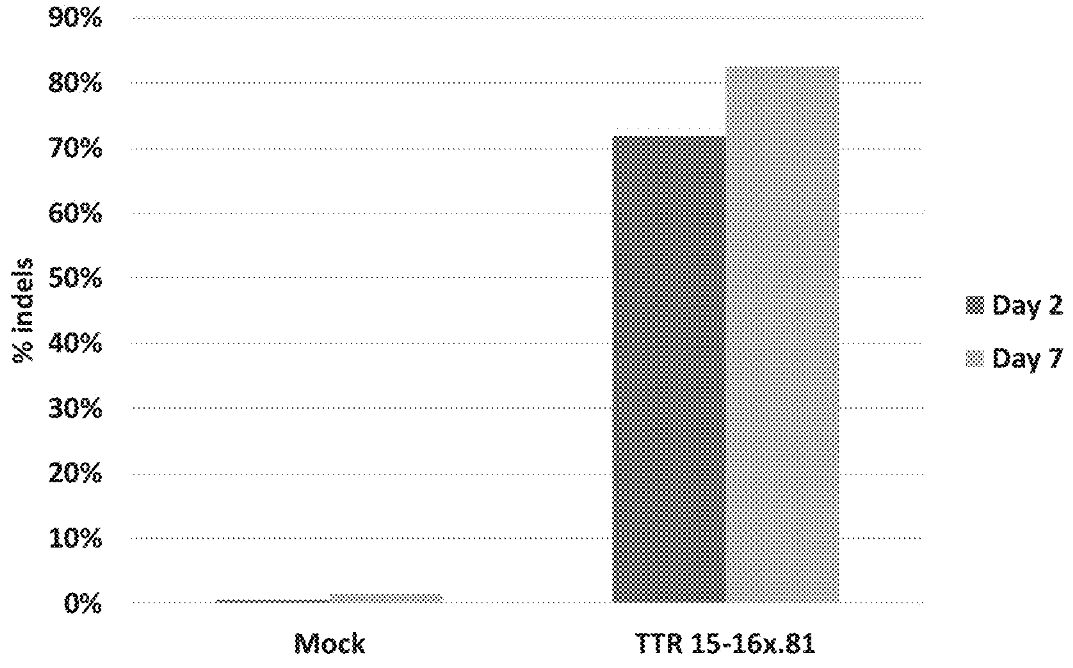
Figure 9C:
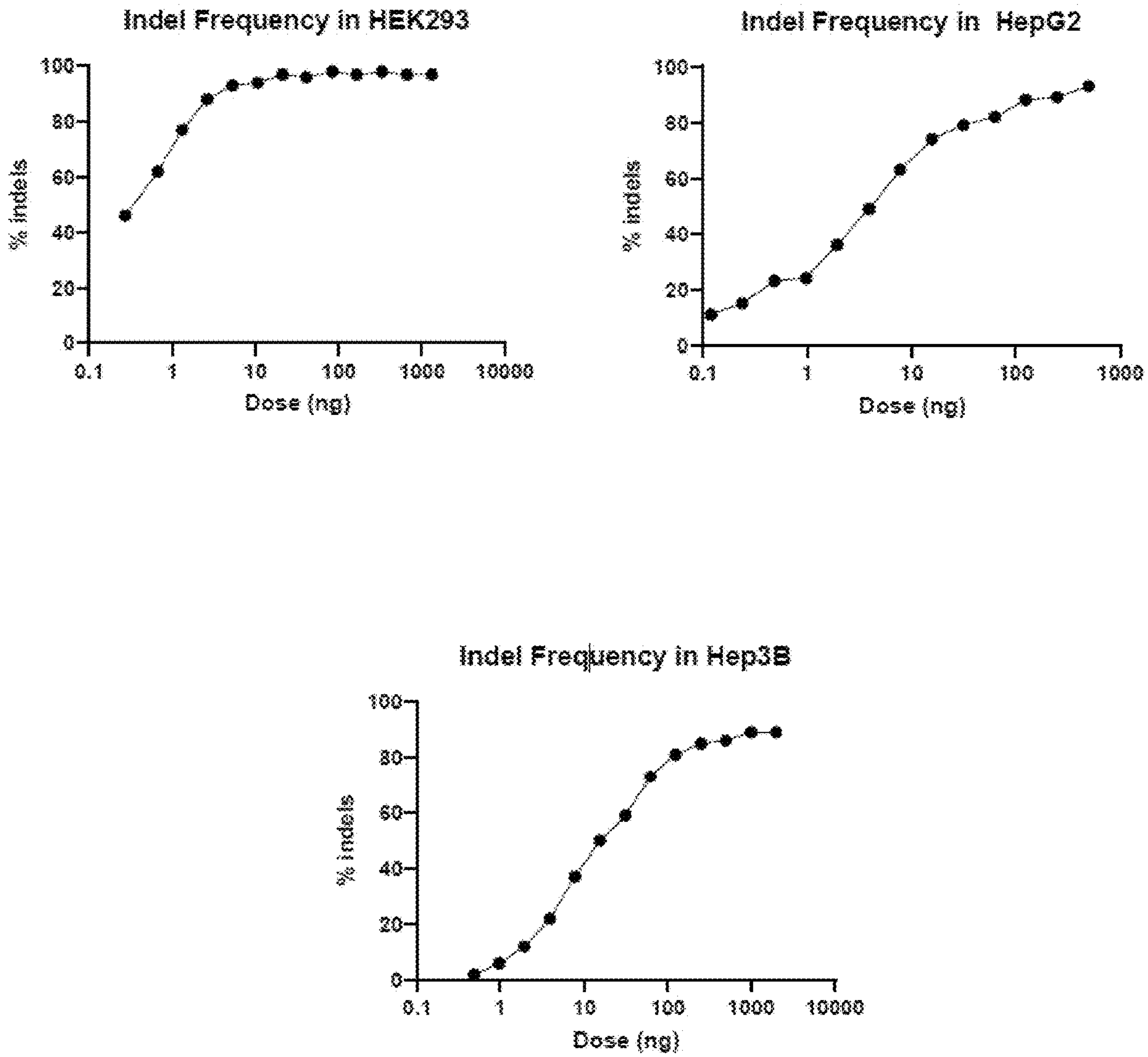

The TTR 15-16x.81 meganuclease showed high levels of activity with indels at about 85% in HEK 293 cells (see FIG. 9A). This nuclease with high potency was further evaluated in HepG2 cells to confirm activity in a liver cell line. Again, TTR 15-16x.81 produced a high frequency of indels at 70-85% (see FIG. 9B). Lastly, the indel frequency demonstrated a dose response with an increasing amount of nuclease providing increased % indel in the three cell lines tested (FIG. 9C).

3. Conclusions

These studies illustrate the ability to utilize an engineered meganuclease for successful editing of the TTR 15-16 binding site. The TTR 15-16x.81 meganuclease tested showed high levels of on-target editing in HEK293 cells and in the HepG2 liver cell line, with 75-85% editing assessed by % indel. TTR 15-16x.81 showed high level of indels at two days post electroporation, and indels were maintained through day 7. A dose response for % indel was demonstrated for the TTR 15-16x.81 nuclease. Together these data demonstrate very high frequencies of on-target indels in both HEK293, HepG2, and Hep3B cell lines after treatment with the TTR 15-16x.81 engineered meganuclease.

Example 5

TTR Editing in Primary Human Hepatocytes

1. Methods

Primary human hepatocytes (PHH) were plated at a density of 3.5e5 cells/well in a 24-well plate. Two hours after plating, cells were transfected in duplicate with Lipofectamine MessengerMax (Thermo Fisher) and varying amounts of TTR 15-16x.81 mRNA (0.5-2 μg). Cells were collected and gDNA isolated as previously described on one and seven days post transfection for indel analysis using ddPCR, with the primers and probes described in Example 4 and the method described in Example 2.

2. Results

Figure 10A:
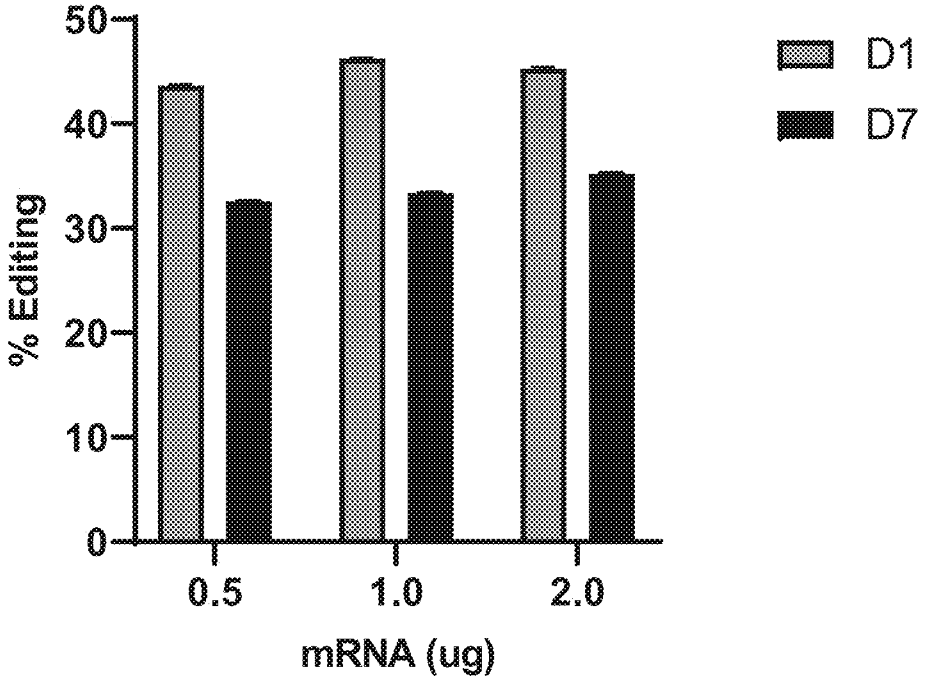
FIGS. 10A and 10B. Graph showing indel frequencies in primary human hepatocytes transfected with indicated amounts of TTR 15-16x.81 mRNA.
Figure 10B:
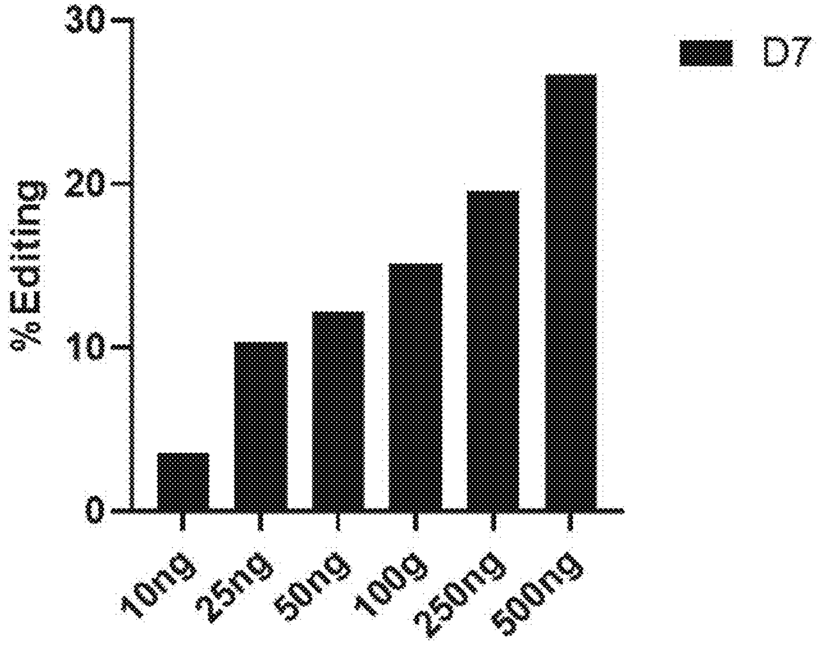

PHH cells were transfected with mRNA encoding TTR 15-16x.81, and indels at the TTR 15-16 targets site were quantified using ddPCR. At all doses tested, we observed about 45% editing at one day post transfection and about 30-35% indels at seven days post transfection (FIG. 10A). A further dose expansion analysis at additional concentrations of nuclease at D7 provided similar results at 0.5 ug of meganuclease; however, the percentage of indels decreased substantially at lower doses down to 0.010 μg of meganuclease (FIG. 10B).

3. Conclusions

These data support the ability of TTR 15-16x.81 nuclease to edit the TTR 15-16 target site in primary human hepatocytes. Interestingly, we find high levels of cutting at one day post transfection, which is reduced by day seven. We hypothesize that the earlier time point represents both insertion and deletions that have occurred at the target site as well as de novo edits that have not been repaired yet. By day seven, it is likely that a fraction of the unresolved edits have been repaired to the wild-type sequence, which likely explains the decrease in editing observed at this timepoint. Further, levels of the meganuclease below 0.5 ug tend to result in a dose dependent decrease in indel activity.

Example 6

Quantitation of Indels in the Liver of FVB Mice with a TTR 5-6 Meganuclease

1. Methods

The TTR 5-6L.1204 meganuclease (SEQ ID NO: 15) was tested in FVB mice with the goal of characterizing targeted indels in mice. A total of 6 mice were injected via tail vein with $5\times10^{11}$ viral genomes of AAV8 expressing the TTR 5-6 meganuclease. The AAV was produced via triple-transfection of HEK293T cells using an AAV8 capsid. Additionally, a control group of three FVB mice received a control injection of PBS. Animals were sacrificed four weeks after AAV administration and livers were collected for genomic DNA isolation.

1.1 gDNA Isolation from Mouse Livers gDNA was isolated from mouse livers using the NucleoSpin Tissue kit from Machery-Nagel (ref #740952.250). The protocol was followed per kit manufacturer product manual. Briefly, a small section of liver was placed in a 1.5 ml tube. Lysis was achieved by incubation of the samples in a solution containing SDS and Proteinase K at 65° C. Appropriate conditions for binding of DNA to the silica membrane of the NucleoSpin® Tissue Columns were created by addition of large amounts of chaotropic ions and ethanol to the lysate. The binding process is reversible and specific to nucleic acids. Contaminations were removed by efficient washing with buffer. Pure genomic DNA was finally eluted under low ionic strength conditions in water.

1.2 INDEL Analysis by ddPCR

Genomic DNA was used for indel quantification using Bio-Rad's QX200 Droplet Digital PCR system. To quantify indels, an amplicon surrounding the TTR 5-6 target site was generated using a forward and reverse primer. A hydrolysis probe was designed to recognize the wild type TTR 5-6 target site. Another probe was designed within the amplicon to serve as a reference. By comparing droplets that are double positive to single positive, indels were calculated for the TTR 5-6 meganuclease. The primer and probe sequences for this assay are shown in Table 4 below:

TABLE 4

| Primers | |
|---|---|
| Forward primer | GTGTCTGTCTGCACATTTC (SEQ ID NO: 47) |
| Reverse primer | AGAAGGCACTTCTTCTTTATCT (SEQ ID NO: 48) |
| Target probe | CCTCGCTGGACTGGTATTTGTGTCT (SEQ ID NO: 49) |
| Reference probe | TCCGATACTCTAATCTCCCTAGGCAAGG (SEQ ID NO: 50) |

Digital PCR reaction was set up using ddPCR Supermix for Probes (no dUTP) (Catalog #1863024 from Bio-Rad), the primers, target probe (in FAM), reference probe (in HEX) and HindIII-HF enzyme (NEB Catalog #R3104S) to fragment the genomic DNA. A total of 5000 genome copies of the mock and treated samples were loaded as template in the PCR reaction.

Figure 11:
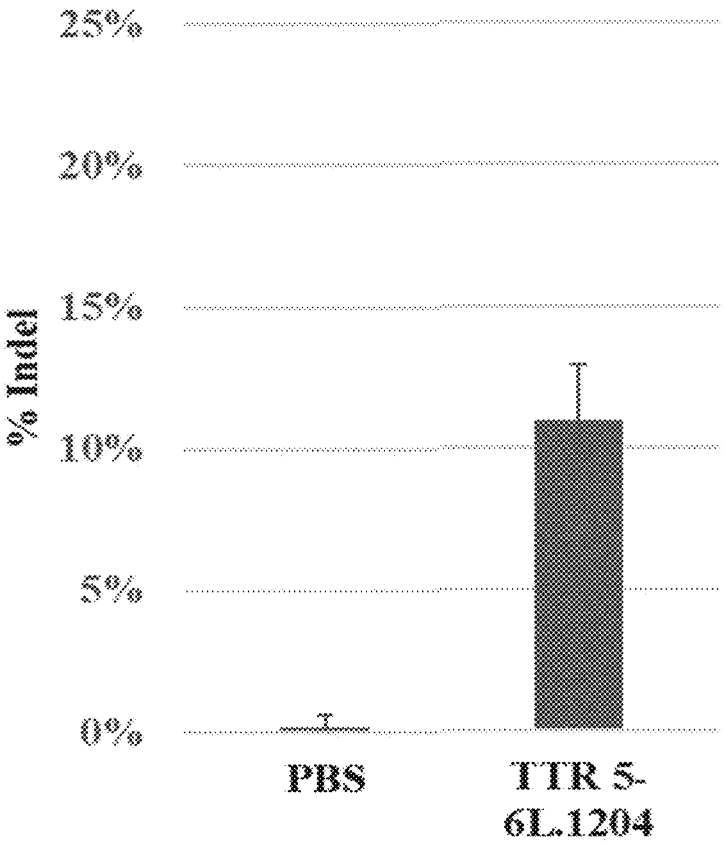
FIG. 11. Graph showing indel frequency in FVB mice administered $5\times10^{11}$ VG AAV8 TTR 5-6L.1204. Mice were euthanized four weeks post AAV dosing, and liver tissue was collected for gDNA isolation and indel analysis by digital droplet PCR (ddPCR).

2. Results gDNA isolated from mouse livers was used as template in a digital droplet PCR drop off assay to quantify on-target indels (FIG. 11). Mice receiving TTR 5-6 meganuclease AAV showed on-target indels. TTR 5-6L.1204 showed editing around 12% indels. No editing was detected in mice that received PBS mock injections.

3. Conclusion

These results indicate that the TTR5-6 meganuclease is active in vivo and was successful in cutting the TTR 5-6 recognition site. Together these data demonstrate the ability of a TTR meganuclease to edit the TTR gene in vivo.

Example 7

In Vivo Generation of Targeted Indels in a Non-Human Primate

1. Methods 1.1 Experimental Design

Next it was tested whether administration of an engineered meganuclease targeting the 5-6 recognition site could target the endogenous TTR gene in non-human primates (NIP). Rhesus monkeys were administered either $6\times10^{12}$ GC/kg or $3\times10^{13}$ GC/kg of an AAV8 vector encoding the TTR 5-6L.1204 meganuclease with a 3' WPRE and driven by a TBG promoter. A liver ultrasound was performed on the animals prior to vector administration and continued to be performed at every 6 months throughout the study. From the day of vector administration through weeks 8-12, all NHPs received prednisolone at a dose of 1 mg/kg/day orally. After 8-12 weeks following vector administration, animals were tapered off prednisolone by gradual reduction of daily dose. Liver biopsies were performed on day 18 and day 128. Necropsy was performed one year after AAV administration.

Using liver tissue collected at necropsy, AAV copy number and on-target indel frequencies were determined.

1.2 In Vivo Indel % On-Target Analysis

Liver tissue was collected for indel analysis at necropsy on day 364. Genomic DNA was isolated using a Geno Grinder (SPEX Sample Prep) to homogenize the tissue and NucleoSpin Blood QuickPure mini kit (Machery-Nagel). The indel % at the target cut site within the 5-6 recognition sequence was determined using drop-off ddPCR as previously described with primers in Table 5 listed below. Indels were calculated using the loss of HEX-positive droplets, normalized to FAM-positive droplets.

TABLE 5

| Primers | |
|---|---|
| Forward primer 5 | AGTCTGGAGAGCTGCAT (SEQ ID NO: 51) |
| Reverse primer 5 | CCAGTAAGATTTGGTGTCTATTTC (SEQ ID NO: 52) |
| Target probe 5 | CCTCAGTTGTGAGCCCATG (FAM; BHQ-1 plus) (SEQ ID NO: 53) |
| Forward primer 6 | CCACTCGTTCTTGGCAGGAT (SEQ ID NO: 54) |
| Reverse primer 6 | CACAGAAACACTCACCGTAGG (SEQ ID NO: 55) |
| Target Probe 6 | 5HEX/TGCTGGACT/ZEN/GGTATTTGTGTC TGA/3IABkFQ (SEQ ID NO: 56) |

1.3 Liver AAV Copy Number Analysis

Liver tissue collected at necropsy on day 364 and cellular DNA was analyzed for AAV copy number using ddPCR as previously described with the primers listed in Table 6 below with an annealing temperature of 58 C.

TABLE 6

| Primers | |
|---|---|
| Forward primer 7 | GGATCCGTGGGAGGTCTAT (SEQ ID NO: 57) |
| Reverse primer 7 | ACCTGCTCCAGCTCTGA (SEQ ID NO: 58) |
| Target probe 7 | 56-FAM/TGCTTCGGA/ZEN/GATCCCTGA ACCC/3IABkFQ (SEQ ID NO: 59) |
| Forward primer 8 | ACCGCCAAGGATGCAC (SEQ ID NO: 60) |
| Reverse primer 8 | GCGGGTGGGAATGGAG (SEQ ID NO: 61) |
| Target Probe 8 | 5HEX/CCAGCAGGC/ZEN/CAGGTACACC/ 3IABkFQ (SEQ ID NO: 62) |

2. Results

Figure 12:
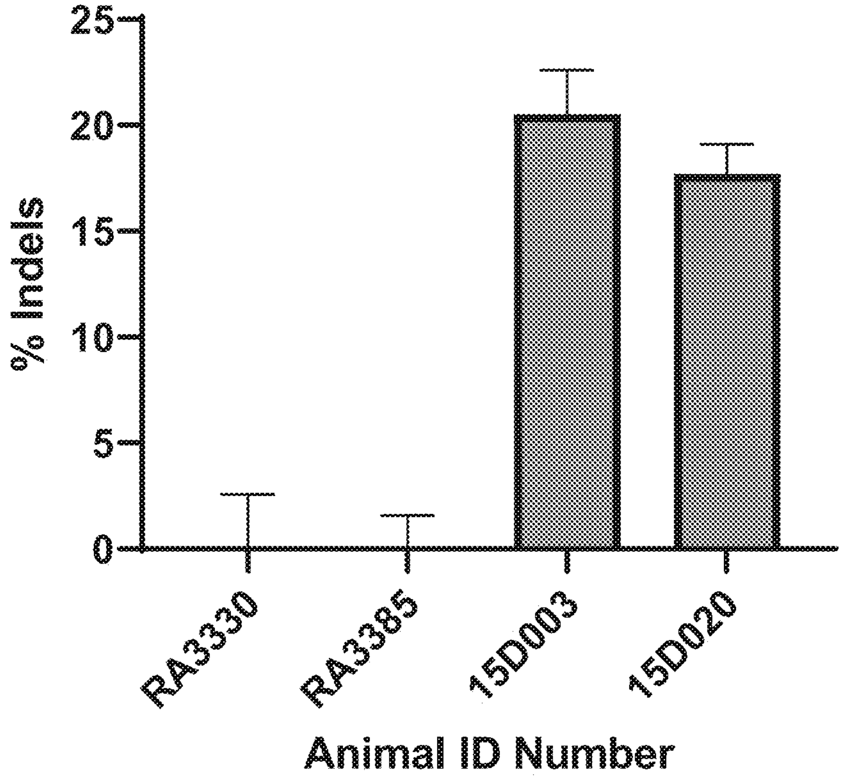
FIG. 12. Bar graph showing the percentage of on-target insertions and deletions in the endogenous non-human primate (NHP) at the 5-6 target site by amplicon sequencing PCR analysis from liver gDNA collected at necropsy (day 364 post AAV dosing). AAVs containing the TTR 5-6L.1204 meganuclease targeting the 5-6 recognition sequence were introduced in Rhesus monkeys at two concentrations ($6\times10^{12}$ (animals RA3330 and RA3385) and $3\times10^{13}$ GC/kg (animals 15D003 and 15D020)).

As shown in FIG. 12, administration of the TTR 5-6L.1204 meganuclease resulted in a dose dependent indel frequency. At necropsy, at $6\times10^{12}$ GC/kg (animals RA3330 and RA3385) no indels were observed. In the animals receiving the higher dose of $3\times10^{13}$ GC/kg (animals 15D003 and 15D020), indels at the on-target TTR 5-6 site were about 15-20% (FIG. 12).

Figure 13:
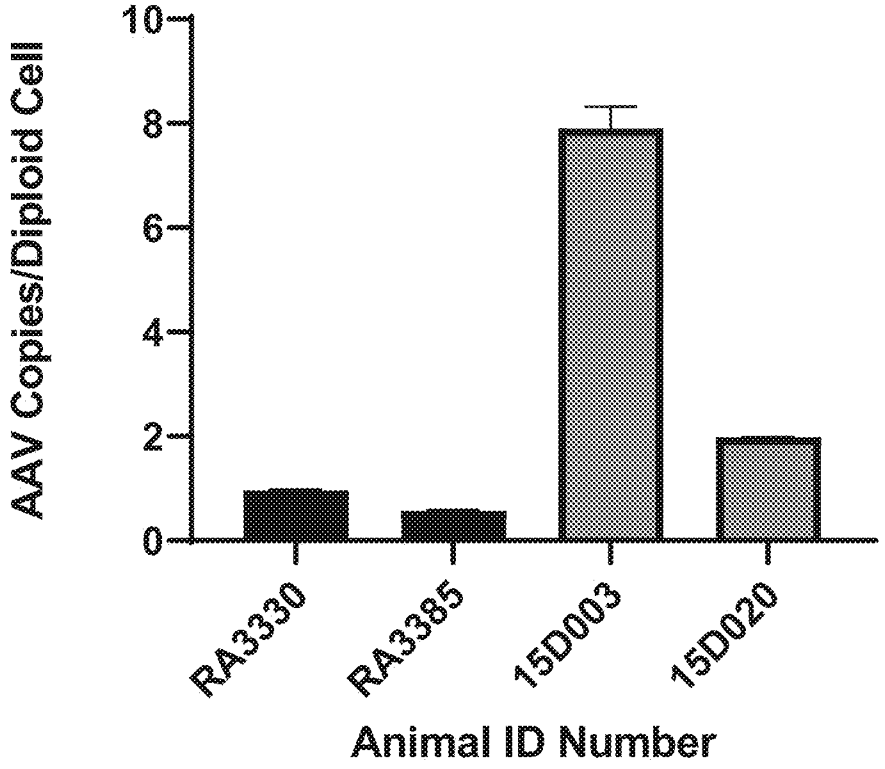
FIG. 13. Bar graph showing the abundance of AAV genomes per diploid cell as measured by ddPCR in liver samples from each animal collected at necropsy (day 364). AAVs containing the TTR 5-6L.1204 meganuclease were introduced in Rhesus monkeys at two concentrations ($6\times10^{12}$ [black bars] and $3\times10^{13}$ GC/kg [gray bars]).

AAV copy number was determined in liver tissues collected at necropsy. FIG. 13 shows that the amount of AAV detected correlates with dose; the $3\times10^{13}$ GC/kg animals were found to have about 2 and 8 AAV genomes/diploid cell and the $6\times10^{12}$ GC/kg animals had about 0.5 and 1 AAV genomes/diploid cell at necropsy on day 364.

3. Conclusions

This study demonstrates that an engineered meganuclease targeting the TTR 5-6 site results in editing of the endogenous TTR gene in NHPs in a dose-dependent manner with indels persisting in the animals treated with the higher dose AAV out to 364 days post vector administration.

Example 8

In Vivo Generation of Targeted Indels at the TTR 15-16 Site in a Non-Human Primate 1. Methods 1.1 Experimental Design Next it was tested whether administration of an engineered meganuclease targeting the 15-16 recognition site could edit the endogenous TTR gene in non-human primates (NHP). Rhesus macaques were administered either $6\times10^{12}$ GC/kg or $3\times10^{13}$ GC/kg of an AAV8 vector encoding the TTR 15-16x.81 meganuclease with a 3' WPRE and driven by a TBG promoter. A liver ultrasound was performed on the animals prior to vector administration and continued to be performed at every 6 months throughout the study. From day of vector administration through weeks 8-12, all NHPs received prednisolone at a dose of 1 mg/kg/day orally. After 8-12 weeks following vector administration, animals were tapered off prednisolone by gradual reduction of daily dose. Liver biopsies were performed on day 18. From each liver biopsy, next generation sequencing and ddPCR were performed to determine in vivo indel %. In addition, AAV vector copy number in d18 and d128 liver biopsies was determined. Throughout the course of the study, blood was collected for measurement of TTR levels in the serum.

1.2 In Vivo Indel % On-Target Analysis

At day 18 and day 128 post-vector administration, a liver biopsy was taken according to the above described experimental protocol. The indel % at the target cut site within the 15-16 recognition sequence was determined by amplicon sequencing analysis using primers F9 and R9 shown in below. Indels were also quantitated using ddPCR and the primers and probes described in Example 6. The loss of FAM-positive copies over the HEX-positive copies was used to calculate TTR 15-16 indels.

F9:
(SEQ ID NO: 63)
GCCATGCCATTTGTTTCCTCCATG

R9:
(SEQ ID NO: 64)
GCATGCTCATGGAATGGG

1.3 AAV Copy Number Analysis

AAV copy number was quantitated in liver tissue collected at the day 18 and day 128 biopsies as previously described in Example 6.

1.4 Serum TTR Analysis

Serum was collected from all animals throughout the course of the study. Serum analysis was completed using a hybrid ligand-binding assay/liquid chromatography-high resolution mass spectrometry (Lanshoeft et al., *Anal. Chem.* 2017, 89, 4, 2628-2635).

2. Results

Figure 14A:
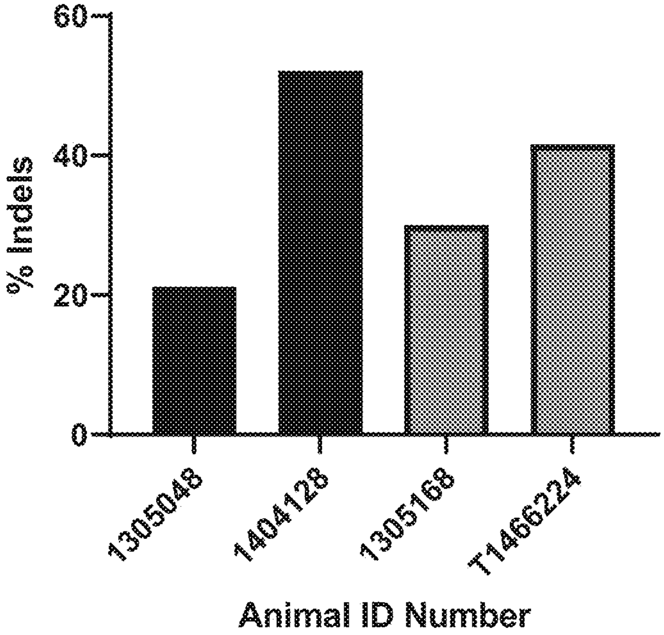
FIGS. 14A-14C. Bar graph showing the percentage of on-target insertions and deletions in the TTR 15-16 recognition sequence by amplicon NGS sequencing (FIG. 14A) and ddPCR (FIG. 14B) from liver biopsies collected at day 18 (d18) post-AAV administration. AAVs containing the TTR 15-16x.81 meganuclease targeting the 15-16 recognition sequence were introduced in Rhesus monkeys at two concentrations ($6\times10^{12}$ [black bars] and $3\times10^{13}$ GC/kg [gray bars]).
Figure 14B:
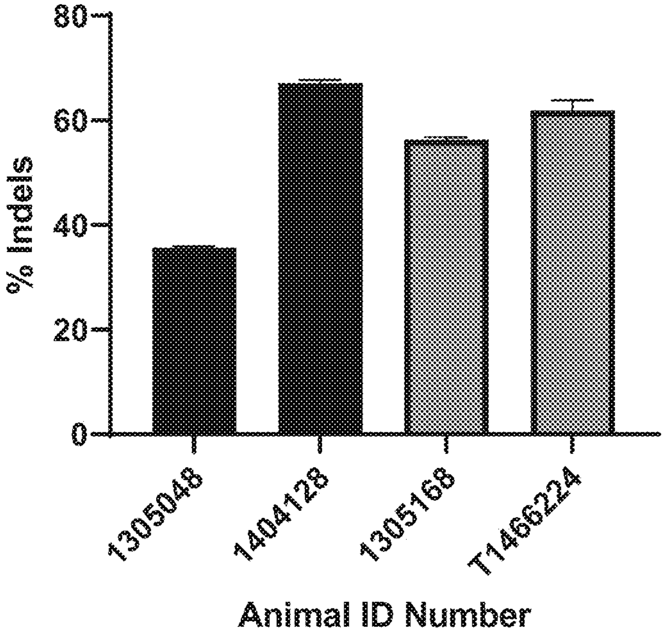
Figure 14C:
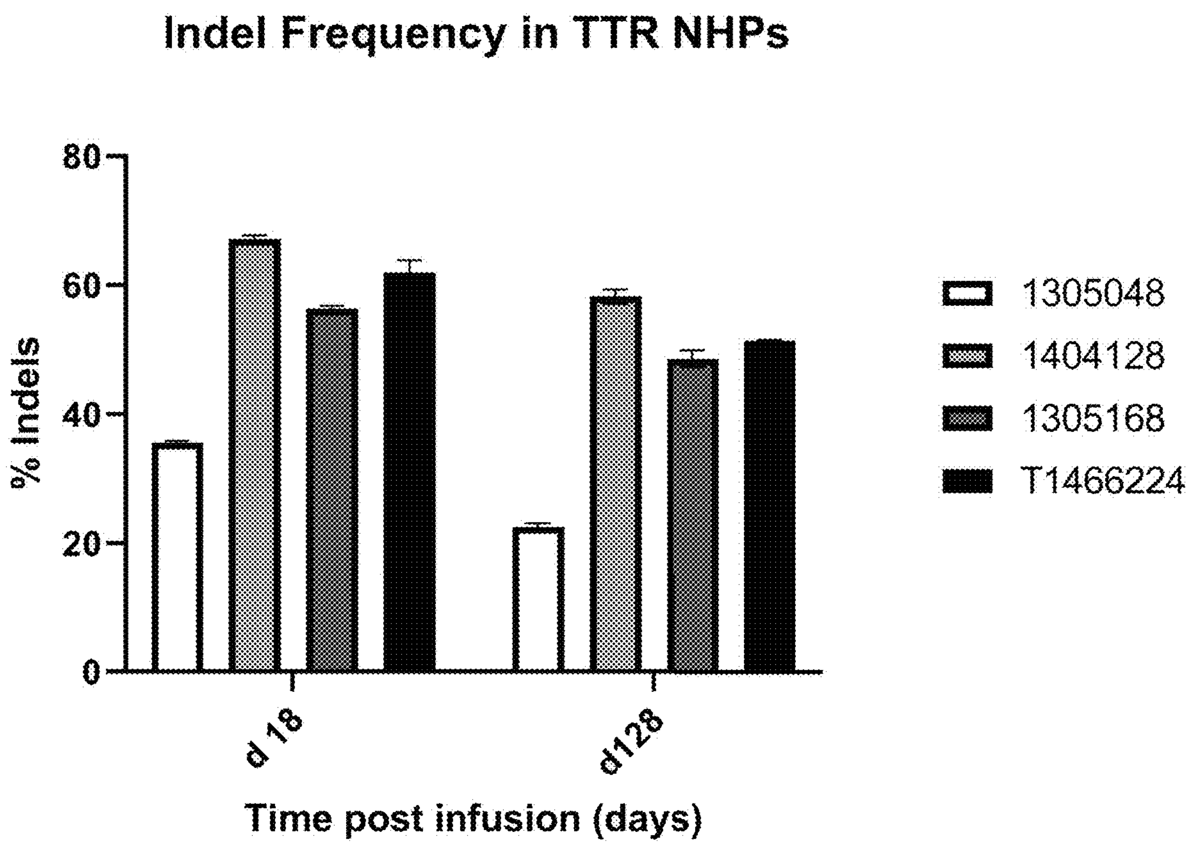

As shown in FIG. 14, administration of an AAV8 carrying the TTR 15-16x.81 meganuclease resulted in high levels of on-target editing in all animals. In the two animals receiving $6\times10^{12}$ GC/kg (black bars), we saw 21% and 52% indels by NGS (FIG. 14A) and 35% and 67% indels by ddPCR (FIG. 14B), respectively. At the $3\times10^{13}$ GC/kg dose (gray bars), we found 30% and 42% indels by NGS (FIG. 14A) and 56% and 62% indels by ddPCR (FIG. 14B), respectively. As further assessed by ddPCR analysis, these indel percentages were maintained out to 128 days with little change (FIG. 14C).

Figure 15:
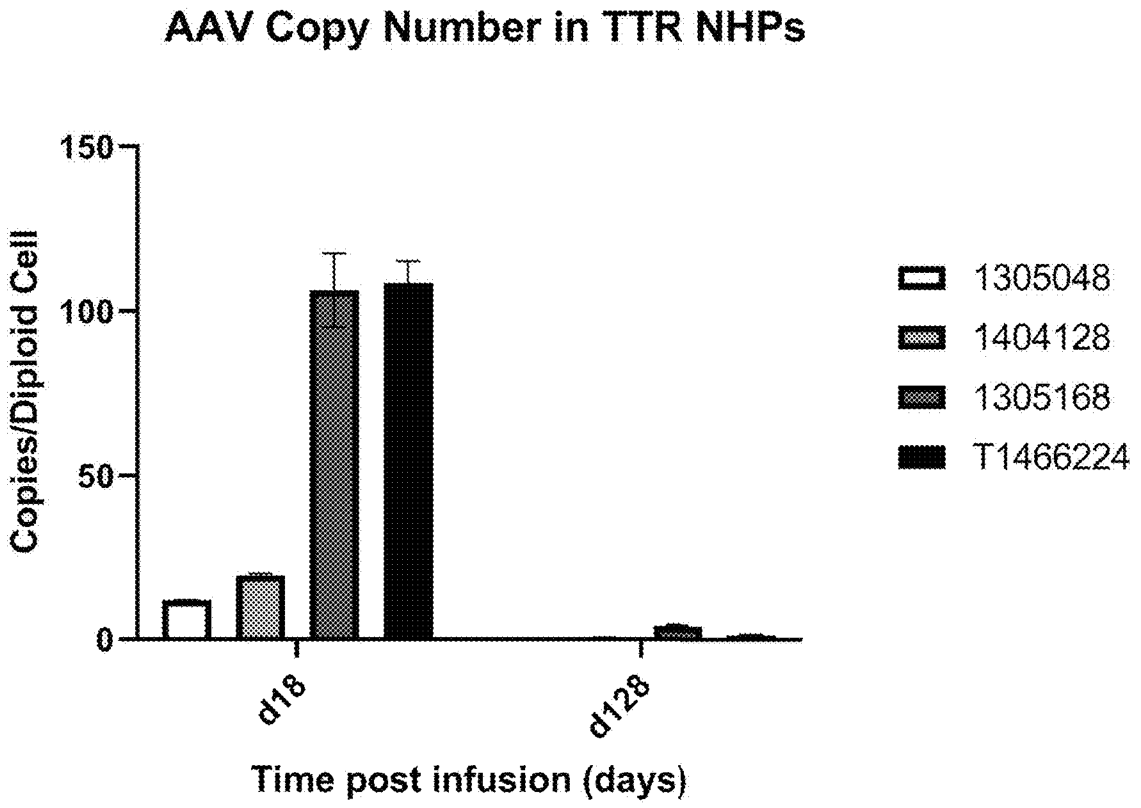
FIG. 15. Bar graph showing the abundance of AAV genomes per diploid cell as measured by ddPCR in liver samples from each animal collected at d18 and d128. AAVs containing the TTR 5-6L.1204 meganuclease were introduced in Rhesus monkeys at two concentrations ($6\times10^{12}$ [animals 1305048 and 1404128] and $3\times10^{13}$ GC/kg [animals 1305168 and T1466224]).

FIG. 15 shows the quantitation of AAV genomes present in the livers at each biopsy. The amount of AAV per diploid cell correlated with the dose of AAV. Animals receiving an AAV8 dose of $6\times10^{12}$ GC/kg had about 12 and 19 AAV copies per diploid cell, while the $3\times10^{12}$ GC/kg dose showed about 106 and 108 AAV copies per diploid cell at d18. The AAV copy number decreased substantially, nearing zero at d128 at both doses.

Figure 16:
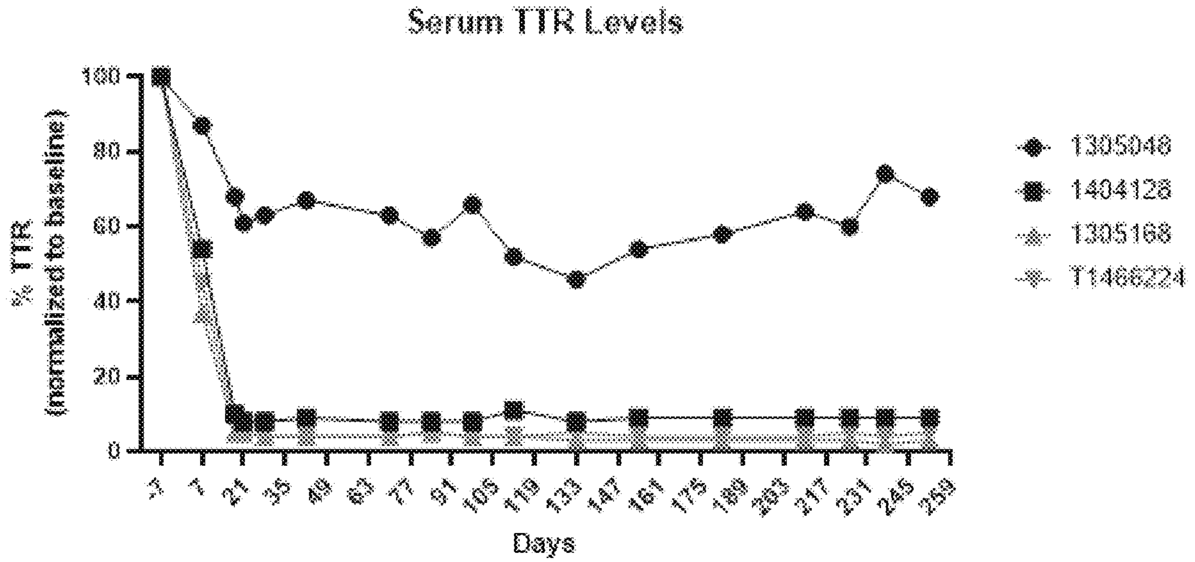
FIG. 16. Line plot showing serum TTR levels in NHPs administered $6\times10^{12}$ GC/kg (black lines) or $3\times10^{13}$ GC/kg (gray lines) of AAV8 containing the TTR 15-16x.81 meganuclease. The x-axis indicates days prior (−7) and post-vector administration (7-259).

When looking at the abundance of TTR protein present in the serum of these animals, we see a large reduction from baseline bleeds taken seven days before vector administration (day −7) (FIG. 16). In three of the four animals, we see >90% reduction in serum TTR protein levels by day 21, which is maintained for >250 days post vector administration. One animal in the $6\times10^{12}$ GC/kg group shows a more modest reduction in serum TTR protein levels, averaging about 40% reduction from baseline.

3. Conclusions

Together these data demonstrate the ability of an engineered meganuclease to successfully edit the TTR 15-16 target site in vivo. Using both ddPCR and NGS, we are able to detect high levels of editing in all animals treated. The ddPCR method results in higher editing rates due to the ability of the assay to detect larger insertions and deletions in the TTR 15-16 target site compared to NGS. Interestingly, we saw variable levels of editing in the two animals treated at the $6\times10^{12}$ GC/kg, which is likely due to reduced transduction in one animal, as supported by the AAV copy number data. In all animals, we see a persistent reduction in circulating serum TTR levels, which correlates with the editing frequencies in the liver. Advantageously, there was observed a substantial near complete reduction in AAV copy number by 128 days post injection at both the low and high dose. This result indicates that the amount of AAV genomes in the cell is decreasing while high levels of indels is maintained in animals treating with the TTR 15-16x.81 meganuclease. In addition, the levels of indels at the TTR 15-16 site observed with the TTR 15-16x.81 meganuclease was significantly greater than the levels observed at the TTR 5-6 site with the TTR 5-6L.1204 engineered meganuclease as demonstrated in example 7. In that example, the TTR 5-6L.1204 meganuclease demonstrated little to no indels at the dose of $6\times10^{12}$ GC/kg compared to up to 67% indels at the TTR 15-16 site with the TTR 15-16x.81 meganuclease. While the TTR 15-16L.1204 meganuclease demonstrated indels at the higher dose of $3\times10^{13}$ GC/kg of about 15%-20%, this was significantly lower than the indels observed at the TTR 15-16 site with the TTR 15-16x.81 meganuclease, which again yielded over 60% indels out to 128 days post injection. These results indicate that engineered meganucleases targeting the TTR 15-16 site in an in vivo NHP animal model lead to unexpectedly higher indels compared to another site (e.g., the TTR 5-6 site) in the TTR gene loci.

Sequence Listing

SEQ ID NO: 1
MNTKYNKEFLLYLAGFVDGDGSIIAQIKPNQSYKFKHQLSLAFQVTQKTQRRWFLDKLVDEIG
VGYVRDRGSVSDYILSEIKPLHNFLTQLQPFLKLKQKQANLVLKIIWRLPSAKESPDKFL
EVCTWVDQIAALNDSKTRKTTSETVRAVLDSLSEKKKSSP

SEQ ID NO: 2
LAGLIDADG

SEQ ID NO: 3
GTTGACTAAGTCAATAATCAGAATCAGCAGGTTTGCAGTCAGATTGGCAGGGAT
AAGCAGCCTAGCTCAGGAGAAGTGAGTATAAAAGCCCCAGGCTGGGAGCAGCCA
TCACAGAAGTCCACTCATTCTTGGCAGGATGGCTTCTCATCGTCTGCTCCTCCTCT
GCCTTGCTGGACTGGTATTTGTGTCTGAGGCTGGCCCTACGGTGAGTGTTTCTGTG
ACATCCCATTCCTACATTTAAGATTCACGCTAAATGAAGTAGAAGTGACTCCTTC
CAGCTTTGCCAACCAGCTTTTATTACTAGGGCAAGGGTACCCAGCATCTATTTTT
AATATAATTAATTCAAACTTCAAAAAGAATGAAGTTCCACTGAGCTTACTGAGCT
GGGACTTGAACTCTGAGCATTCTACCTCATTGCTTTGGTGCATTAGGTTTGTAATA
TCTGGTACCTCTGTTTCCTCAGATAGATGATAGAAATAAAGATATGATATTAAGG
AAGCTGTTAATACTGAATTTTCAGAAAAGTATCCCTCCATAAAATGTATTTGGGG
GACAAACTGCAGGAGATTATATTCTGGCCCTATAGTTATTCAAAACGTATTTATT
GATTAATCTTTAAAAGGCTTAGTGAACAATATTCTAGTCAGATATCTAATTCTTA
AATCCTCTAGAAGAATTAACTAATACTATAAAATGGGTCTGGATGTAGTTCTGAC

-continued

| Sequence Listing |
| --- |

ATTATTTTATAACAACTGGTAAGAGGGAGTGACTATAGCAACAACTAAAATGAT
CTCAGGAAAACCTGTTTGGCCCTATGTATGGTACATTACATCTTTTCAGTAATTCC
ACTCAAATGGAGACTTTTAACAAAGCAACTGTTCTCAGGGGACCTATTTTCTCCC
TTAAAATTCATTATACACATCCCTGGTTGATAGCAGTGTGTCTGGAGGCAGAAAC
CATTCTTGCTTTGGAAACAATTACGTCTGTGTTATACTGAGTAGGGAAGCTCATT
AATTGTCGACACTTACGTTCCTGATAATGGGATCAGTGTGTAATTCTTGTTTCGCT
CCAGATTTCTAATACCACAAAGAATAAATCCTTTCACTCTGATCAATTTTGTTAAC
TTCTCACGTGTCTTCTCTACACCCAGGGCACCGGTGAATCCAAGTGTCCTCTGAT
GGTCAAAGTTCTAGATGCTGTCCGAGGCAGTCCTGCCATCAATGTGGCCGTGCAT
GTGTTCAGAAAGGCTGCTGATGACACCTGGGAGCCATTTGCCTCTGGGTAAGTTG
CCAAAGAACCCTCCCACAGGACTTGGTTTTATCTTCCCGTTTGCCCCTCACTTGGT
AGAGAGAGGCTCACATCATCTGCTAAAGAATTTACAAGTAGATTGAAAAACGTA
GGCAGAGGTCAAGTATGCCCTCTGAAGGATGCCCTCTTTTTGTTTTGCTTAGCTA
GGAAGTGACCAGGAACCTGAGCATCATTTAGGGGCAGACAGTAGAGAAAAGAA
GGAATCAGAACTCCTCTCCTCTAGCTGTGGTTTGCAACCCTTTTGGGTCACAGAA
CACTTTATGTAGGTGATGAAAAGTAAACATTCTATGCCCAGAAAAAATGCACAG
ATACACACACATACAAAATCATATATGTGATTTTAGGAGTTTCACAGATTCCCTG
GTGTCCCTGGGTAACACCAAAGCTAAGTGTCCTTGTCTTAGAATTTTAGGAAAAG
GTATAATGTGTATTAACCCATTAACAAAAGGAAAGGAATTCAGAAATATTATTA
ACCAGGCATCTGTCTGTAGTTAATATGGATCACCCAAAACCCAAGGCTTTTGCCT
AATGAACACTTTGGGGCACCTACTGTGTGCAAGGCTGGGGGCTGTCAAGCTCAGT
TAAAAAAAAAAAGATAGAAGAGATGGATCCATGAGGCAAAGTACAGCCCCAGG
CTAATCCCACGATCACCCGACTTCATGTCCAAGAGTGGCTTCTCACCTTCATTAG
CCAGTTCACAATTTTCATGGAGTTTTTCTACCTGCACTAGCAAAAACTTCAAGGA
AAATACATATTAATAAATCTAAGCAAAGTGACCAGAAGACAGAGCAATCAGGAG
ACCCTTTGCATCCAGCAGAAGAGGAACTGCTAAGTATTTACATCTCCACAGAGAA
GAATTTCTGTTGGGTTTTAATTGAACCCCAAGAACCACATGATTCTTCAACCATT
ATTGGGAAGATCATTTTCTTAGGTCTGGTTTTAACTGGCTTTTTATTTGGGAATTC
ATTTATGTTTATATAAAATGCCAAGCATAACATGAAAAGTGGTTACAGGACTATT
CTAAGGGAGAGACAGAATGGACACCAAAAATATTCCAATGTTCTTGTGAATCTTT
TCCTTGCACCAGGACAAAAAAAAAAAGAAGTGAAAAGAAGAAAGGAGGAGGGG
CATAATCAGAGTCAGTAAAGACAACTGCTATTTTTATCTATCGTAGCTGTTGCAG
TCAAATGGGAAGCAATTTCCAACATTCAACTATGGAGCTGGTACTTACATGGAAA
TAGAAGTTGCCTAGTGTTTGTTGCTGGCAAAGAGTTATCAGAGAGGTTAAATATA
TAAAAGGGAAAAGAGTCAGATACAGGTTCTTCTTCCTACTTTAGGTTTTCCACTG
TGTGTGCAAATGATACTCCCTGGTGGTGTGCAGATGCCTCAAAGCTATCCTCACA
CCACAAGGGAGAGGAGCGAGATCCTGCTGTCCTGGAGAAGTGCAGAGTTAGAAC
AGCTGTGGCCACTTGCATCCAATCATCAATCTTGAATCACAGGGACTCTTTCTTA
AGTAAACATTATACCTGGCCGGGCACGGTGGCTCACGCCTGTAATCCCAGCACTT
TGGGATGCCAAAGTGGGCATATCATCTGAGGTCAGGAGTTCAAGACCAGCCTGG
CCAACATGGCAAAACTCCGTCTTTATGAAAAATACAAAAATTAGCCAGGCATGG
TGGCAGGCGCCTGTAATCCCAGCTAATTGGGAGGCTGAGGCTGGAGAATCCCTT
GAATCTAGGAGGCAGAGGTTGCAGTGAGCTGAGATCGTGCCATTGCACTCCAGC
CTGGGTGACAAGAGTAAAACTCTGTCTCAAAAAAAAAAAATTATACCTACATTCT
CTTCTTATCAGAGAAAAAAATCTACAGTGAGCTTTTCAAAAAGTTTTTACAAACT
TTTTGCCATTTAATTTCAGTTAGGAGTTTTCCCTACTTCTGACTTAGTTGAGGGGA
AATGTTCATAACATGTTTATAACATGTTTATGTGTGTTAGTTGGTGGGGGTGTATT
ACTTTGCCATGCCATTTGTTTCCTCCATGCGTAACTTAATCCAGACTTTCACACCT
TATAGGAAAACCAGTGAGTCTGGAGAGCTGCATGGGCTCACAACTGAGGAGGAA
TTTGTAGAAGGGATATACAAAGTGGAAATAGACACCAAATCTTACTGGAAGGCA
CTTGGCATCTCCCCATTCCATGAGCATGCAGAGGTGAGTATACAGACCTTCGAGG
GTTGTTTTGGTTTTGGTTTTTGCTTTTGGCATTCCAGGAAATGCACAGTTTTACTC
AGTGTACCACAGAAATGTCCTAAGGAAGGTGATGAATGACCAAAGGTTCCCTTT
CCTATTATACAAGAAAAAATTCACAACACTCTGAGAAGCAAATTTCTTTTTGACT
TTGATGAAAATCCACTTAGTAACATGACTTGAACTTACATGAAACTACTCATAGT
CTATTCATTCCACTTTATATGAATATTGATGTATCTGCTGTTGAAATAATAGTTTA
TGAGGCAGCCCTCCAGACCCCACGTAGAGTGTATGTAACAAGAGATGCACCATT
TTATTTCTCGAAAACCCGTAACATTCTTCATTCCAAAACACATCTGGCTTCTCGGA
GGTCTGGACAAGTGATTCTTGGCAACACATACCTATAGAGACAATAAAATCAAA
GTAATAATGGCAACACAATAGATAACATTTACCAAGCATACACCATGTGGCAGA
CACAATTATAAGTGTTTTCCATATTTAACCTACTTAATCCTCAGGAATAAGCCACT
GAGGTCAGTCCTATTATTATCCCCATCTTATAGATGAAGAAAATGAGGCACCAGG
AAGTCAAATAACTTGTCAAAGGTCACAAGACTAGGAAATACACAAGTAGAAATG
TTTACAATTAAGGCCCAGGCTGGGTTTGCCCTCAGTTCTGCTATGCCTCGCATTAT
GCCCCAGGAAACTTTTTCCCTTGTGAAAGCCAAGCTTAAAAAAAGAAAAGCCAC
ATTTGTAACGTGCTCTGTTCCCCTGCCTATGGTGAGGATCTTCAAACAGTTATACA
TGGACCCAGTCCCCCTGCCTTCTCCTTAATTTCTTAAGTCATTTGAAACAGATGGC
TGTCATGGAAATAGAATCCAGACATGTTGGTCAGAGTTAAAGATCAACTAATTCC
ATCAAAAATAGCTCGGCATGAAAGGGAACTATTCTCTGGCTTAGTCATGGATGA
GACTTTCAATTGCTATAAAGTGGTTCCTTTATTAGACAATGTTACCAGGGAAACA
ACAGGGGTTTGTTTGACTTCTGGGGCCCACAAGTCAACAAGAGAGCCCCATCTAC
CAAGGAGCATGTCCCTGACTACCCCTCAGCCAGCAGCAAGACATGGACCCCAGT
CAGGGCAGGAGCAGGGTTTCGGCGGCGCCCAGCACAAGACATTGCCCCTAGAGT
CTCAGCCCCTACCCTCGAGTAATAGATCTGCCTACCTGAGACTGTTGTTTGCCCA
AGAGCTGGGTCTCAGCCTGATGGGAACCATATAAAAAGGTTCACTGACATACTG
CCCACATGTTGTTCTCTTTCATTAGATCTTAGCTTCCTTGTCTGCTCTTCATTCTTG
CAGTATTCATTCAACAAACATTAAAAAAAAAAAAAAAGCATTCTATGTGTGGAAC

-continued

Sequence Listing

ACTCTGCTAGATGCTGTGGATTTAGAAATGAAAATACATCCCGACCCTTGGAATG
GAAGGGAAAGGACTGAAGTAAGACAGATTAAGCAGGACCGTCAGCCCAGCTTG
AAGCCCAGATAAATACGGAGAACAAGAGAGAGCGAGTAGTGAGAGATGAGTCC
CAATGCCTCACTTTGGTGACGGGTGCGTGGTGGGCTTCATGCAGCTTCTTCTGAT
AAATGCCTCCTTCAGAACTGGTCAACTCTACCTTGGCCAGTGACCCAGGTGGTCA
TAGTAGATTTACCAAGGGAAAATGGAAACTTTTATTAGGAGCTCTTAGGCCTCTT
CACTTCATGGATTTTTTTTTCCTTTTTTTTTGAGATGGAGTTTTGCCCTGTCACCCA
GGCTGGAATGCAGTGGTGCAATCTCAGCTCACTGCAACCTCCGCCTCCCAGGTTC
AAGCAATTCTCCTGCCTCAGCCTCCCGAGTAGCTGGGACTACAGGTGTGCGCCAC
CACACCAGGCTAATTTTTGTATTTTTTGTAAAGACAGGTTTTCACCACGTTGGCCA
GGCTGGTCTGAACTCCAGACCTCAGGTGATTCACCTGTCTCAGCCTCCCAAAGTG
CTGGGATTACAGGTGTGAGCCACCGTGCCCGGCTACTTCATGGATTTTTGATTAC
AGATTATGCCTCTTACAATTTTTAAGAAGAATCAAGTGGGCTGAAGGTCAATGTC
ACCATAAGACAAAAGACATTTTTATTAGTTGATTCTAGGGAATTGGCCTTAAGGG
GAGCCCTTTCTTCCTAAGAGATTCTTAGGTGATTCTCACTTCCTCTTGCCCCAGTA
TTATTTTTGTTTTTGGTATGGCTCACTCAGATCCTTTTTTCCTCCTATCCCTAAGTA
ATCCGGGTTTCTTTTTCCCATATTTAGAACAAAATGTATTTATGCAGAGTGTGTCC
AAACCTCAACCCAAGGCCTGTATACAAAATAAATCAAATTAAACACATCTTTACT
GTCTTCTACCTCTTTCCTGACCTCAATATATCCCAACTTGCCTCACTCTGAGAACC
AAGGCTGTCCCAGCACCTGAGTCGCAGATATTCTACTGATTTGACAGAACTGTGT
GACTATCTGGAACAGCATTTTGATCCACAATTTGCCCAGTTACAAAGCTTAAATG
AGCTCTAGTGCATGCATATATATTTCAAAATTCCACCATGATCTTCCACACTCTGT
ATTGTAAATAGAGCCCTGTAATGCTTTTACTTCGTATTTCATTGCTTGTTATACAT
AAAAATATACTTTTCTTCTTCATGTTAGAAAATGCAAAGAATAGGAGGGTGGGG
GAATCTCTGGGCTTGGAGACAGGAGACTTGCCTTCCTACTATGGTTCCATCAGAA
TGTAGACTGGGACAATACAATAATTCAAGTCTGGTTTGCTCATCTGTAAATTGGG
AAGAATGTTTCCAGCTCCAGAATGCTAAATCTCTAAGTCTGTGGTTGGCAGCCAC
TATTGCAGCAGCTCTTCAATGACTCAATGCAGTTTTGCATTCTCCCTACCTTTTTT
TTCTAAAACCAATAAAATAGATACAGCCTTTAGGCTTTCTGGGATTTCCCTTAGT
CAAGCTAGGGTCATCCTGACTTTCGGCGTGAATTTGCAAAACAAGACCTGACTCT
GTACTCCTGCTCTAAGGACTGTGCATGGTTCCAAAGGCTTAGCTTGCCAGCATAT
TTGAGCTTTTTCCTTCTGTTCAAACTGTTCCAAAATATAAAAGAATAAAATTAATT
AAGTTGGCACTGGACTTCCGGTGGTCAGTCATGTGTGTCATCTGTCACGTTTTTCG
GGCTCTGGTGGAAATGGATCTGTCTGTCTTCTCTCATAGGTGGTATTCACAGCCA
ACGACTCCGGCCCCCGCCGCTACACCATTGCCGCCCTGCTGAGCCCCTACTCCTA
TTCCACCACGGCTGTCGTCACCAATCCCAAGGAATGAGGGACTTCTCCTCCAGTG
GACCTGAAGGACGAGGGATGGGATTTCATGTAACCAAGAGTATTCCATTTTTACT
AAAGCAGTGTTTTCACCTCATATGCTATGTTAGAAGTCCAGGCAGAGACAATAAA
ACATTCCTGTGAAAGGCACTTTTCATTCCACTTTAACTTGATTTTTTAAATTCCCT
TATTGTCCCTTCCAAAAAAAAGAGAATCAAAATTTTACAAAGAATCAAAGGAAT
TCTAGAAAGTATCTGGGCAGAACGCTAGGAGAGATCCAAATTTCCATTGTCTTGC
AAGCAAAGCACGTATTAAATATGATCTGCAGCCATTAAAAAGACACATTCTGTA
AA

SEQ ID NO: 4
MASHRLLLLCLAGLVFVSEAGPTGTGESKCPLMVKVLDAVRGSPAINVAVHVFRKA
ADDTWEPFASGKTSESGELHGLTTEEEFVEGIYKVEIDTKSYWKALGISPFHEHAEVV
FTANDSGPRRYTIAALLSPYSYSTTAVVTNPKE

SEQ ID NO: 5
GPTGTGESKCPLMVKVLDAVRGSPAINVAVHVFRKAADDTWEPFASGKTSESGELH
GLTTEEEFVEGIYKVEIDTKSYWKALGISPFHEHAEVVFTANDSGPRRYTIAALLSPYS
YSTTAVVTNPKE

SEQ ID NO: 6
GPTGTGESKCPLMVKVLDAVRGSPAINVAMHVFRKAADDTWEPFASGKTSESGELH
GLTTEEEFVEGIYKVEIDTKSYWKALGISPFHEHAEVVFTANDSGPRRYTIAALLSPYS
YSTTAVVTNPKE

SEQ ID NO: 7
TGCATGGGCTCACAACTGAGGA

SEQ ID NO: 8
ACGTACCCGAGTGTTGACTCCT

SEQ ID NO: 9
GCTGGACTGGTATTTGTGTCTG

SEQ ID NO: 10
CGACCTGACCATAAACACAGAC

SEQ ID NO: 11
MNTKYNKEFLLYLAGFVDADGSIYACITPRQTHKFKHVLALGFSVIQRTRRRWFLDK
LVDEIGVGYVRDRDTTSEYRLSQIKPLHNFLTQLQPFLKLKQKQANLVLKIIEQLPSA
KESPDKFLEVCTWVDQIAALNDSRTRKTTSETVRAVLDSLPGSVGGLSPSQASSAASS

-continued

| Sequence Listing |
|---|

ASSSPGSGISEALRAGAGSGTGYNKEFLLYLAGFVDGDGSIYASIDPDQRSKFKHGLR
LNFQVSQKTQRRWFLDKLVDEIGVGYVQDKGSVSHYILSQIKPLHNFLTQLQPFLKL
KQKQANLVLKIIEQLPSAKESPDKFLEVCTWVDQIAALNDSKTRKTTSETVRAVLDS
LSEKKKSSP

SEQ ID NO: 12
MNTKYNKEFLLYLAGFVDADGSIYACITPRQDYKFKHNLALGFSVIQRTRRRWFLDK
LVDEIGVGYVRDRDTTSEYRLSQIKPLHNFLTQLQPFLKLKQKQANLVLKIIEQLPSA
KESPDKFLEVCTWVDQIAALNDSRTRKTTSETVRAVLDSLPGSVGGLSPSQASSAASS
ASSSPGSGISEALRAGAGSGTGYNKEFLLYLAGFVDGDGSIYASIDPDQRSKFKHGLR
LNFQVSQKTQRRWFLDKLVDEIGVGYVQDKGSVSHYILSEIKPLHNFLTQLQPFLKL
KQKQANLVLKIIEQLPSAKESPDKFLEVCTWVDQIAALNDSKTRKTTSETVRAVLDS
LSEKKKSSP

SEQ ID NO: 13
MNTKYNKEFLLYLAGFVDADGSIYACITPRQLCKFKHGLALGFSVIQRTRRRWFLDK
LVDEIGVGYVRDRDTTSEYRLSQIKPLHNFLTQLQPFLKLKQKQANLVLKIIEQLPSA
KESPDKFLEVCTWVDQIAALNDSRTRKTTSETVRAVLDSLPGSVGGLSPSQASSAASS
ASSSPGSGISEALRAGAGSGTGYNKEFLLYLAGFVDGDGSIYASIDPDQRSKFKHGLR
LNFQVSQKTQRRWFLDKLVDEIGVGYVQDKGSVSHYILSEIKPLHNFLTQLQPFLKL
KQKQANLVLKIIEQLPSAKESPDKFLEVCTWVDQIAALNDSKTRKTTSETVRAVLDS
LSEKKKSSP

SEQ ID NO: 14
MNTKYNKEFLLYLAGFVDADGSIYACITPRQTHKFKHNLALGFSVIQRTRRRWFLDK
LVDEIGVGYVRDRDTTSEYRLSQIKPLHNFLTQLQPFLKLKQKQANLVLKIIEQLPSA
KESPDKFLEVCTWVDQIAALNDSRTRKTTSETVRAVLDSLPGSVGGLSPSQASSAASS
ASSSPGSGISEALRAGAGSGTGYNKEFLLYLAGFVDGDGSIYASIDPDQRSKFKHGLR
LNFQVSQKTQRRWFLDKLVDEIGVGYVQDKGSVSHYILSEIKPLHNFLTQLQPFLKL
KQKQANLVLKIIEQLPSAKESPDKFLEVCTWVDQIAALNDSKTRKTTSETVRAVLDS
LSEKKKSSP

SEQ ID NO: 15
MNTKYNKEFLLYLAGFVDGDGSIFASIEPAQRAKFKHYLRL VFNVTQKTQRRWFLD
KLVDEIGVGYVSDSGSVSLYKLSEIKPLHNFLTQLQPFLKLKQKQANLVLKIIEQLPSA
KESPDKFLEVCTWVDQIAALNDSKTRKTTSETVRAVLDSLPGSVGGLSPSQASSAAS
SASSSPGSGISEALRAGAGSGTGYNKEFLLYLAGFVDSDGSIFASIVPDQSRKFKHALR
LRFIVSQNTRRRWFLDKLVDEIGVGYVKDSGRSAHYTLSEIKPLHNFLTQLQPFLKLK
QKQANLVLKIIEQLPSAKESPDKFLEVCTWVDQIAALNDSKTRKTTSETVRAVLDSLS
EKKKSSP

SEQ ID NO: 16
KEFLLYLAGFVDADGSIYACITPRQTHKFKHVLALGFSVIQRTRRRWFLDKL VDEIGV
GYVRDRDTTSEYRLSQIKPLHNFLTQLQPFLKLKQKQANLVLKIIEQLPSAKESPDKF
LEVCTWVDQIAALNDSRTRKTTSETVRAVLD

SEQ ID NO: 17
KEFLLYLAGFVDADGSIYACITPRQDYKFKHNLALGFSVIQRTRRRWFLDKLVDEIG
VGYVRDRDTTSEYRLSQIKPLHNFLTQLQPFLKLKQKQANL VLKIIEQLPSAKESPDK
FLEVCTWVDQIAALNDSRTRKTTSETVRAVLD

SEQ ID NO: 18
KEFLLYLAGFVDADGSIYACITPRQLCKFKHGLALGFSVIQRTRRRWFLDKLVDEIGV
GYVRDRDTTSEYRLSQIKPLHNFLTQLQPFLKLKQKQANLVLKIIEQLPSAKESPDKF
LEVCTWVDQIAALNDSRTRKTTSETVRAVLD

SEQ ID NO: 19
KEFLLYLAGFVDADGSIYACITPRQTHKFKHNLALGFSVIQRTRRRWFLDKL VDEIGV
GYVRDRDTTSEYRLSQIKPLHNFLTQLQPFLKLKQKQANLVLKIIEQLPSAKESPDKF
LEVCTWVDQIAALNDSRTRKTTSETVRAVLD

SEQ ID NO: 20
KEFLLYLAGFVDGDGSIYASIDPDQRSKFKHGLRLNFQVSQKTQRRWFLDKLVDEIG
VGYVQDKGSVSHYILSQIKPLHNFLTQLQPFLKLKQKQANLVLKIIEQLPSAKESPDK
FLEVCTWVDQIAALNDSKTRKTTSETVRAVLD

SEQ ID NO: 21
KEFLLYLAGFVDGDGSIYASIDPDQRSKFKHGLRLNFQVSQKTQRRWFLDKLVDEIG
VGYVQDKGSVSHYILSEIKPLHNFLTQLQPFLKLKQKQANLVLKIIEQLPSAKESPDKF
LEVCTWVDQIAALNDSKTRKTTSETVRAVLD

SEQ ID NO: 22
KEFLLYLAGFVDGDGSIYASIDPDQRSKFKHGLRLNFQVSQKTQRRWFLDKLVDEIG
VGYVQDKGSVSHYILSEIKPLHNFLTQLQPFLKLKQKQANLVLKIIEQLPSAKESPDKF
LEVCTWVDQIAALNDSKTRKTTSETVRAVLD

-continued

| Sequence Listing |
|---|

SEQ ID NO: 23
KEFLLYLAGFVDGDGSIYASIDPDQRSKFKHGLRLNFQVSQKTQRRWFLDKLVDEIG
VGYVQDKGSVSHYILSEIKPLHNFLTQLQPFLKLKQKQANLVLKIIEQLPSAKESPDKF
LEVCTWVDQIAALNDSKTRKTTSETVRAVLD

SEQ ID NO: 24
KEFLLYLAGFVDGDGSIFASIEPAQRAKFKHYLRLVFNVTQKTQRRWFLDKLVDEIG
VGYVSDSGSVSLYKLSEIKPLHNFLTQLQPFLKLKQKQANL VLKIIEQLPSAKESPDKF
LEVCTWVDQIAALNDSKTRKTTSETVRAVLD

SEQ ID NO: 25
KEFLLYLAGFVDSDGSIFASIVPDQSRKFKHALRLRFIVSQNTRRRWFLDKL VDEIGV
GYVKDSGRSAHYTLSEIKPLHNFLTQLQPFLKLKQKQANLVLKIIEQLPSAKESPDKF
LEVCTWVDQIAALNDSKTRKTTSETVRAVLD

SEQ ID NO: 26
TGCATGGGC

SEQ ID NO: 27
ACGTACCCG

SEQ ID NO: 28
AACTGAGGA

SEQ ID NO: 29
TTGACTCCT

SEQ ID NO: 30
GCTGGACTG

SEQ ID NO: 31
CGACCTGAC

SEQ ID NO: 32
TTGTGTCTG

SEQ ID NO: 33
AACACAGAC

SEQ ID NO: 34
CACTGGACTGGTATTTGTGTCTGA

SEQ ID NO: 35
56-FAM/TGCTGGACT/ZEN/GGTATTTGTGTCTGA/3IABkFQ

SEQ ID NO: 36
CCACTCATTCTTGGCAGGAT

SEQ ID NO: 37
CACAGAAACACTCACCGTAGG

SEQ ID NO: 38
AAATTCCTCCTCAGTTGTGAGCCC

SEQ ID NO: 39
AGTCTGGAGAGCTGCAT

SEQ ID NO: 40
CCAGTAAGATTTGGTGTCTATTTC

SEQ ID NO: 41
ATGGGCTCACAACTGAGGAGGAAT

SEQ ID NO: 42
TCCAGACTTTCACACCTTATAG

SEQ ID NO: 43
TCCACTTTGTATATCCCTTCTAC

SEQ ID NO: 44
TGCTGGACTGGTATTTGTGTCTGA

SEQ ID NO: 45
CCACTCATTCTTGGCAGGAT

-continued

| Sequence Listing |
|---|

SEQ ID NO: 46
CACAGAAACACTCACCGTAGG

SEQ ID NO: 47
GTGTCTGTCTGCACATTTC

SEQ ID NO: 48
AGAAGGCACTTCTTCTTTATCT

SEQ ID NO: 49
CCTCGCTGGACTGGTATTTGTGTCT

SEQ ID NO: 50
TCCGATACTCTAATCTCCCTAGGCAAGG

SEQ ID NO: 51
AGTCTGGAGAGCTGCAT

SEQ ID NO: 52
CCAGTAAGATTTGGTGTCTATTTC

SEQ ID NO: 53
CCTCAGTTGTGAGCCCATG

SEQ ID NO: 54
CCACTCGTTCTTGGCAGGAT

SEQ ID NO: 55
CACAGAAACACTCACCGTAGG

SEQ ID NO: 56
TGCTGGACTGGTATTTGTGTCTGA

SEQ ID NO: 57
GGATCCGTGGGAGGTCTAT

SEQ ID NO: 58
ACCTGCTCCAGCTCTGA

SEQ ID NO: 59
TGCTTCGGAGATCCCTGAACCC

SEQ ID NO: 60
ACCGCCAAGGATGCAC

SEQ ID NO: 61
GCGGGTGGGAATGGAG

SEQ ID NO: 62
CCAGCAGGCCAGGTACACC

SEQ ID NO: 63
GCCATGCCATTTGTTTCCTCCATG

SEQ ID NO: 64
GCATGCTCATGGAATGGG

SEQ ID NO: 65
SLPGSVGGLSPSQASSAASSASSSPGSGISEALRAGAGSGTG

SEQ ID NO: 66
ATGAATACAAAATATAATAAAGAGTTCTTACTCTACTTAGCAGGGTTTGTAGACG
CTGACGGTTCCATCTATGCCTGTATCACGCCTCGTCAAACTCATAAGTTCAAGCA
CGTTCTGGCGCTCGGGTTCTCAGTCATTCAGCGTACACGTCGCCGTTGGTTCCTCG
ACAAGCTGGTGGACGAGATCGGTGTGGGTTACGTGCGTGACAGGGATACGACCA
GCGAATACAGACTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAGGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTATGCCAGTATCGATC
CTGATCAACGGAGTAAGTTCAAGCACGGGCTGAGGCTCAATTTCCAGGTCTCTCA
GAAGACACAGCGCCGTTGGTTCCTCGACAAGCTGGTGGACGAGATCGGTGTGGG
TTACGTGCAGGACAAGGGCAGCGTCTCCCATTACATTCTGTCCCAGATCAAGCCT

-continued

| Sequence Listing |
|---|

CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACNNGTTCCTGGAGGTGTGCACCTGGGTGGACCAGATCGCCGCTCTGAACGACTC
CAAGACCCGCAAGACCACTTCCGAAACCGTCCGCGCCGTTCTAGACANTNTCTCC
GAGAAGAAGAAGTCGTCCCCCTAA

SEQ ID NO: 67
ATGAATACAAAATATAATAAAGAGTTCTTACTCTACTTAGCAGGGTTTGTAGACG
CTGACGGTTCCATCTATGCCTGTATCACGCCTCGTCAAGATTATAAGTTCAAGCA
CAATCTGGCGCTCGGGTTCAGTGTCATTCAGCGTACACGTCGCCGTTGGTTCCTT
GACAAGCTGGTGGACGAGATCGGTGTGGGTTACGTGCGTGACAGGGATACGACC
AGCGAATACAGACTGTCCCAGATCAAGCCTTTGCATAATTTTTTAACACAACTAC
AACCTTTTCTAAAACTAAAACAAAAACAAGCAAATTTAGTTTTAAAAATTATTGA
ACAACTTCCGTCAGCAAAAGAATCCCCGGACAAATTCTTAGAAGTTTGTACATGG
GTGGATCAAATTGCAGCTCTGAATGATTCGAGGACGCGTAAAACAACTTCTGAA
ACCGTTCGTGCTGTGCTAGACAGTTTACCAGGATCCGTGGGAGGTCTATCGCCAT
CTCAGGCATCCAGCGCCGCATCCTCGGCTTCCTCAAGCCCGGGTTCAGGGATCTC
CGAAGCACTCAGAGCTGGAGCAGGTTCCGGCACTGGATACAACAAGGAATTCCT
GCTCTACCTGGCGGGCTTCGTCGACGGGGACGGCTCCATCTATGCCAGTATCGAT
CCTGATCAACGGAGTAAGTTCAAGCACGGGCTGAGGCTCAATTTCCAGGTCTCTC
AGAAGACACAGCGCCGTTGGTTCCTCGACAAGCTGGTGGACGAGATCGGTGTGG
GTTACGTGCAGGACAAGGGCAGCGTCTCCCATTACATTCTGTCCGAGATCAAGCC
TCTGCACAACTTCCTGACCCAGCTCCAGCCCTTCCTGAAGCTCAAGCAGAAGCAG
GCCAACCTCGTGCTGAAGATCATCGAGCAGCTGCCCTCCGCCAAGGAATCCCCG
GACAAGTTCCTGGAGGTGTGCACCTGGGTGGACCAGATCGCCGCTCTGAACGAC
TCCAAGACCCGCAAGACCACTTCCGAAACCGTCCGCGCCGTTCTAGACAGTCTCT
CCGAGAAGAAGAAGTCGTCCCCCTAA

SEQ ID NO: 68
ATGAATACAAAATATAATAAAGAGTTCTTACTCTACTTAGCAGGGTTTGTAGACG
CTGACGGTTCCATCTATGCCTGTATCACGCCTCGTCAACTTTGTAAGTTCAAGCAC
GGGCTGGCGCTCGGGTTCTCGGTCATTCAGCGTACACGTCGCCGTTGGTTCCTCG
ACAAGCTGGTGGACGAGATCGGTGTGGGTTACGTGCGTGACAGGGATACGACCA
GCGAATACAGACTGTCCCAGATCAAGCCTTTGCATAATTTTTTAACACAACTACA
ACCTTTTCTAAAACTAAAACAAAAACAAGCAAATTTAGTTTTAAAAATTATTGAA
CAACTTCCGTCAGCAAAAGAATCCCCGGACAAATTCTTAGAAGTTTGTACATGGG
TGGATCAAATTGCAGCTCTGAATGATTCGAGGACGCGTAAAACAACTTCTGAAA
CCGTTCGTGCTGTGCTAGACAGTTTACCAGGATCCGTGGGAGGTCTATCGCCATC
TCAGGCATCCAGCGCCGCATCCTCGGCTTCCTCAAGCCCGGGTTCAGGGATCTCC
GAAGCACTCAGAGCTGGAGCAGGTTCCGGCACTGGATACAACAAGGAATTCCTG
CTCTACCTGGCGGGCTTCGTCGACGGGGACGGCTCCATCTATGCCAGTATCGATC
CTGATCAACGGAGTAAGTTCAAGCACGGGCTGAGGCTCAATTTCCAGGTCTCTCA
GAAGACACAGCGCCGTTGGTTCCTCGACAAGCTGGTGGACGAGATCGGTGTGGG
TTACGTGCAGGACAAGGGCAGCGTCTCCCATTACATTCTGTCCGAGATCAAGCCT
CTGCACAACTTCCTGACCCAGCTCCAGCCCTTCCTGAAGCTCAAGCAGAAGCAGG
CCAACCTCGTGCTGAAGATCATCGAGCAGCTGCCCTCCGCCAAGGAATCCCCGG
ACAAGTTCCTGGAGGTGTGCACCTGGGTGGACCAGATCGCCGCTCTGAACGACTC
CAAGACCCGCAAGACCACTTCCGAAACCGTCCGCGCCGTTCTAGACAGTCTCTCC
GAGAAGAAGAAGTCGTCCCCCTAA

SEQ ID NO: 69
ATGAATACAAAATATAATAAAGAGTTCTTACTCTACTTAGCAGGGTTTGTAGACG
CTGACGGTTCCATCTATGCCTGTATCACGCCTCGTCAAACGCATAAGTTCAAGCA
CAATCTGGCGCTCGGGTTCAGTGTCATTCAGCGTACACGTCGCCGTTGGTTCCTT
GACAAGCTGGTGGACGAGATCGGTGTGGGTTACGTGCGTGACAGGGATACGACC
AGCGAATACAGACTGTCCCAGATCAAGCCTTTGCATAATTTTTTAACACAACTAC
AACCTTTTCTAAAACTAAAACAAAAACAAGCAAATTTAGTTTTAAAAATTATTGA
ACAACTTCCGTCAGCAAAAGAATCCCCGGACAAATTCTTAGAAGTTTGTACATGG
GTGGATCAAATTGCAGCTCTGAATGATTCGAGGACGCGTAAAACAACTTCTGAA
ACCGTTCGTGCTGTGCTAGACAGTTTACCAGGATCCGTGGGAGGTCTATCGCCAT
CTCAGGCATCCAGCGCCGCATCCTCGGCTTCCTCAAGCCCGGGTTCAGGGATCTC
CGAAGCACTCAGAGCTGGAGCAGGTTCCGGCACTGGATACAACAAGGAATTCCT
GCTCTACCTGGCGGGCTTCGTCGACGGGGACGGCTCCATCTATGCCAGTATCGAT
CCTGATCAACGGAGTAAGTTCAAGCACGGGCTGAGGCTCAATTTCCAGGTCTCTC
AGAAGACACAGCGCCGTTGGTTCCTCGACAAGCTGGTGGACGAGATCGGTGTGG
GTTACGTGCAGGACAAGGGCAGCGTCTCCCATTACATTCTGTCCGAGATCAAGCC
TCTGCACAACTTCCTGACCCAGCTCCAGCCCTTCCTGAAGCTCAAGCAGAAGCAG
GCCAACCTCGTGCTGAAGATCATCGAGCAGCTGCCCTCCGCCAAGGAATCCCCG
GACAAGTTCCTGGAGGTGTGCACCTGGGTGGACCAGATCGCCGCTCTGAACGAC
TCCAAGACCCGCAAGACCACTTCCGAAACCGTCCGCGCCGTTCTAGACAGTCTCT
CCGAGAAGAAGAAGTCGTCCCCCTAA

SEQ ID NO: 70
ATGAATACAAAATATAATAAAGAGTTCTTACTCTACTTAGCAGGGTTTGTAGACG
GTGACGGTTCCATCTTCGCCTCCATTGAACCAGCGCAACGGGCGAAGTTCAAGCA
CTATCTGCGTCTCGTGTTCAATGTCACTCAGAAGACACAGCGCCGTTGGTTCCTC
GACAAGCTGGTGGACGAGATCGGTGTGGGTTACGTGTCTGACTCTGGCAGCGTCT

-continued

| Sequence Listing |
|---|
| CCCTTTACAAGCTCAGCGAAATTAAACCATTGCATAATTTTTTAACACAACTACA |
| ACCTTTTCTAAAACTAAAACAAAAACAAGCAAATTTAGTTTTAAAAATTATTGAA |
| CAACTTCCGTCAGCAAAAGAATCCCCGGACAAATTCTTAGAAGTTTGTACATGGG |
| TGGATCAAATTGCAGCTCTGAATGATTCGAAGACGCGTAAAACAACTTCTGAAA |
| CCGTTCGTGCTGTGCTAGACAGTTTACCAGGATCCGTGGGAGGTCTATCGCCATC |
| TCAGGCATCCAGCGCCGCATCCTCGGCTTCCTCAAGCCCGGGTTCAGGGATCTCC |
| GAAGCACTCAGAGCTGGAGCAGGTTCCGGCACTGGATACAACAAGGAATTCCTG |
| CTCTACCTGGCGGGCTTCGTCGACAGCGACGGCTCCATCTTTGCCAGTATCGTGC |
| CTGATCAATCGCGTAAGTTCAAGCATGCTCTCCGGTTGCGCTTTATTGTCAGTCA |
| GAATACAAGGCGCCGTTGGTTCCTCGACAAGCTGGTGGACGAGATCGGTGTGGG |
| TTACGTGAAGGACTCTGGTCGGAGCGCCCATTATACTCTGTCCGAGATCAAGCCT |
| CTGCACAACTTCCTGACCCAGCTCCAGCCCTTCCTGAAGCTCAAGCAGAAGCAGG |
| CCAACCTCGTGCTGAAGATCATCGAGCAGCTGCCCTCCGCCAAGGAATCCCCGG |
| ACAAGTTCCTGGAGGTGTGCACCTGGGTGGACCAGATCGCCGCTCTGAACGACTC |
| CAAGACCCGCAAGACCACTTCCGAAACCGTCCGCGCCGTTCTAGACAGTCTCTCC |
| GAGAAGAAGAAGTCGTCCCCCTAA |

The invention claimed is:

1. An engineered meganuclease that binds and cleaves a recognition sequence in a transthyretin (TTR) gene, wherein said engineered meganuclease comprises a first subunit and a second subunit, wherein said first subunit binds to a first recognition half-site of said recognition sequence and comprises a first hypervariable (HVR1) region, wherein said second subunit binds to a second recognition half-site of said recognition sequence and comprises a second hypervariable (HVR2) region, and wherein:

(a) said recognition sequence consists of SEQ ID NO: 7 and said engineered meganuclease comprises an amino acid sequence of any one of SEQ ID NOs: 11-14; or (b) said recognition sequence consists of SEQ ID NO: 9 and said engineered meganuclease comprises the amino acid sequence of SEQ ID NO: 15.

2. A polynucleotide comprising a nucleic acid sequence encoding said engineered meganuclease of claim 1.

3. The polynucleotide of claim 2, wherein said polynucleotide is an mRNA.

4. A recombinant DNA construct comprising a polynucleotide comprising a nucleic acid sequence encoding said engineered meganuclease of claim 1.

5. A recombinant virus comprising a polynucleotide comprising a nucleic acid sequence encoding said engineered meganuclease of claim 1.

6. The recombinant virus of claim 5, wherein said recombinant virus is a recombinant AAV.

7. The recombinant virus of claim 6, wherein said recombinant AAV has an AAV8 serotype.

8. The recombinant virus of claim 5, wherein said nucleic acid sequence comprises a promoter sequence operably linked to said nucleic acid sequence encoding said engineered meganuclease.

9. The recombinant virus of claim 8, wherein said promoter is a liver specific promoter.

10. A method for producing a genetically-modified human liver cell comprising a modified TTR gene, said method comprising introducing into a human liver cell:

(a) a polynucleotide comprising a nucleic acid sequence encoding an engineered meganuclease of claim 1, wherein said engineered meganuclease is expressed in said eukaryotic cell; or (b) said engineered meganuclease of claim 1;

wherein said engineered meganuclease produces a cleavage site within said recognition sequence consisting of SEQ ID NO: 7 or SEQ ID NO: 9 and generates a modified TTR gene comprising an insertion or deletion that does not encode a full-length endogenous TTR polypeptide.

11. The method of claim 10, wherein said method is performed in vitro.

12. The method of claim 10, wherein said method is performed in vivo.

13. The method of claim 10, wherein said polynucleotide is introduced into said human liver cell by an mRNA or a recombinant AAV.

14. A genetically-modified human liver cell prepared by the method of claim 10.

15. A pharmaceutical composition comprising a pharmaceutically-acceptable carrier and said engineered meganuclease, or a polynucleotide comprising a nucleic acid sequence encoding said engineered meganuclease, of claim 1.

16. A lipid nanoparticle composition comprising lipid nanoparticles comprising a polynucleotide, wherein said polynucleotide comprises a nucleic acid sequence encoding said engineered meganuclease of claim 1.

17. The lipid nanoparticle composition of claim 16, wherein said polynucleotide is an mRNA.

* * * * *

SEQUENCE LISTING

<160> NUMBER OF SEQ ID NOS: 70

<210> SEQ ID NO 1
<211> LENGTH: 163
<212> TYPE: PRT
<213> ORGANISM: Chlamydomonas reinhardtii

<400> SEQUENCE: 1

```
Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro
```

<210> SEQ ID NO 2
<211> LENGTH: 9
<212> TYPE: PRT
<213> ORGANISM: Chlamydomonas reinhardtii

<400> SEQUENCE: 2

```
Leu Ala Gly Leu Ile Asp Ala Asp Gly
1               5
```

<210> SEQ ID NO 3

<211> LENGTH: 7258
<212> TYPE: DNA
<213> ORGANISM: Homo sapiens

<400> SEQUENCE: 3
gttgactaag tcaataatca gaatcagcag gtttgcagtc agattggcag ggataagcag 60
cctagctcag gagaagtgag tataaaagcc ccaggctggg agcagccatc acagaagtcc 120
actcattctt ggcaggatgg cttctcatcg tctgctcctc ctctgccttg ctggactggt 180
atttgtgtct gaggctggcc ctacggtgag tgtttctgtg acatcccatt cctacattta 240
agattcacgc taaatgaagt agaagtgact ccttccagct ttgccaacca gcttttatta 300
ctagggcaag ggtacccagc atctattttt aatataatta attcaaactt caaaaagaat 360
gaagttccac tgagcttact gagctgggac ttgaactctg agcattctac ctcattgctt 420
tggtgcatta ggtttgtaat atctggtacc tctgtttcct cagatagatg atagaaataa 480
agatatgata ttaaggaagc tgttaatact gaattttcag aaaagtatcc ctccataaaa 540
tgtatttggg ggacaaactg caggagatta tattctggcc ctatagttat tcaaaacgta 600
tttattgatt aatctttaaa aggcttagtg aacaatattc tagtcagata tctaattctt 660
aaatcctcta gaagaattaa ctaatactat aaaatgggtc tggatgtagt tctgacatta 720
ttttataaca actggtaaga gggagtgact atagcaacaa ctaaaatgat ctcaggaaaa 780
cctgtttggc cctatgtatg gtacattaca tcttttcagt aattccactc aaatggagac 840
ttttaacaaa gcaactgttc tcaggggacc tattttctcc cttaaaattc attatacaca 900
tccctggttg atagcagtgt gtctggaggc agaaaccatt cttgctttgg aaacaattac 960
gtctgtgtta tactgagtag ggaagctcat taattgtcga cacttacgtt cctgataatg 1020
ggatcagtgt gtaattcttg tttcgctcca gatttctaat accacaaaga ataaatcctt 1080
tcactctgat caattttgtt aacttctcac gtgtcttctc tacacccagg gcaccggtga 1140
atccaagtgt cctctgatgg tcaaagttct agatgctgtc cgaggcagtc ctgccatcaa 1200
tgtggccgtg catgtgttca gaaaggctgc tgatgacacc tgggagccat ttgcctctgg 1260
gtaagttgcc aaagaaccct cccacaggac ttggttttat cttcccgttt gcccctcact 1320
tggtagagag aggctcacat catctgctaa agaatttaca agtagattga aaaacgtagg 1380
cagaggtcaa gtatgccctc tgaaggatgc cctcttttg ttttgcttag ctaggaagtg 1440
accaggaacc tgagcatcat ttaggggcag acagtagaga aaagaaggaa tcagaactcc 1500
tctcctctag ctgtggtttg caaccctttt gggtcacaga acactttatg taggtgatga 1560
aaagtaaaca ttctatgccc agaaaaaatg cacagataca cacacataca aaatcatata 1620
tgtgatttta ggagtttcac agattccctg gtgtccctgg gtaacaccaa agctaagtgt 1680
ccttgtctta gaattttagg aaaaggtata atgtgtatta acccattaac aaaaggaaag 1740
gaattcagaa atattattaa ccaggcatct gtctgtagtt aatatggatc acccaaaacc 1800
caaggctttt gcctaatgaa cactttgggg cacctactgt gtgcaaggct gggggctgtc 1860
aagctcagtt aaaaaaaaaa agatagaaga gatggatcca tgaggcaaag tacagcccca 1920
ggctaatccc acgatcaccc gacttcatgt ccaagagtgg cttctcacct tcattagcca 1980
gttcacaatt ttcatggagt ttttctacct gcactagcaa aaacttcaag gaaaatacat 2040
attaataaat ctaagcaaag tgaccagaag acagagcaat caggagaccc tttgcatcca 2100
gcagaagagg aactgctaag tatttacatc tccacagaga agaatttctg ttgggtttta 2160
attgaacccc aagaaccaca tgattcttca accattattg ggaagatcat tttcttaggt 2220
ctggttttaa ctggcttttt atttgggaat tcatttatgt ttatataaaa tgccaagcat 2280
aacatgaaaa gtggttacag gactattcta agggagagac agaatggaca ccaaaaatat 2340
tccaatgttc ttgtgaatct tttccttgca ccaggacaaa aaaaaaaaga agtgaaaaga 2400
agaaaggagg aggggcataa tcagagtcag taaagacaac tgctattttt atctatcgta 2460
gctgttgcag tcaaatggga agcaatttcc aacattcaac tatggagctg gtacttacat 2520
ggaaatagaa gttgcctagt gtttgttgct ggcaaagagt tatcagagag gttaaatata 2580
taaaagggaa aagagtcaga tacaggttct tcttcctact ttaggttttc cactgtgtgt 2640
gcaaatgata ctccctggtg gtgtgcagat gcctcaaagc tatcctcaca ccacaaggga 2700
gaggagcgag atcctgctgt cctggagaag tgcagagtta gaacagctgt ggccacttgc 2760
atccaatcat caatcttgaa tcacagggac tctttcttaa gtaaacatta tacctggccg 2820
ggcacggtgg ctcacgcctg taatcccagc actttgggat gccaaagtgg gcatatcatc 2880
tgaggtcagg agttcaagac cagcctggcc aacatggcaa aactccgtct ttatgaaaaa 2940
tacaaaaatt agccaggcat ggtggcaggc gcctgtaatc ccagctaatt gggaggctga 3000
ggctggagaa tcccttgaat ctaggaggca gaggttgcag tgagctgaga tcgtgccatt 3060
gcactccagc ctgggtgaca agagtaaaac tctgtctcaa aaaaaaaaaa ttatacctac 3120
attctcttct tatcagagaa aaaaatctac agtgagcttt tcaaaaagtt tttacaaact 3180
ttttgccatt taatttcagt taggagtttt ccctacttct gacttagttg aggggaaatg 3240
ttcataacat gtttataaca tgtttatgtg tgttagttgg tgggggtgta ttactttgcc 3300
atgccatttg tttcctccat gcgtaactta atccagactt tcacacctta taggaaaacc 3360
agtgagtctg gagagctgca tgggctcaca actgaggagg aatttgtaga agggatatac 3420
aaagtggaaa tagacaccaa atcttactgg aaggcacttg gcatctcccc attccatgag 3480
catgcagagg tgagtataca gaccttcgag ggttgttttg gttttggttt ttgcttttgg 3540
cattccagga aatgcacagt tttactcagt gtaccacaga aatgtcctaa ggaaggtgat 3600
gaatgaccaa aggttccctt tcctattata caagaaaaaa ttcacaacac tctgagaagc 3660
aaatttcttt ttgactttga tgaaaatcca cttagtaaca tgacttgaac ttacatgaaa 3720
ctactcatag tctattcatt ccactttata tgaatattga tgtatctgct gttgaaataa 3780
tagtttatga ggcagccctc cagaccccac gtagagtgta tgtaacaaga gatgcaccat 3840
tttatttctc gaaaacccgt aacattcttc attccaaaac acatctggct tctcggaggt 3900
ctggacaagt gattcttggc aacacatacc tatagagaca ataaaatcaa agtaataatg 3960
gcaacacaat agataacatt taccaagcat acaccatgtg gcagacacaa ttataagtgt 4020
tttccatatt taacctactt aatcctcagg aataagccac tgaggtcagt cctattatta 4080
tccccatctt atagatgaag aaaatgaggc accaggaagt caaataactt gtcaaaggtc 4140
acaagactag gaaatacaca agtagaaatg tttacaatta aggcccaggc tgggtttgcc 4200
ctcagttctg ctatgcctcg cattatgccc caggaaactt tttcccttgt gaaagccaag 4260
cttaaaaaaa gaaaagccac atttgtaacg tgctctgttc ccctgcctat ggtgaggatc 4320
ttcaaacagt tatacatgga cccagtcccc ctgccttctc cttaatttct taagtcattt 4380
gaaacagatg gctgtcatgg aaatagaatc cagacatgtt ggtcagagtt aaagatcaac 4440
taattccatc aaaaatagct cggcatgaaa gggaactatt ctctggctta gtcatggatg 4500
agactttcaa ttgctataaa gtggttcctt tattagacaa tgttaccagg gaaacaacag 4560
gggtttgttt gacttctggg gcccacaagt caacaagaga gccccatcta ccaaggagca 4620
tgtccctgac taccccctcag ccagcagcaa gacatggacc ccagtcaggg caggagcagg 4680
gtttcggcgg cgcccagcac aagacattgc ccctagagtc tcagccccta ccctcgagta 4740
atagatctgc ctacctgaga ctgttgtttg cccaagagct gggtctcagc ctgatgggaa 4800
ccatataaaa aggttcactg acatactgcc cacatgttgt tctctttcat tagatcttag 4860
cttccttgtc tgctcttcat tcttgcagta ttcattcaac aaacattaaa aaaaaaaaaa 4920
agcattctat gtgtggaaca ctctgctaga tgctgtggat ttagaaatga aaatacatcc 4980
cgacccttgg aatggaaggg aaaggactga agtaagacag attaagcagg accgtcagcc 5040
cagcttgaag cccagataaa tacggagaac aagagagagc gagtagtgag agatgagtcc 5100
caatgcctca ctttggtgac gggtgcgtgg tgggcttcat gcagcttctt ctgataaatg 5160
cctccttcag aactggtcaa ctctaccttg gccagtgacc caggtggtca tagtagattt 5220
accaagggaa aatggaaact tttattagga gctcttaggc ctcttcactt catggatttt 5280
tttttccttt ttttttgaga tggagttttg ccctgtcacc caggctggaa tgcagtggtg 5340
caatctcagc tcactgcaac ctccgcctcc caggttcaag caattctcct gcctcagcct 5400
cccgagtagc tgggactaca ggtgtgcgcc accacaccag gctaattttt gtattttttg 5460
taaagacagg ttttcaccac gttggccagg ctggtctgaa ctccagacct caggtgattc 5520
acctgtctca gcctcccaaa gtgctgggat tacaggtgtg agccaccgtg cccggctact 5580
tcatggattt ttgattacag attatgcctc ttacaatttt taagaagaat caagtgggct 5640
gaaggtcaat gtcaccataa gacaaaagac atttttatta gttgattcta gggaattggc 5700
cttaagggga gccctttctt cctaagagat tcttaggtga ttctcacttc ctcttgcccc 5760
agtattattt ttgtttttgg tatggctcac tcagatcctt ttttcctcct atccctaagt 5820
aatccgggtt tctttttccc atatttagaa caaaatgtat ttatgcagag tgtgtccaaa 5880
cctcaaccca aggcctgtat acaaaataaa tcaaattaaa cacatcttta ctgtcttcta 5940
cctctttcct gacctcaata tatcccaact tgcctcactc tgagaaccaa ggctgtccca 6000
gcacctgagt cgcagatatt ctactgattt gacagaactg tgtgactatc tggaacagca 6060
ttttgatcca caatttgccc agttacaaag cttaaatgag ctctagtgca tgcatatata 6120
tttcaaaatt ccaccatgat cttccacact ctgtattgta aatagagccc tgtaatgctt 6180
ttacttcgta tttcattgct tgttatacat aaaaatatac ttttcttctt catgttagaa 6240
aatgcaaaga ataggagggt gggggaatct ctgggcttgg agacaggaga cttgccttcc 6300
tactatggtt ccatcagaat gtagactggg acaatacaat aattcaagtc tggtttgctc 6360
atctgtaaat tgggaagaat gtttccagct ccagaatgct aaatctctaa gtctgtggtt 6420
ggcagccact attgcagcag ctcttcaatg actcaatgca gttttgcatt ctccctacct 6480
ttttttttcta aaaccaataa aatagataca gcctttaggc tttctgggat ttcccttagt 6540
caagctaggg tcatcctgac tttcggcgtg aatttgcaaa acaagacctg actctgtact 6600
cctgctctaa ggactgtgca tggttccaaa ggcttagctt gccagcatat ttgagctttt 6660
tccttctgtt caaactgttc caaaatataa aagaataaaa ttaattaagt tggcactgga 6720
cttccggtgg tcagtcatgt gtgtcatctg tcacgttttt cgggctctgg tggaaatgga 6780
tctgtctgtc ttctctcata ggtggtattc acagccaacg actccggccc ccgccgctac 6840
accattgccg ccctgctgag cccctactcc tattccacca cggctgtcgt caccaatccc 6900
aaggaatgag ggacttctcc tccagtggac ctgaaggacg agggatggga tttcatgtaa 6960
ccaagagtat tccattttta ctaaagcagt gttttcacct catatgctat gttagaagtc 7020
caggcagaga caataaaaca ttcctgtgaa aggcactttt cattccactt taacttgatt 7080
ttttaaattc ccttattgtc ccttccaaaa aaaagagaat caaaatttta caaagaatca 7140
aaggaattct agaaagtatc tgggcagaac gctaggagag atccaaattt ccattgtctt 7200
gcaagcaaag cacgtattaa atatgatctg cagccattaa aaagacacat tctgtaaa 7258

<210> SEQ ID NO 4
<211> LENGTH: 147
<212> TYPE: PRT
<213> ORGANISM: Homo sapiens

<400> SEQUENCE: 4

```
Met Ala Ser His Arg Leu Leu Leu Leu Cys Leu Ala Gly Leu Val Phe
1               5                   10                  15

Val Ser Glu Ala Gly Pro Thr Gly Thr Gly Glu Ser Lys Cys Pro Leu
            20                  25                  30

Met Val Lys Val Leu Asp Ala Val Arg Gly Ser Pro Ala Ile Asn Val
        35                  40                  45

Ala Val His Val Phe Arg Lys Ala Ala Asp Asp Thr Trp Glu Pro Phe
    50                  55                  60

Ala Ser Gly Lys Thr Ser Glu Ser Gly Glu Leu His Gly Leu Thr Thr
65                  70                  75                  80

Glu Glu Glu Phe Val Glu Gly Ile Tyr Lys Val Glu Ile Asp Thr Lys
                85                  90                  95

Ser Tyr Trp Lys Ala Leu Gly Ile Ser Pro Phe His Glu His Ala Glu
            100                 105                 110

Val Val Phe Thr Ala Asn Asp Ser Gly Pro Arg Arg Tyr Thr Ile Ala
        115                 120                 125

Ala Leu Leu Ser Pro Tyr Ser Tyr Ser Thr Thr Ala Val Val Thr Asn
    130                 135                 140

Pro Lys Glu
145
```

<210> SEQ ID NO 5
<211> LENGTH: 127
<212> TYPE: PRT
<213> ORGANISM: Homo sapiens

<400> SEQUENCE: 5

```
Gly Pro Thr Gly Thr Gly Glu Ser Lys Cys Pro Leu Met Val Lys Val
1               5                   10                  15

Leu Asp Ala Val Arg Gly Ser Pro Ala Ile Asn Val Ala Val His Val
            20                  25                  30

Phe Arg Lys Ala Ala Asp Asp Thr Trp Glu Pro Phe Ala Ser Gly Lys
        35                  40                  45

Thr Ser Glu Ser Gly Glu Leu His Gly Leu Thr Thr Glu Glu Glu Phe
    50                  55                  60

Val Glu Gly Ile Tyr Lys Val Glu Ile Asp Thr Lys Ser Tyr Trp Lys
65                  70                  75                  80

Ala Leu Gly Ile Ser Pro Phe His Glu His Ala Glu Val Val Phe Thr
                85                  90                  95

Ala Asn Asp Ser Gly Pro Arg Arg Tyr Thr Ile Ala Ala Leu Leu Ser
            100                 105                 110

Pro Tyr Ser Tyr Ser Thr Thr Ala Val Val Thr Asn Pro Lys Glu
```

115 120 125

<210> SEQ ID NO 6
<211> LENGTH: 127
<212> TYPE: PRT
<213> ORGANISM: Homo sapiens

<400> SEQUENCE: 6

Gly Pro Thr Gly Thr Gly Glu Ser Lys Cys Pro Leu Met Val Lys Val
1 5 10 15

Leu Asp Ala Val Arg Gly Ser Pro Ala Ile Asn Val Ala Met His Val
20 25 30

Phe Arg Lys Ala Ala Asp Asp Thr Trp Glu Pro Phe Ala Ser Gly Lys
35 40 45

Thr Ser Glu Ser Gly Glu Leu His Gly Leu Thr Thr Glu Glu Glu Phe
50 55 60

Val Glu Gly Ile Tyr Lys Val Glu Ile Asp Thr Lys Ser Tyr Trp Lys
65 70 75 80

Ala Leu Gly Ile Ser Pro Phe His Glu His Ala Glu Val Val Phe Thr
85 90 95

Ala Asn Asp Ser Gly Pro Arg Arg Tyr Thr Ile Ala Ala Leu Leu Ser
100 105 110

Pro Tyr Ser Tyr Ser Thr Thr Ala Val Val Thr Asn Pro Lys Glu
115 120 125

<210> SEQ ID NO 7
<211> LENGTH: 22
<212> TYPE: DNA
<213> ORGANISM: Homo sapiens

<400> SEQUENCE: 7
tgcatgggct cacaactgag ga 22

<210> SEQ ID NO 8
<211> LENGTH: 22
<212> TYPE: DNA
<213> ORGANISM: Homo sapiens

<400> SEQUENCE: 8
acgtacccga gtgttgactc ct 22

<210> SEQ ID NO 9
<211> LENGTH: 22
<212> TYPE: DNA
<213> ORGANISM: Homo sapiens

<400> SEQUENCE: 9
gctggactgg tatttgtgtc tg 22

<210> SEQ ID NO 10
<211> LENGTH: 22
<212> TYPE: DNA
<213> ORGANISM: Homo sapiens

<400> SEQUENCE: 10
cgacctgacc ataaacacag ac 22

<210> SEQ ID NO 11
<211> LENGTH: 354
<212> TYPE: PRT
<213> ORGANISM: Artificial Sequence
<220> FEATURE:
<223> OTHER INFORMATION: Synthesized

<400> SEQUENCE: 11

```
Met Asn Thr Lys Tyr Asn Lys Glu Phe Leu Leu Tyr Leu Ala Gly Phe
1               5                   10                  15

Val Asp Ala Asp Gly Ser Ile Tyr Ala Cys Ile Thr Pro Arg Gln Thr
            20                  25                  30

His Lys Phe Lys His Val Leu Ala Leu Gly Phe Ser Val Ile Gln Arg
        35                  40                  45

Thr Arg Arg Arg Trp Phe Leu Asp Lys Leu Val Asp Glu Ile Gly Val
    50                  55                  60

Gly Tyr Val Arg Asp Arg Asp Thr Thr Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Arg Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Asp Pro Asp Gln Arg Ser
    210                 215                 220

Lys Phe Lys His Gly Leu Arg Leu Asn Phe Gln Val Ser Gln Lys Thr
225                 230                 235                 240

Gln Arg Arg Trp Phe Leu Asp Lys Leu Val Asp Glu Ile Gly Val Gly
                245                 250                 255

Tyr Val Gln Asp Lys Gly Ser Val Ser His Tyr Ile Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 12
<211> LENGTH: 354
<212> TYPE: PRT
<213> ORGANISM: Artificial Sequence
<220> FEATURE:

<223> OTHER INFORMATION: Synthesized

<400> SEQUENCE: 12

Met Asn Thr Lys Tyr Asn Lys Glu Phe Leu Leu Tyr Leu Ala Gly Phe
1 5 10 15

Val Asp Ala Asp Gly Ser Ile Tyr Ala Cys Ile Thr Pro Arg Gln Asp
20 25 30

Tyr Lys Phe Lys His Asn Leu Ala Leu Gly Phe Ser Val Ile Gln Arg
35 40 45

Thr Arg Arg Arg Trp Phe Leu Asp Lys Leu Val Asp Glu Ile Gly Val
50 55 60

Gly Tyr Val Arg Asp Arg Asp Thr Thr Ser Glu Tyr Arg Leu Ser Gln
65 70 75 80

Ile Lys Pro Leu His Asn Phe Leu Thr Gln Leu Gln Pro Phe Leu Lys
85 90 95

Leu Lys Gln Lys Gln Ala Asn Leu Val Leu Lys Ile Ile Glu Gln Leu
100 105 110

Pro Ser Ala Lys Glu Ser Pro Asp Lys Phe Leu Glu Val Cys Thr Trp
115 120 125

Val Asp Gln Ile Ala Ala Leu Asn Asp Ser Arg Thr Arg Lys Thr Thr
130 135 140

Ser Glu Thr Val Arg Ala Val Leu Asp Ser Leu Pro Gly Ser Val Gly
145 150 155 160

Gly Leu Ser Pro Ser Gln Ala Ser Ser Ala Ala Ser Ser Ala Ser Ser
165 170 175

Ser Pro Gly Ser Gly Ile Ser Glu Ala Leu Arg Ala Gly Ala Gly Ser
180 185 190

Gly Thr Gly Tyr Asn Lys Glu Phe Leu Leu Tyr Leu Ala Gly Phe Val
195 200 205

Asp Gly Asp Gly Ser Ile Tyr Ala Ser Ile Asp Pro Asp Gln Arg Ser
210 215 220

Lys Phe Lys His Gly Leu Arg Leu Asn Phe Gln Val Ser Gln Lys Thr
225 230 235 240

Gln Arg Arg Trp Phe Leu Asp Lys Leu Val Asp Glu Ile Gly Val Gly
245 250 255

Tyr Val Gln Asp Lys Gly Ser Val Ser His Tyr Ile Leu Ser Glu Ile
260 265 270

Lys Pro Leu His Asn Phe Leu Thr Gln Leu Gln Pro Phe Leu Lys Leu
275 280 285

Lys Gln Lys Gln Ala Asn Leu Val Leu Lys Ile Ile Glu Gln Leu Pro
290 295 300

Ser Ala Lys Glu Ser Pro Asp Lys Phe Leu Glu Val Cys Thr Trp Val
305 310 315 320

Asp Gln Ile Ala Ala Leu Asn Asp Ser Lys Thr Arg Lys Thr Thr Ser
325 330 335

Glu Thr Val Arg Ala Val Leu Asp Ser Leu Ser Glu Lys Lys Lys Ser
340 345 350

Ser Pro

<210> SEQ ID NO 13
<211> LENGTH: 354
<212> TYPE: PRT
<213> ORGANISM: Artificial Sequence
<220> FEATURE:
<223> OTHER INFORMATION: Synthesized

<400> SEQUENCE: 13

Met Asn Thr Lys Tyr Asn Lys Glu Phe Leu Leu Tyr Leu Ala Gly Phe
1               5                   10                  15

Val Asp Ala Asp Gly Ser Ile Tyr Ala Cys Ile Thr Pro Arg Gln Leu
            20                  25                  30

Cys Lys Phe Lys His Gly Leu Ala Leu Gly Phe Ser Val Ile Gln Arg
        35                  40                  45

Thr Arg Arg Arg Trp Phe Leu Asp Lys Leu Val Asp Glu Ile Gly Val
    50                  55                  60

Gly Tyr Val Arg Asp Arg Asp Thr Thr Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Arg Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Ser Ile Asp Pro Asp Gln Arg Ser
    210                 215                 220

Lys Phe Lys His Gly Leu Arg Leu Asn Phe Gln Val Ser Gln Lys Thr
225                 230                 235                 240

Gln Arg Arg Trp Phe Leu Asp Lys Leu Val Asp Glu Ile Gly Val Gly
                245                 250                 255

Tyr Val Gln Asp Lys Gly Ser Val Ser His Tyr Ile Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 14
<211> LENGTH: 354
<212> TYPE: PRT
<213> ORGANISM: Artificial Sequence
<220> FEATURE:
<223> OTHER INFORMATION: Synthesized

<400> SEQUENCE: 14

Met Asn Thr Lys Tyr Asn Lys Glu Phe Leu Leu Tyr Leu Ala Gly Phe
1 5 10 15

Val Asp Ala Asp Gly Ser Ile Tyr Ala Cys Ile Thr Pro Arg Gln Thr
20 25 30

His Lys Phe Lys His Asn Leu Ala Leu Gly Phe Ser Val Ile Gln Arg
35 40 45

Thr Arg Arg Arg Trp Phe Leu Asp Lys Leu Val Asp Glu Ile Gly Val
50 55 60

Gly Tyr Val Arg Asp Arg Asp Thr Thr Ser Glu Tyr Arg Leu Ser Gln
65 70 75 80

Ile Lys Pro Leu His Asn Phe Leu Thr Gln Leu Gln Pro Phe Leu Lys
85 90 95

Leu Lys Gln Lys Gln Ala Asn Leu Val Leu Lys Ile Ile Glu Gln Leu
100 105 110

Pro Ser Ala Lys Glu Ser Pro Asp Lys Phe Leu Glu Val Cys Thr Trp
115 120 125

Val Asp Gln Ile Ala Ala Leu Asn Asp Ser Arg Thr Arg Lys Thr Thr
130 135 140

Ser Glu Thr Val Arg Ala Val Leu Asp Ser Leu Pro Gly Ser Val Gly
145 150 155 160

Gly Leu Ser Pro Ser Gln Ala Ser Ser Ala Ala Ser Ser Ala Ser Ser
165 170 175

Ser Pro Gly Ser Gly Ile Ser Glu Ala Leu Arg Ala Gly Ala Gly Ser
180 185 190

Gly Thr Gly Tyr Asn Lys Glu Phe Leu Leu Tyr Leu Ala Gly Phe Val
195 200 205

Asp Gly Asp Gly Ser Ile Tyr Ala Ser Ile Asp Pro Asp Gln Arg Ser
210 215 220

Lys Phe Lys His Gly Leu Arg Leu Asn Phe Gln Val Ser Gln Lys Thr
225 230 235 240

Gln Arg Arg Trp Phe Leu Asp Lys Leu Val Asp Glu Ile Gly Val Gly
245 250 255

Tyr Val Gln Asp Lys Gly Ser Val Ser His Tyr Ile Leu Ser Glu Ile
260 265 270

Lys Pro Leu His Asn Phe Leu Thr Gln Leu Gln Pro Phe Leu Lys Leu
275 280 285

Lys Gln Lys Gln Ala Asn Leu Val Leu Lys Ile Ile Glu Gln Leu Pro
290 295 300

Ser Ala Lys Glu Ser Pro Asp Lys Phe Leu Glu Val Cys Thr Trp Val
305 310 315 320

Asp Gln Ile Ala Ala Leu Asn Asp Ser Lys Thr Arg Lys Thr Thr Ser
325 330 335

Glu Thr Val Arg Ala Val Leu Asp Ser Leu Ser Glu Lys Lys Lys Ser
340 345 350

Ser Pro

<210> SEQ ID NO 15
<211> LENGTH: 354
<212> TYPE: PRT
<213> ORGANISM: Artificial Sequence
<220> FEATURE:
<223> OTHER INFORMATION: Synthesized

<400> SEQUENCE: 15

```
Met Asn Thr Lys Tyr Asn Lys Glu Phe Leu Leu Tyr Leu Ala Gly Phe
1               5                   10                  15

Val Asp Gly Asp Gly Ser Ile Phe Ala Ser Ile Glu Pro Ala Gln Arg
            20                  25                  30

Ala Lys Phe Lys His Tyr Leu Arg Leu Val Phe Asn Val Thr Gln Lys
        35                  40                  45

Thr Gln Arg Arg Trp Phe Leu Asp Lys Leu Val Asp Glu Ile Gly Val
    50                  55                  60

Gly Tyr Val Ser Asp Ser Gly Ser Val Ser Leu Tyr Lys Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Ser Asp Gly Ser Ile Phe Ala Ser Ile Val Pro Asp Gln Ser Arg
    210                 215                 220

Lys Phe Lys His Ala Leu Arg Leu Arg Phe Ile Val Ser Gln Asn Thr
225                 230                 235                 240

Arg Arg Arg Trp Phe Leu Asp Lys Leu Val Asp Glu Ile Gly Val Gly
                245                 250                 255

Tyr Val Lys Asp Ser Gly Arg Ser Ala His Tyr Thr Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 16
<211> LENGTH: 147
<212> TYPE: PRT
<213> ORGANISM: Artificial Sequence
<220> FEATURE:
<223> OTHER INFORMATION: Synthesized

<400> SEQUENCE: 16

```
Lys Glu Phe Leu Leu Tyr Leu Ala Gly Phe Val Asp Ala Asp Gly Ser
1               5                   10                  15

Ile Tyr Ala Cys Ile Thr Pro Arg Gln Thr His Lys Phe Lys His Val
            20                  25                  30

Leu Ala Leu Gly Phe Ser Val Ile Gln Arg Thr Arg Arg Arg Trp Phe
        35                  40                  45

Leu Asp Lys Leu Val Asp Glu Ile Gly Val Gly Tyr Val Arg Asp Arg
    50                  55                  60

Asp Thr Thr Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145


<210> SEQ ID NO 17
<211> LENGTH: 147
<212> TYPE: PRT
<213> ORGANISM: Artificial Sequence
<220> FEATURE:
<223> OTHER INFORMATION: Synthesized

<400> SEQUENCE: 17

Lys Glu Phe Leu Leu Tyr Leu Ala Gly Phe Val Asp Ala Asp Gly Ser
1               5                   10                  15

Ile Tyr Ala Cys Ile Thr Pro Arg Gln Asp Tyr Lys Phe Lys His Asn
            20                  25                  30

Leu Ala Leu Gly Phe Ser Val Ile Gln Arg Thr Arg Arg Arg Trp Phe
        35                  40                  45

Leu Asp Lys Leu Val Asp Glu Ile Gly Val Gly Tyr Val Arg Asp Arg
    50                  55                  60

Asp Thr Thr Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145


<210> SEQ ID NO 18
<211> LENGTH: 147
<212> TYPE: PRT
<213> ORGANISM: Artificial Sequence
<220> FEATURE:
<223> OTHER INFORMATION: Synthesized

<400> SEQUENCE: 18
```

```
Lys Glu Phe Leu Leu Tyr Leu Ala Gly Phe Val Asp Ala Asp Gly Ser
1               5                   10                  15

Ile Tyr Ala Cys Ile Thr Pro Arg Gln Leu Cys Lys Phe Lys His Gly
            20                  25                  30

Leu Ala Leu Gly Phe Ser Val Ile Gln Arg Thr Arg Arg Arg Trp Phe
        35                  40                  45

Leu Asp Lys Leu Val Asp Glu Ile Gly Val Gly Tyr Val Arg Asp Arg
    50                  55                  60

Asp Thr Thr Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145


<210> SEQ ID NO 19
<211> LENGTH: 147
<212> TYPE: PRT
<213> ORGANISM: Artificial Sequence
<220> FEATURE:
<223> OTHER INFORMATION: Synthesized

<400> SEQUENCE: 19

Lys Glu Phe Leu Leu Tyr Leu Ala Gly Phe Val Asp Ala Asp Gly Ser
1               5                   10                  15

Ile Tyr Ala Cys Ile Thr Pro Arg Gln Thr His Lys Phe Lys His Asn
            20                  25                  30

Leu Ala Leu Gly Phe Ser Val Ile Gln Arg Thr Arg Arg Arg Trp Phe
        35                  40                  45

Leu Asp Lys Leu Val Asp Glu Ile Gly Val Gly Tyr Val Arg Asp Arg
    50                  55                  60

Asp Thr Thr Ser Glu Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145


<210> SEQ ID NO 20
<211> LENGTH: 147
<212> TYPE: PRT
<213> ORGANISM: Artificial Sequence
<220> FEATURE:
<223> OTHER INFORMATION: Synthesized
```

<400> SEQUENCE: 20

```
Lys Glu Phe Leu Leu Tyr Leu Ala Gly Phe Val Asp Gly Asp Gly Ser
1               5                   10                  15

Ile Tyr Ala Ser Ile Asp Pro Asp Gln Arg Ser Lys Phe Lys His Gly
            20                  25                  30

Leu Arg Leu Asn Phe Gln Val Ser Gln Lys Thr Gln Arg Arg Trp Phe
        35                  40                  45

Leu Asp Lys Leu Val Asp Glu Ile Gly Val Gly Tyr Val Gln Asp Lys
    50                  55                  60

Gly Ser Val Ser His Tyr Ile Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 21
<211> LENGTH: 147
<212> TYPE: PRT
<213> ORGANISM: Artificial Sequence
<220> FEATURE:
<223> OTHER INFORMATION: Synthesized

<400> SEQUENCE: 21

```
Lys Glu Phe Leu Leu Tyr Leu Ala Gly Phe Val Asp Gly Asp Gly Ser
1               5                   10                  15

Ile Tyr Ala Ser Ile Asp Pro Asp Gln Arg Ser Lys Phe Lys His Gly
            20                  25                  30

Leu Arg Leu Asn Phe Gln Val Ser Gln Lys Thr Gln Arg Arg Trp Phe
        35                  40                  45

Leu Asp Lys Leu Val Asp Glu Ile Gly Val Gly Tyr Val Gln Asp Lys
    50                  55                  60

Gly Ser Val Ser His Tyr Ile Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145
```

<210> SEQ ID NO 22
<211> LENGTH: 147
<212> TYPE: PRT
<213> ORGANISM: Artificial Sequence
<220> FEATURE:
<223> OTHER INFORMATION: Synthesized

<400> SEQUENCE: 22

Lys Glu Phe Leu Leu Tyr Leu Ala Gly Phe Val Asp Gly Asp Gly Ser
1               5                   10                  15

Ile Tyr Ala Ser Ile Asp Pro Asp Gln Arg Ser Lys Phe Lys His Gly
            20                  25                  30

Leu Arg Leu Asn Phe Gln Val Ser Gln Lys Thr Gln Arg Arg Trp Phe
        35                  40                  45

Leu Asp Lys Leu Val Asp Glu Ile Gly Val Gly Tyr Val Gln Asp Lys
    50                  55                  60

Gly Ser Val Ser His Tyr Ile Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 23
<211> LENGTH: 147
<212> TYPE: PRT
<213> ORGANISM: Artificial Sequence
<220> FEATURE:
<223> OTHER INFORMATION: Synthesized

<400> SEQUENCE: 23

Lys Glu Phe Leu Leu Tyr Leu Ala Gly Phe Val Asp Gly Asp Gly Ser
1               5                   10                  15

Ile Tyr Ala Ser Ile Asp Pro Asp Gln Arg Ser Lys Phe Lys His Gly
            20                  25                  30

Leu Arg Leu Asn Phe Gln Val Ser Gln Lys Thr Gln Arg Arg Trp Phe
        35                  40                  45

Leu Asp Lys Leu Val Asp Glu Ile Gly Val Gly Tyr Val Gln Asp Lys
    50                  55                  60

Gly Ser Val Ser His Tyr Ile Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 24
<211> LENGTH: 147
<212> TYPE: PRT
<213> ORGANISM: Artificial Sequence
<220> FEATURE:

<223> OTHER INFORMATION: Synthesized

<400> SEQUENCE: 24

Lys Glu Phe Leu Leu Tyr Leu Ala Gly Phe Val Asp Gly Asp Gly Ser
1 5 10 15

Ile Phe Ala Ser Ile Glu Pro Ala Gln Arg Ala Lys Phe Lys His Tyr
20 25 30

Leu Arg Leu Val Phe Asn Val Thr Gln Lys Thr Gln Arg Arg Trp Phe
35 40 45

Leu Asp Lys Leu Val Asp Glu Ile Gly Val Gly Tyr Val Ser Asp Ser
50 55 60

Gly Ser Val Ser Leu Tyr Lys Leu Ser Glu Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 25
<211> LENGTH: 147
<212> TYPE: PRT
<213> ORGANISM: Artificial Sequence
<220> FEATURE:
<223> OTHER INFORMATION: Synthesized

<400> SEQUENCE: 25

Lys Glu Phe Leu Leu Tyr Leu Ala Gly Phe Val Asp Ser Asp Gly Ser
1 5 10 15

Ile Phe Ala Ser Ile Val Pro Asp Gln Ser Arg Lys Phe Lys His Ala
20 25 30

Leu Arg Leu Arg Phe Ile Val Ser Gln Asn Thr Arg Arg Arg Trp Phe
35 40 45

Leu Asp Lys Leu Val Asp Glu Ile Gly Val Gly Tyr Val Lys Asp Ser
50 55 60

Gly Arg Ser Ala His Tyr Thr Leu Ser Glu Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 26
<211> LENGTH: 9
<212> TYPE: DNA
<213> ORGANISM: Homo sapiens

<400> SEQUENCE: 26 tgcatgggc 9

<210> SEQ ID NO 27
<211> LENGTH: 9
<212> TYPE: DNA
<213> ORGANISM: Homo sapiens

<400> SEQUENCE: 27 acgtacccg 9

<210> SEQ ID NO 28
<211> LENGTH: 9
<212> TYPE: DNA
<213> ORGANISM: Homo sapiens

<400> SEQUENCE: 28 aactgagga 9

<210> SEQ ID NO 29
<211> LENGTH: 9
<212> TYPE: DNA
<213> ORGANISM: Homo sapiens

<400> SEQUENCE: 29 ttgactcct 9

<210> SEQ ID NO 30
<211> LENGTH: 9
<212> TYPE: DNA
<213> ORGANISM: Homo sapiens

<400> SEQUENCE: 30 gctggactg 9

<210> SEQ ID NO 31
<211> LENGTH: 9
<212> TYPE: DNA
<213> ORGANISM: Homo sapiens

<400> SEQUENCE: 31 cgacctgac 9

<210> SEQ ID NO 32
<211> LENGTH: 9
<212> TYPE: DNA
<213> ORGANISM: Homo sapiens

<400> SEQUENCE: 32 ttgtgtctg 9

<210> SEQ ID NO 33
<211> LENGTH: 9
<212> TYPE: DNA
<213> ORGANISM: Homo sapiens

<400> SEQUENCE: 33 aacacagac 9

<210> SEQ ID NO 34
<211> LENGTH: 24
<212> TYPE: DNA

<213> ORGANISM: Artificial Sequence
<220> FEATURE:
<223> OTHER INFORMATION: Synthesized

<400> SEQUENCE: 34
cactggactg gtatttgtgt ctga 24

<210> SEQ ID NO 35
<211> LENGTH: 24
<212> TYPE: DNA
<213> ORGANISM: Artificial Sequence
<220> FEATURE:
<223> OTHER INFORMATION: Synthesized

<400> SEQUENCE: 35
tgctggactg gtatttgtgt ctga 24

<210> SEQ ID NO 36
<211> LENGTH: 20
<212> TYPE: DNA
<213> ORGANISM: Artificial Sequence
<220> FEATURE:
<223> OTHER INFORMATION: Synthesized

<400> SEQUENCE: 36
ccactcattc ttggcaggat 20

<210> SEQ ID NO 37
<211> LENGTH: 21
<212> TYPE: DNA
<213> ORGANISM: Artificial Sequence
<220> FEATURE:
<223> OTHER INFORMATION: Synthesized

<400> SEQUENCE: 37
cacagaaaca ctcaccgtag g 21

<210> SEQ ID NO 38
<211> LENGTH: 24
<212> TYPE: DNA
<213> ORGANISM: Artificial Sequence
<220> FEATURE:
<223> OTHER INFORMATION: Synthesized

<400> SEQUENCE: 38
aaattcctcc tcagttgtga gccc 24

<210> SEQ ID NO 39
<211> LENGTH: 17
<212> TYPE: DNA
<213> ORGANISM: Artificial Sequence
<220> FEATURE:
<223> OTHER INFORMATION: Synthesized

<400> SEQUENCE: 39
agtctggaga gctgcat 17

<210> SEQ ID NO 40
<211> LENGTH: 24
<212> TYPE: DNA
<213> ORGANISM: Artificial Sequence
<220> FEATURE:
<223> OTHER INFORMATION: Synthesized

<400> SEQUENCE: 40
ccagtaagat ttggtgtcta tttc 24

<210> SEQ ID NO 41
<211> LENGTH: 24
<212> TYPE: DNA
<213> ORGANISM: Artificial Sequence
<220> FEATURE:
<223> OTHER INFORMATION: Synthesized

<400> SEQUENCE: 41
atgggctcac aactgaggag gaat 24

<210> SEQ ID NO 42
<211> LENGTH: 22
<212> TYPE: DNA
<213> ORGANISM: Artificial Sequence
<220> FEATURE:
<223> OTHER INFORMATION: Synthesized

<400> SEQUENCE: 42
tccagacttt cacaccttat ag 22

<210> SEQ ID NO 43
<211> LENGTH: 23
<212> TYPE: DNA
<213> ORGANISM: Artificial Sequence
<220> FEATURE:
<223> OTHER INFORMATION: Synthesized

<400> SEQUENCE: 43
tccactttgt atatcccttc tac 23

<210> SEQ ID NO 44
<211> LENGTH: 24
<212> TYPE: DNA
<213> ORGANISM: Artificial Sequence
<220> FEATURE:
<223> OTHER INFORMATION: Synthesized

<400> SEQUENCE: 44
tgctggactg gtatttgtgt ctga 24

<210> SEQ ID NO 45
<211> LENGTH: 20
<212> TYPE: DNA
<213> ORGANISM: Artificial Sequence
<220> FEATURE:
<223> OTHER INFORMATION: Synthesized

<400> SEQUENCE: 45
ccactcattc ttggcaggat 20

<210> SEQ ID NO 46
<211> LENGTH: 21
<212> TYPE: DNA
<213> ORGANISM: Artificial Sequence
<220> FEATURE:
<223> OTHER INFORMATION: Synthesized

<400> SEQUENCE: 46
cacagaaaca ctcaccgtag g 21

<210> SEQ ID NO 47
<211> LENGTH: 19
<212> TYPE: DNA
<213> ORGANISM: Artificial Sequence
<220> FEATURE:

<223> OTHER INFORMATION: Synthesized

<400> SEQUENCE: 47
gtgtctgtct gcacatttc 19

<210> SEQ ID NO 48
<211> LENGTH: 22
<212> TYPE: DNA
<213> ORGANISM: Artificial Sequence
<220> FEATURE:
<223> OTHER INFORMATION: Synthesized

<400> SEQUENCE: 48
agaaggcact tcttctttat ct 22

<210> SEQ ID NO 49
<211> LENGTH: 25
<212> TYPE: DNA
<213> ORGANISM: Artificial Sequence
<220> FEATURE:
<223> OTHER INFORMATION: Synthesized

<400> SEQUENCE: 49
cctcgctgga ctggtatttg tgtct 25

<210> SEQ ID NO 50
<211> LENGTH: 28
<212> TYPE: DNA
<213> ORGANISM: Artificial Sequence
<220> FEATURE:
<223> OTHER INFORMATION: Synthesized

<400> SEQUENCE: 50
tccgatactc taatctccct aggcaagg 28

<210> SEQ ID NO 51
<211> LENGTH: 17
<212> TYPE: DNA
<213> ORGANISM: Artificial Sequence
<220> FEATURE:
<223> OTHER INFORMATION: Synthesized

<400> SEQUENCE: 51
agtctggaga gctgcat 17

<210> SEQ ID NO 52
<211> LENGTH: 24
<212> TYPE: DNA
<213> ORGANISM: Artificial Sequence
<220> FEATURE:
<223> OTHER INFORMATION: Synthesized

<400> SEQUENCE: 52
ccagtaagat ttggtgtcta tttc 24

<210> SEQ ID NO 53
<211> LENGTH: 19
<212> TYPE: DNA
<213> ORGANISM: Artificial Sequence
<220> FEATURE:
<223> OTHER INFORMATION: Synthesized

<400> SEQUENCE: 53
cctcagttgt gagcccatg 19

<210> SEQ ID NO 54
<211> LENGTH: 20
<212> TYPE: DNA
<213> ORGANISM: Artificial Sequence
<220> FEATURE:
<223> OTHER INFORMATION: Synthesized

<400> SEQUENCE: 54
ccactcgttc ttggcaggat 20

<210> SEQ ID NO 55
<211> LENGTH: 21
<212> TYPE: DNA
<213> ORGANISM: Artificial Sequence
<220> FEATURE:
<223> OTHER INFORMATION: Synthesized

<400> SEQUENCE: 55
cacagaaaca ctcaccgtag g 21

<210> SEQ ID NO 56
<211> LENGTH: 24
<212> TYPE: DNA
<213> ORGANISM: Artificial Sequence
<220> FEATURE:
<223> OTHER INFORMATION: Synthesized

<400> SEQUENCE: 56
tgctggactg gtatttgtgt ctga 24

<210> SEQ ID NO 57
<211> LENGTH: 19
<212> TYPE: DNA
<213> ORGANISM: Artificial Sequence
<220> FEATURE:
<223> OTHER INFORMATION: Synthesized

<400> SEQUENCE: 57
ggatccgtgg gaggtctat 19

<210> SEQ ID NO 58
<211> LENGTH: 17
<212> TYPE: DNA
<213> ORGANISM: Artificial Sequence
<220> FEATURE:
<223> OTHER INFORMATION: Synthesized

<400> SEQUENCE: 58
acctgctcca gctctga 17

<210> SEQ ID NO 59
<211> LENGTH: 22
<212> TYPE: DNA
<213> ORGANISM: Artificial Sequence
<220> FEATURE:
<223> OTHER INFORMATION: Synthesized

<400> SEQUENCE: 59
tgcttcggag atccctgaac cc 22

<210> SEQ ID NO 60
<211> LENGTH: 16
<212> TYPE: DNA
<213> ORGANISM: Artificial Sequence
<220> FEATURE:
<223> OTHER INFORMATION: Synthesized

<400> SEQUENCE: 60
accgccaagg atgcac 16

<210> SEQ ID NO 61
<211> LENGTH: 16
<212> TYPE: DNA
<213> ORGANISM: Artificial Sequence
<220> FEATURE:
<223> OTHER INFORMATION: Synthesized

<400> SEQUENCE: 61
gcgggtggga atggag 16

<210> SEQ ID NO 62
<211> LENGTH: 19
<212> TYPE: DNA
<213> ORGANISM: Artificial Sequence
<220> FEATURE:
<223> OTHER INFORMATION: Synthesized

<400> SEQUENCE: 62
ccagcaggcc aggtacacc 19

<210> SEQ ID NO 63
<211> LENGTH: 24
<212> TYPE: DNA
<213> ORGANISM: Artificial Sequence
<220> FEATURE:
<223> OTHER INFORMATION: Synthesized

<400> SEQUENCE: 63
gccatgccat ttgtttcctc catg 24

<210> SEQ ID NO 64
<211> LENGTH: 18
<212> TYPE: DNA
<213> ORGANISM: Artificial Sequence
<220> FEATURE:
<223> OTHER INFORMATION: Synthesized

<400> SEQUENCE: 64
gcatgctcat ggaatggg 18

<210> SEQ ID NO 65
<211> LENGTH: 42
<212> TYPE: PRT
<213> ORGANISM: Artificial Sequence
<220> FEATURE:
<223> OTHER INFORMATION: Synthesized

<400> SEQUENCE: 65

```
Ser Leu Pro Gly Ser Val Gly Gly Leu Ser Pro Ser Gln Ala Ser Ser
1               5                   10                  15

Ala Ala Ser Ser Ala Ser Ser Ser Pro Gly Ser Gly Ile Ser Glu Ala
            20                  25                  30

Leu Arg Ala Gly Ala Gly Ser Gly Thr Gly
        35                  40
```

<210> SEQ ID NO 66
<211> LENGTH: 1065
<212> TYPE: DNA
<213> ORGANISM: Artificial Sequence
<220> FEATURE:
<223> OTHER INFORMATION: Synthesized

<400> SEQUENCE: 66

```
atgaatacaa aatataataa agagttctta ctctacttag cagggtttgt agacgctgac     60
ggttccatct atgcctgtat cacgcctcgt caaactcata agttcaagca cgttctggcg    120
ctcgggttct cagtcattca gcgtacacgt cgccgttggt tcctcgacaa gctggtggac    180
gagatcggtg tgggttacgt gcgtgacagg gatacgacca gcgaatacag actgtcccag    240
atcaagcctt tgcataattt tttaacacaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaggacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctatgccag tatcgatcct    660
gatcaacgga gtaagttcaa gcacgggctg aggctcaatt tccaggtctc tcagaagaca    720
cagcgccgtt ggttcctcga caagctggtg gacgagatcg gtgtgggtta cgtgcaggac    780
aagggcagcg tctcccatta cattctgtcc cagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
gaccagatcg ccgctctgaa cgactccaag acccgcaaga ccacttccga aaccgtccgc   1020
gccgttctag acagtctctc cgagaagaag aagtcgtccc cctaa                   1065
```

<210> SEQ ID NO 67
<211> LENGTH: 1065
<212> TYPE: DNA
<213> ORGANISM: Artificial Sequence
<220> FEATURE:
<223> OTHER INFORMATION: Synthesized

<400> SEQUENCE: 67

```
atgaatacaa aatataataa agagttctta ctctacttag cagggtttgt agacgctgac     60
ggttccatct atgcctgtat cacgcctcgt caagattata agttcaagca caatctggcg    120
ctcgggttca gtgtcattca gcgtacacgt cgccgttggt tccttgacaa gctggtggac    180
gagatcggtg tgggttacgt gcgtgacagg gatacgacca gcgaatacag actgtcccag    240
atcaagcctt tgcataattt tttaacacaa ctacaacctt ttctaaaact aaaacaaaaa    300
caagcaaatt tagttttaaa aattattgaa caacttccgt cagcaaaaga atccccggac    360
aaattcttag aagtttgtac atgggtggat caaattgcag ctctgaatga ttcgaggacg    420
cgtaaaacaa cttctgaaac cgttcgtgct gtgctagaca gtttaccagg atccgtggga    480
ggtctatcgc catctcaggc atccagcgcc gcatcctcgg cttcctcaag cccgggttca    540
gggatctccg aagcactcag agctggagca ggttccggca ctggatacaa caaggaattc    600
ctgctctacc tggcgggctt cgtcgacggg gacggctcca tctatgccag tatcgatcct    660
gatcaacgga gtaagttcaa gcacgggctg aggctcaatt tccaggtctc tcagaagaca    720
cagcgccgtt ggttcctcga caagctggtg gacgagatcg gtgtgggtta cgtgcaggac    780
aagggcagcg tctcccatta cattctgtcc gagatcaagc ctctgcacaa cttcctgacc    840
cagctccagc ccttcctgaa gctcaagcag aagcaggcca acctcgtgct gaagatcatc    900
gagcagctgc cctccgccaa ggaatccccg gacaagttcc tggaggtgtg cacctgggtg    960
```

gaccagatcg ccgctctgaa cgactccaag acccgcaaga ccacttccga aaccgtccgc 1020
gccgttctag acagtctctc cgagaagaag aagtcgtccc cctaa 1065

<210> SEQ ID NO 68
<211> LENGTH: 1065
<212> TYPE: DNA
<213> ORGANISM: Artificial Sequence
<220> FEATURE:
<223> OTHER INFORMATION: Synthesized

<400> SEQUENCE: 68
atgaatacaa aatataataa agagttctta ctctacttag cagggtttgt agacgctgac 60
ggttccatct atgcctgtat cacgcctcgt caactttgta agttcaagca cgggctggcg 120
ctcgggttct cggtcattca gcgtacacgt cgccgttggt tcctcgacaa gctggtggac 180
gagatcggtg tgggttacgt gcgtgacagg gatacgacca gcgaatacag actgtcccag 240
atcaagcctt tgcataattt tttaacacaa ctacaacctt ttctaaaact aaaacaaaaa 300
caagcaaatt tagttttaaa aattattgaa caacttccgt cagcaaaaga atccccggac 360
aaattcttag aagtttgtac atgggtggat caaattgcag ctctgaatga ttcgaggacg 420
cgtaaaacaa cttctgaaac cgttcgtgct gtgctagaca gtttaccagg atccgtggga 480
ggtctatcgc catctcaggc atccagcgcc gcatcctcgg cttcctcaag cccgggttca 540
gggatctccg aagcactcag agctggagca ggttccggca ctggatacaa caaggaattc 600
ctgctctacc tggcgggctt cgtcgacggg gacggctcca tctatgccag tatcgatcct 660
gatcaacgga gtaagttcaa gcacgggctg aggctcaatt tccaggtctc tcagaagaca 720
cagcgccgtt ggttcctcga caagctggtg gacgagatcg gtgtgggtta cgtgcaggac 780
aagggcagcg tctcccatta cattctgtcc gagatcaagc ctctgcacaa cttcctgacc 840
cagctccagc ccttcctgaa gctcaagcag aagcaggcca acctcgtgct gaagatcatc 900
gagcagctgc cctccgccaa ggaatccccg gacaagttcc tggaggtgtg cacctgggtg 960
gaccagatcg ccgctctgaa cgactccaag acccgcaaga ccacttccga aaccgtccgc 1020
gccgttctag acagtctctc cgagaagaag aagtcgtccc cctaa 1065

<210> SEQ ID NO 69
<211> LENGTH: 1065
<212> TYPE: DNA
<213> ORGANISM: Artificial Sequence
<220> FEATURE:
<223> OTHER INFORMATION: Synthesized

<400> SEQUENCE: 69
atgaatacaa aatataataa agagttctta ctctacttag cagggtttgt agacgctgac 60
ggttccatct atgcctgtat cacgcctcgt caaacgcata agttcaagca caatctggcg 120
ctcgggttca gtgtcattca gcgtacacgt cgccgttggt tccttgacaa gctggtggac 180
gagatcggtg tgggttacgt gcgtgacagg gatacgacca gcgaatacag actgtcccag 240
atcaagcctt tgcataattt tttaacacaa ctacaacctt ttctaaaact aaaacaaaaa 300
caagcaaatt tagttttaaa aattattgaa caacttccgt cagcaaaaga atccccggac 360
aaattcttag aagtttgtac atgggtggat caaattgcag ctctgaatga ttcgaggacg 420
cgtaaaacaa cttctgaaac cgttcgtgct gtgctagaca gtttaccagg atccgtggga 480

```
ggtctatcgc catctcaggc atccagcgcc gcatcctcgg cttcctcaag cccgggttca    540

gggatctccg aagcactcag agctggagca ggttccggca ctggatacaa caaggaattc    600

ctgctctacc tggcgggctt cgtcgacggg gacggctcca tctatgccag tatcgatcct    660

gatcaacgga gtaagttcaa gcacgggctg aggctcaatt tccaggtctc tcagaagaca    720

cagcgccgtt ggttcctcga caagctggtg gacgagatcg gtgtgggtta cgtgcaggac    780

aagggcagcg tctcccatta cattctgtcc gagatcaagc ctctgcacaa cttcctgacc    840

cagctccagc ccttcctgaa gctcaagcag aagcaggcca acctcgtgct gaagatcatc    900

gagcagctgc cctccgccaa ggaatccccg gacaagttcc tggaggtgtg cacctgggtg    960

gaccagatcg ccgctctgaa cgactccaag acccgcaaga ccacttccga aaccgtccgc   1020

gccgttctag acagtctctc cgagaagaag aagtcgtccc cctaa                   1065
```

<210> SEQ ID NO 70
<211> LENGTH: 1065
<212> TYPE: DNA
<213> ORGANISM: Artificial Sequence
<220> FEATURE:
<223> OTHER INFORMATION: Synthesized

<400> SEQUENCE: 70

```
atgaatacaa aatataataa agagttctta ctctacttag cagggtttgt agacggtgac     60

ggttccatct tcgcctccat tgaaccagcg caacgggcga agttcaagca ctatctgcgt    120

ctcgtgttca atgtcactca gaagacacag cgccgttggt tcctcgacaa gctggtggac    180

gagatcggtg tgggttacgt gtctgactct ggcagcgtct ccctttacaa gctcagcgaa    240

attaaaccat tgcataattt tttaacacaa ctacaacctt ttctaaaact aaaacaaaaa    300

caagcaaatt tagttttaaa aattattgaa caacttccgt cagcaaaaga atccccggac    360

aaattcttag aagtttgtac atgggtggat caaattgcag ctctgaatga ttcgaagacg    420

cgtaaaacaa cttctgaaac cgttcgtgct gtgctagaca gtttaccagg atccgtggga    480

ggtctatcgc catctcaggc atccagcgcc gcatcctcgg cttcctcaag cccgggttca    540

gggatctccg aagcactcag agctggagca ggttccggca ctggatacaa caaggaattc    600

ctgctctacc tggcgggctt cgtcgacagc gacggctcca tctttgccag tatcgtgcct    660

gatcaatcgc gtaagttcaa gcatgctctc cggttgcgct ttattgtcag tcagaataca    720

aggcgccgtt ggttcctcga caagctggtg gacgagatcg gtgtgggtta cgtgaaggac    780

tctggtcgga gcgcccatta tactctgtcc gagatcaagc ctctgcacaa cttcctgacc    840

cagctccagc ccttcctgaa gctcaagcag aagcaggcca acctcgtgct gaagatcatc    900

gagcagctgc cctccgccaa ggaatccccg gacaagttcc tggaggtgtg cacctgggtg    960

gaccagatcg ccgctctgaa cgactccaag acccgcaaga ccacttccga aaccgtccgc   1020

gccgttctag acagtctctc cgagaagaag aagtcgtccc cctaa                   1065
```